US008829029B2

(12) United States Patent
Gobbi et al.

(10) Patent No.: US 8,829,029 B2
(45) Date of Patent: *Sep. 9, 2014

(54) DUAL MODULATORS OF $5HT_{2A}$ AND $D_3$ RECEPTORS

(71) Applicant: Hoffmann-La Roche Inc., Nutley, NJ (US)

(72) Inventors: Luca Gobbi, Muttenz (CH); Georg Jaeschke, Basel (CH); Olivier Roche, Folgensbourg (FR); Rosa Maria Rodriguez Sarmiento, Basel (CH); Lucinda Steward, Basel (CH)

(73) Assignee: Hoffmann-La Roche Inc., Nutley, NJ (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/772,390

(22) Filed: Feb. 21, 2013

(65) Prior Publication Data

US 2013/0165432 A1      Jun. 27, 2013

Related U.S. Application Data

(63) Continuation of application No. 13/280,523, filed on Oct. 25, 2011, now abandoned, which is a continuation of application No. 12/175,476, filed on Jul. 18, 2008, now abandoned.

(51) Int. Cl.
*A61K 31/445* (2006.01)
*C07D 413/04* (2006.01)

(52) U.S. Cl.
USPC ............................. 514/321; 546/194; 546/198

(58) Field of Classification Search
USPC .................................. 514/321; 546/198, 194
See application file for complete search history.

(56) References Cited

U.S. PATENT DOCUMENTS

| | | | | |
|---|---|---|---|---|
| 6,140,345 | A * | 10/2000 | Strupczewski et al. | 514/321 |
| 6,335,326 | B1 * | 1/2002 | Den Hartog et al. | 514/217.1 |
| 7,772,252 | B2 * | 8/2010 | Hendrix et al. | 514/316 |
| 7,795,437 | B2 * | 9/2010 | Gobbi et al. | 546/168 |
| 7,858,630 | B2 * | 12/2010 | Gobbi et al. | 514/254.04 |
| 8,039,490 | B2 * | 10/2011 | Gobbi et al. | 514/330 |
| 8,097,637 | B2 * | 1/2012 | Gobbi et al. | 514/330 |
| 8,415,350 | B2 * | 4/2013 | Gobbi et al. | 514/235.5 |
| 2003/0229066 | A1 | 12/2003 | Hendrix et al. | |

FOREIGN PATENT DOCUMENTS

| | | |
|---|---|---|
| EP | 1688412 | 8/2006 |
| WO | 94/27992 | 12/1994 |
| WO | WO9427992 | * 12/1994 |
| WO | 95/11680 | 5/1995 |
| WO | 98/34933 | 8/1998 |
| WO | 02/066446 | 8/2002 |
| WO | 2007/093540 | 8/2007 |

OTHER PUBLICATIONS

Gobbi et al. "Benzoyl-piperidine . . . " CA147:300997 (2007) provided in the parent case.*
Hansen et al. "Preparation of . . . " CA 122:214057 (1995).*
Patani et al. "Bioisosterism: a rational . . . " Chem. Rev. 96 p. 3147-3176 (1996).*
Ravina et al. "Conformationally contstrain . . . " j. Med. Chem. 42, p. 2774-2797 (1999).*
Gobbi (Chem Abstract 147:3009972007).
Pompeiano et al., Brain Res. Mol. 23:163-178 ( 1994).
Gurevich, E. V., "Neuropsychopharmacology" 20:60-80 ( 1999).
Gurevich, E.V. et al., Arch. Gen. Psychiatry 54:225-232 ( 1997).
Roth et al., Pharmacol. Ther. 79:231-257 ( 1998).
De Angelis, L., Curr. Opin. Investig. Drugs. 3:106-112 ( 2002).
Chilean Office Action for CL2162-08, (2008).
Meltzer et al., J. Pharmacol. Exp. Ther. 251:238-246 ( 1989).
Arranz et al., "Lancet" 355:1615-1616 ( 2000).
Gurevich, E.V. et al., Neuropsychopharmacology 20:60-80 ( 1999).
Patani et al., Chem. Rev. 96:3147-3176 ( 1996).
Pompeiano et al., "Brain Res. Mol." 23:163-178 ( 1994).
Roth et al., "Pharmacol. Ther." 79:231-257 ( 1998).
Porras et al., Neuropsychopharmacology 26:311-324 ( 2002).
Leikin et al., Med. Toxicol. Adverse Drug Exp. 4:324-350 ( 1989).
Harrison, P.J., Br. J. Psychiatry Suppl. 38:12-22 ( 1999).
Leikin et al., "Med. Toxicol. Adverse Drug Exp." 4:324-350 ( 1989).
De Angelis, L., "Curr. Opin. Investig. Drugs" 3:106-112 ( 2002).
Wustrow, Journal of Medicinal Chemistry 41:760-771 ( 1998).
Joyce et al., "Drug Discovery Today 1" 10(13):917-925 ( 2005).
Harrison, P. J., "Br. J. Psychiatry" ((Suppl. 38)),:12-22 ( 1999).
Spurlock et al., Mol. Psychiatry 3:42-49 ( 1998).
Barnes, N. M., "Neuropharmacology" 38:1083-1152 ( 1999).
Roth et al., Nat. Rev. Drug Discovery 3:353-359 ( 2004).
Arranz et al., Lancet 355:1615-1616 ( 2000).
Barnes, N.M., Neuropsychopharmacology 38:1083-1152 ( 1999).
Meltzer et al., "J. Pharmacol. Exp. Ther." 251:238-246 ( 1989).
Ravina et al., J. Med. Chem 42:2774-2797 ( 1999).

(Continued)

*Primary Examiner* — Celia Chang

(57) ABSTRACT

The present invention relates to compounds of the formula (I)

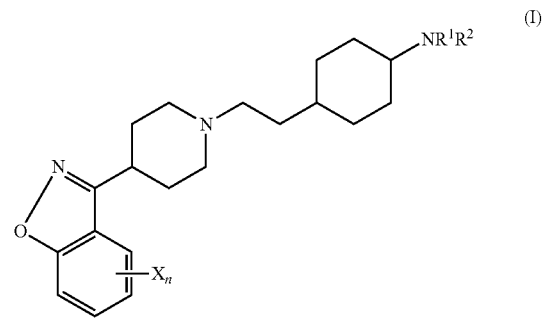

wherein $R^1$, $R^2$, X and n are as defined in the specification as dual modulators of the serotonin $5\text{-HT}_{2a}$ and dopamine $D_3$ receptors, their manufacture, pharmaceutical compositions containing them and their use for the treatment of psychotic disorders, as well as other diseases such as depression and anxiety, drug dependence, dementias and memory impairment.

18 Claims, No Drawings

(56) References Cited

OTHER PUBLICATIONS

Spurlock et al., "Mol. Psychiatry" 3:42-49 (1998).
(International Search Report for PCT/EP2008/059356 Apr. 15, 2009).
Lieberman et al., New Eng. J. Med. 353:1209-1223 (2005).
Missale et al., Physiol. Rev. 78:189-225 (1998).
Roth et al., "Nat. Rev. Drug. Discovery" 3:353-359 (2004).
"Journal of Medicinal Chemistry" 41:760-771 (1998).
Porras et al., "Neuropsychopharmacology" 26:311-324 (2002).
Lieberman et al., "N. Engl. J. Med." 353:1209-1223 (2005).
Gobbi et al., "CA 147:300997 (2007)".
Gurevich, E. V., "Arch. Gen. Psychiatry" 54:225-232 (1997).
(Hansen Chem Abstract 122:214057(1995).
Joyce, J.N. et al., Drug Discovery Today 1 10(13):917-925 (2005).
Missale et al., "Physiol. Rev." 78:189-225 (1998).

\* cited by examiner

DUAL MODULATORS OF 5HT$_{2A}$ AND D$_3$ RECEPTORS

PRIORITY TO RELATED APPLICATION(S)

This application is a continuation of U.S. application Ser. No. 13/280,523, filed Oct. 25, 2011, now pending, which is a continuation of U.S. application Ser. No. 12/175,476, filed Jul. 18, 2008, now pending; which claims the benefit of European Patent Application No. 07113252.6, filed Jul. 26, 2007. The entire contents of the above-identified applications are hereby incorporated by reference.

BACKGROUND OF THE INVENTION

Schizophrenia is characterized by complex symptomatology including positive symptoms, (i.e. delusions and hallucinations), and negative symptoms, (i.e. anhedonia, restricted fluency and productivity of thought and speech). In addition it is now well recognized that cognitive impairment is the third major diagnostic category of schizophrenia, characterized by loss in working memory as well as other deficits. Other symptoms include aggressiveness, depression and anxiety (Stahl, S. M. (2000) Essential Psychopharmacology. Neuroscientific Basis and Practical Applications. Cambridge University Press, second edition, Cambridge, UK). The different categories and the clinical features of the disorder are defined in diagnostic schemes such as DSM-IV (Diagnostic and statistical manual of mental disorders, 4th edition) or ICD-10 (International classification of diseases, $10^{th}$ edition).

Currently used medications to treat schizophrenia, bipolar mania and other psychoses, include antipsychotics both typical (D$_2$/D$_3$ preferring) or the more recent atypicals, which exhibit polypharmacology interacting at multiple receptors (eg., D$_1$, D$_2$, D$_3$, D$_4$, 5-HT$_{1A}$, 5-HT$_{2A}$, 5-HT$_{2C}$, H$_1$, M$_1$, M$_2$, M$_4$, etc; Roth, B. L. et al. (2004) Magic shotguns versus magic bullets: selectively non-selective drugs for mood disorders and schizophrenia. Nat. Rev. Drug Discov. 3, 353-359). These antipsychotics, although relatively successful (some patients exhibit treatment resistance) at treating the positive symptoms of schizophrenia, are less effective at treating negative symptoms, cognitive deficits, and associated depression and anxiety, all of which lead to reduced patient quality of life and socioeconomic problems (Lieberman, J. A. et al. Clinical Antipsychotic Trials of Intervention Effectiveness (CATIE) Investigators. (2005) Effectiveness of antipsychotic drugs in patients with chronic schizophrenia. N. Engl. J. Med. 353, 1209-1223). Furthermore, patient compliance is compromised by prevalent side effects such as weight gain, extrapyramidal symptoms (EPS), and cardiovascular effects (Lieberman, J. A. et al. Clinical Antipsychotic Trials of Intervention Effectiveness (CATIE) Investigators. (2005) Effectiveness of antipsychotic drugs in patients with chronic schizophrenia. N. Engl. J. Med. 353, 1209-1223). In the current invention, compounds with high affinity and greater selectivity for D$_3$ and 5-HT$_{2A}$ receptors are described and are proposed to treat psychoses and other diseases, with fewer associated side affects.

Dopamine, a major catecholamine neurotransmitter, is involved in the regulation of a variety of functions which include emotion, cognition, motor functions, and positive reinforcement, (Purves, D. et al. (2004) Neuroscience. Sinauer, third edition, Sunderland, Mass.). The biological activities of dopamine are mediated through G protein-coupled receptors (GPCRs) and in human, five different dopamine receptors D$_1$-D$_5$ have been identified, where the D$_2$-like receptors (D$_2$, D$_3$ and D$_4$) couple to the G-protein G$_{\alpha I}$ (Missale, C. et al. (1998) Dopamine receptors: from structure to function. Physiol. Rev. 78, 189-225). The D$_3$ dopamine receptor is most highly expressed in the nucleus accumbens (Gurevich, E. V., Joyce, J. N. (1999) Distribution of dopamine D$_3$ receptor expressing neurons in the human forebrain: comparison with D$_2$ receptor expressing neurons. Neuropsychopharmacology 20, 60-80), and is proposed to modulate the mesolimbic pathway consisting of neuronal projections from the ventral tegmental area, hippocampus and amygdala to the nucleus accumbens, which projects to the prefrontal and cingulate cortices as well as various thalamic nuclei. The limbic circuit is thought to be important for emotional behavior and thus D$_3$ receptor antagonists are proposed to modulate psychotic symptoms such as hallucinations, delusions and thought disorder (Joyce, J. N. and Millan, M. J., (2005) Dopamine D$_3$ receptor antagonists as therapeutic agents. Drug Discovery Today, 1 July, Vol. 10, No. 13, 917-25), while these antagonists spare the D$_2$ modulated striatal extrapyramidal system (associated with EPS induction). In addition, it has been reported that drug naive schizophrenic patients show altered levels of D$_3$ receptor expression (Gurevich, E. V. et al. (1997) Mesolimbic dopamine D$_3$ receptors and use of antipsychotics in patients with schizophrenia. A postmortem study. Arch. Gen. Psychiatry 54, 225-232) and dopamine release (Laruelle, M. (2000) Imaging dopamine dysregulation in schizophrenia: implication for treatment. Presented at Workshop Schizophr.: Pathol. Bases and Mech. Antipsychotic Action, Chicago), indicating that a disturbed homeostasis of dopamine plays an important role in the etiology of schizophrenic symptoms.

The neurotransmitter serotonin is implicated in several psychiatric conditions including schizophrenia (Kandel, E. R. et al. (eds.; 2000) Principles of Neural Science, 3' edition Appleton & Lange, Norwalk, Conn.). The involvement of serotonin in psychotic disorders is suggested by multiple studies, which include treatment in humans with the psychotropic drug Lysergic acid (LSD; a serotonin agonist) that can induce schizophrenia-like symptoms such as hallucinations (Leikin, J. B. et al. (1989) Clinical features and management of intoxication due to hallucinogenic drugs. Med. Toxicol. Adverse Drug Exp. 4, 324-350). Furthermore, altered brain distribution of serotonin receptors as well as an altered serotonergic tone, have been detected in schizophrenic patients (Harrison, P. J. (1999) Neurochemical alterations in schizophrenia affecting the putative receptor targets of atypical antipsychotics. Focus on dopamine (D1, D3, D4) and 5-HT2A receptors. Br. J. Psychiatry Suppl. 38, 12-22).

In mammals serotonin exerts its biological activities through a family of 14 5-HT GPCRs (Barnes, N. M., Sharp, T. (1999) A review of central 5-HT receptors and their function. Neuropharmacology 38, 1083-1152). The 5-HT$_{2A}$ receptor is most prominently expressed in the prefrontal cortex and at lower levels in the basal ganglia and the hippocampus in human brain (Pompeiano, M. et al. (1994) Distribution of the serotonin 5-HT2 receptor family mRNAs: comparison between 5-HT2A and 5-HT2C receptors. Brain Res. Mol. Brain. Res. 23, 163-178; Pazos, A., Probst, A., Palacios, J. M. (1987) Serotonin receptors in the human brain—IV. Autoradiographic mapping of serotonin-2 receptors. Neuroscience 21, 123-139), and is coupled predominantly to the G-protein G$_{\alpha q}$ (Roth, B. L. et al. (1998) 5-Hydroxytryptamine-2-family receptors (5-hydroxytryptamine-2A, 5-hydroxytryptamine-2B, 5-hydroxytryptamine-2C): where structure meets function. Pharmacol. Ther. 79, 231-257). Genetic linkage studies of a 5-HT$_{2A}$ polymorphism to schizophrenia (Spurlock, G. et al. (1998) A family based association study of T102C polymorphism in 5HT2A and schizophrenia plus identification of new polymorphisms in the promoter. Mol. Psychiatry. 3, 42-49), as well as responsiveness to antipsychotic drugs (Arranz, M. J. et al. (2000) Pharmacogenetic prediction of clozapine response. Lancet 355, 1615-1616), further suggests a role for the 5-HT$_{2A}$ receptor both in the treatment and pathology of psychosis. In addition, dopaminergic neurotransmission appears to be under the afferent regulation of the 5-HT$_{2A}$ receptor (Porras, G. et al. 5-HT2A and 5-HT2C/2B receptor subtypes modulate dopamine release induced in vivo by amphetamine and morphine in both the rat nucleus accumbens and striatum. Neuropsychopharmacology 26, 311-324-2002).

Overall 5-HT$_{2A}$ receptor antagonists are proposed to be suitable for the treatment of disorders associated with dysfunctional dopaminergic systems. Moreover, 5-HT$_{2A}$ receptor antagonism has been recognized as beneficial for the treatment of psychosis (reviewed in de Angelis, L. (2002) 5-HT2A antagonists in psychiatric disorders. Curr. Opin. Investig. Drugs 3, 106-112) and indeed is one of the defining features of so-called atypical antipsychotic drugs which are characterized by a relatively high affinity for the 5-HT$_{2A}$— relative to the D$_2$ receptor (Meltzer, H. Y. et al. (1989) Classification of typical and atypical antipsychotic drugs on the basis of dopamine D-1, D-2 and serotonin2 pKi values. J. Pharmacol. Exp. Ther. 251, 238-246).

SUMMARY OF THE INVENTION

The present invention provides compounds of the general formula (I)

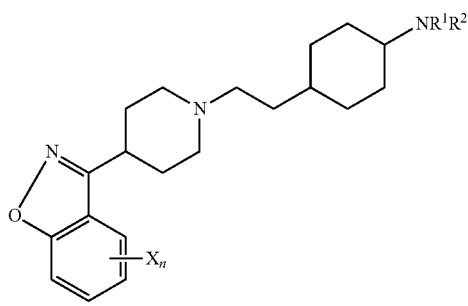

wherein:
each X is independently halogen, cyano; $C_{1-6}$-alkyl, $C_{1-6}$-alkoxy or $C_{1-6}$-haloalkyl;
n is 0, 1, 2 or 3;
$R^1$ is H or $C_{1-6}$-alkyl;
$R^2$ is

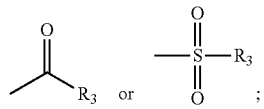

$R^3$ is hydrogen, $C_{1-6}$-alkyl, $C_{2-6}$-alkenyl, $C_{2-6}$-alkynyl, $C_{1-6}$-alkoxy, $C_{3-10}$-cycloalkyl, aryl, 4 to 10 membered heterocycloalkyl, or 5 to 10 membered heteroaryl, each of which is optionally substituted by one to five substituents selected from the group consisting of:
halo,
cyano,
—SO$_2$—C$_{1-6}$-alkyl,
hydroxy,
$C_{1-6}$-alkyl,
$C_{1-6}$-haloalkyl,
—CO(O)—C$_{1-6}$-alkyl,
$C_{1-6}$-alkoxy optionally substituted by one or more $R^a$,
$C_{3-10}$-cycloalkyl optionally substituted by one or more $R^a$,
4 to 10 membered heterocycloalkyl optionally substituted by one or more $R^a$,
aryl optionally substituted by one or more $R^a$,
5 to 10 membered heteroaryl optionally substituted by one or more $R^a$, and
—NR$^b$R$^c$,
wherein R$^b$ is H or $C_{1-6}$-alkyl and wherein R$^c$ is H, $C_{1-6}$-alkyl or aryl optionally substituted by one or more $R^a$;
wherein R$^a$ is selected from:
halo,
cyano,
oxo,
hydroxy,
halobenzenesulfonyl,
$C_{1-6}$-alkyl
$C_{1-6}$-haloalkyl,
—NH(CO)—C$_{1-6}$-alkyl,
di(C$_{1-6}$)alkylamino,
—O(CO)—C$_{1-6}$-alkyl,
$C_{1-6}$-alkylsulfonyl,
$C_{1-6}$-alkoxy
$C_{1-6}$-haloalkoxy,
4 to 10 membered heterocycloalkyl
aryl,
aryloxy, and
5 to 10 membered heteroaryl;
as well as pharmaceutically acceptable salts thereof.

Compounds of formula (I) according to the invention are dual modulators of the serotonin 5-HT$_{2a}$ and dopamine D$_3$ receptors.

The compounds of the invention have high affinity for the dopamine D$_3$ and serotonin (5-Hydroxytryptamine; 5-HT) 5-HT$_{2A}$ receptors and are effective in the treatment of psychotic disorders, as well as other diseases such as depression and anxiety, drug dependence, dementias and memory impairment. Psychotic disorders encompass a variety of diseases, which include schizophrenia, schizoaffective disorders, bipolar disease, mania, psychotic depression, and other psychoses involving paranoia and delusions.

DETAILED DESCRIPTION OF THE INVENTION

The following definitions of the general terms used in the present description apply irrespective of whether the terms in question appear alone or in combination. It must be noted that, as used in the specification and the appended claims, the singular forms "a", "an," and "the" include plural forms unless the context clearly dictates otherwise.

"Aryl" represents an aromatic carbocyclic group consisting of one individual ring, or one or more fused rings in which at least one ring is aromatic in nature. Preferred aryl groups are those having from 6 to 10 ring atoms. Preferred aryl group s include phenyl and naphthyl, as well as those specifically illustrated by the examples herein below.

"Aryloxy" denotes an aryl group as defined hereinabove that is connected via an oxygen atom. An example of aryloxy is phenoxy.

"$C_{1-6}$-alkyl" denotes a straight- or branched-chain hydrocarbon group containing from 1 to 6 carbon atoms, for example, methyl, ethyl, propyl, isopropyl, isobutyl, sec-butyl, tert-butyl, pentyl, n-hexyl as well as those specifically illustrated by the examples herein below.

"Di($C_{1-6}$-alkyl)amino" denotes a nitrogen atom substituted by two $C_{1-6}$-alkyl groups as defined hereinabove. Examples of di($C_{1-6}$-alkyl)amino are dimethylamino, diethylamino, dipropylamino, methylethylamino as well as those groups which are specifically illustrated by the examples herein below.

"Halo" or "Halogen" denotes chlorine, iodine, fluorine and bromine.

"$C_{1-6}$-haloalkyl" denotes a $C_{1-6}$-alkyl group as defined above which is substituted by one or more halogen atom. Examples of $C_{1-6}$-haloalkyl include but are not limited to methyl, ethyl, propyl, isopropyl, isobutyl, sec-butyl, tert-butyl, pentyl or n-hexyl substituted by one or more Cl, F, Br or I atom(s) as well as those groups specifically illustrated by the examples herein below. Preferred $C_1$-$C_7$-haloalkyl are difluoro- or trifluoro-methyl or ethyl.

"$C_{1-6}$-alkylsulfonyl" denotes a sulfonyl group ($SO_2$) which is substituted by a $C_{1-6}$-alkyl group as defined above.

"$C_{1-6}$-alkoxy" denotes an alkyl group as defined above that is connected via an oxygen atom.

"$C_{1-6}$-haloalkoxy" denotes a $C_{1-6}$-alkoxy group as defined above which is substituted by one or more halogen atom. Examples of $C_{1-6}$-haloalkoxy include but are not limited to methoxy or ethoxy, substituted by one or more Cl, F, Br or I atom(s) as well as those groups specifically illustrated by the examples herein below. Preferred $C_1$-$C_7$ haloalkoxy are difluoro- or trifluoro-methoxy or ethoxy.

The term "lower alkenyl" denotes a straight- or branched-chain carbon group containing from 2-7, preferably from 2-4, carbon atoms, wherein at least one bond is a double bond.

The term "thioalkyl" denotes the group —SR wherein R is an alkyl group as defined above.

"$C_{3-10}$-cycloalkyl" denotes a monovalent saturated cyclic moiety, consisting of one, two or three carbon rings having 3 to 10 carbon atoms as ring members and includes but is not limited to cyclopropyl, cyclobutyl, cyclopentyl, cyclohexyl, cycloheptyl and polyspiro groups such as bicyclo[2.2.2]octanyl, bicyclo[2.2.1]heptanyl, bicyclo[3.2.1]octanyl or adamantanyl as well as those groups specifically illustrated by the examples herein below.

The term "thiophenyl" as used herein is synonymous with "thienyl" and denotes a thiophene substituent, i.e., $C_4H_4S$.

"5 to 10 membered heteroaryl" means a monocyclic, bicyclic or tricyclic radical of 5 to 10 ring atoms having at least one aromatic ring and furthermore containing one, two, or three ring heteroatoms selected from N, O, and S, the remaining ring atoms being C. Heteroaryl can optionally be substituted with one, two, three or four substituents, wherein each substituent is independently hydroxy, cyano, alkyl, alkoxy, thioalkyl, halo, haloalkyl, hydroxyalkyl, alkoxycarbonyl, amino, acetyl, —NHCOOC($CH_3$)$_3$ or halogen substituted benzyl, or for the non aromatic part of cyclic ring also by oxo, unless otherwise specifically indicated. Examples of heteroaryl moieties include, but are not limited to, optionally substituted imidazolyl, optionally substituted thiophenyl, optionally substituted oxazolyl, optionally substituted isoxazolyl, optionally substituted thiazolyl, optionally substituted pyrazinyl, optionally substituted pyrrolyl, optionally substituted pyridinyl, optionally substituted pyrimidinyl, optionally substituted pyridazinyl, optionally substituted indolyl, optionally substituted isoindolyl, optionally substituted 2,3-dihydroinidolyl, optionally substituted indazolyl, optionally substituted naphthyridinyl, optionally substituted isoquinolinyl, optionally substituted carbazol-9-yl, optionally substituted furanyl, optionally substituted benzofuranyl, optionally substituted quinolinyl, optionally substituted benzo[1,3]dioxolyl, optionally substituted benzo[1,2,3]thiadiazolyl, optionally substituted benzo[b]thiophenyl, optionally substituted 9H-thioxanthenyl, optionally substituted thieno[2,3-c]pyridinyl, optionally substituted 3H-imidazo[4,5,b]pyridinyl, optionally substituted phthalazinyl, optionally substituted 2,3-dihydrobenzo[1,4]dioxinyl, and the like or those which are specifically exemplified herein.

Preferred 5 to 10 membered heteroaryls are 5 or 6 membered heteroaryls.

"4 to 10 heterocycloalkyl" means a monovalent saturated moiety, consisting of one, two or three rings, incorporating one, two, or three heteroatoms (chosen from nitrogen, oxygen or sulfur). Heterocycloalkyl can optionally be substituted with one, two, three or four substituents, wherein each substituent is independently hydroxy, alkyl, alkoxy, thioalkyl, halo, haloalkyl, hydroxyalkyl, alkoxycarbonyl, amino, alkylamino, dialkylamino, aminocarbonyl, or carbonylamino, unless otherwise specifically indicated. Examples of heterocyclic moieties include, but are not limited to, piperidinyl, piperazinyl, homopiperazinyl, azepinyl, pyrrolidinyl, pyrazolidinyl, imidazolinyl, imidazolidinyl, oxazolidinyl, isoxazolidinyl, morpholinyl, thiazolidinyl, isothiazolidinyl, quinuclidinyl, quinolinyl, isoquinolinyl, benzimidazolyl, chromanyl, thiadiazolylidinyl, benzothiazolidinyl, benzoazolylidinyl, dihydrofuryl, tetrahydrofuryl, dihydropyranyl, tetrahydropyranyl, thiomorpholinyl, dioxothiomorpholinyl thiomorpholinylsulfoxide, thiomorpholinylsulfone, dihydroquinolinyl, dihydrisoquinolinyl, tetrahydroquinolinyl, tetrahydroisoquinolinyl, 1-oxo-thiomorpholin, 1,1-dioxo-thiomorpholin, 1,4-diazepane, 1,4-oxazepane as well as those groups specifically illustrated by the examples herein below. Preferred 5 to 10 membered heterocycloalkyls are 5 or 6 membered heterocycloalkyls.

"One or more" denotes herein, 1, 2, 3, 4, 5, 6, 7, 8, 9 or 10 and preferably 1, 2, 3, 4 or 5 and still more preferably 1, 2 or 3.

"Oxo" denotes a group =O.

Where $R^3$ is the group

$R^8$ and $R^9$ can form a 3-, 4-, 5-, or 6-membered saturated ring, optionally comprising one or two heteroatoms selected from oxygen and nitrogen and $R^{10}$ can be a substituent on the ring formed by $R^8$ and $R^9$. In such instances $R^{10}$ can be, for example, halogen, cyano, hydroxyl, $C_{1-6}$alkyl, $C_{1-6}$haloalkyl, and $C_{1-6}$alkoxy.

"Pharmaceutically acceptable" such as pharmaceutically acceptable carrier, excipient, salts, etc., means pharmacologically acceptable, generally safe, substantially non-toxic to the subject to which the particular compound is administered, and neither biologically nor otherwise undesirable.

"Pharmaceutically acceptable salts" of a compound means salts that are pharmaceutically acceptable, as defined herein, and that possess the desired pharmacological activity of the parent compound. Such salts include acid addition salts formed with inorganic acids such as hydrochloric acid, hydrobromic acid, sulfuric acid, nitric acid, phosphoric acid, and the like; or formed with organic acids such as acetic acid, benzenesulfonic acid, benzoic, camphorsulfonic acid, citric acid, ethanesulfonic acid, fumaric acid, glucoheptonic acid, gluconic acid, glutamic acid, glycolic acid, hydroxynaphtoic acid, 2-hydroxyethanesulfonic acid, lactic acid, maleic acid, malic acid, malonic acid, mandelic acid, methanesulfonic acid, muconic acid, 2-naphthalenesulfonic acid, propionic acid, salicylic acid, succinic acid, tartaric acid, p-toluenesulfonic acid, trimethylacetic acid, and the like.

"Therapeutically effective amount" means an amount that is effective to prevent, alleviate or ameliorate symptoms of disease or prolong the survival of the subject being treated.

The present invention provides compounds of the general formula (I)

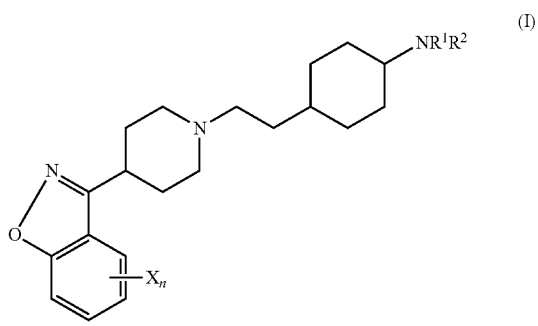

wherein:
each X is independently halogen, cyano; $C_{1-6}$-alkyl, $C_{1-6}$-alkoxy or $C_{1-6}$-haloalkyl;
n is 0, 1, 2 or 3;
$R^1$ is H or $C_{1-6}$-alkyl;
$R^2$ is

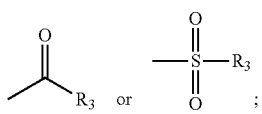

$R^3$ is hydrogen, $C_{1-6}$-alkyl, $C_{2-6}$-alkenyl, $C_{2-6}$-alkynyl, $C_{1-6}$-alkoxy, $C_{3-10}$-cycloalkyl, aryl, 4 to 10 membered heterocycloalkyl, or 5 to 10 membered heteroaryl, each of which is optionally substituted by one to five substituents selected from the group consisting of:
halo,
cyano,
—$SO_2$—$C_{1-6}$-alkyl,
hydroxy,
$C_{1-6}$-alkyl,
$C_{1-6}$-haloalkyl,
—CO(O)—$C_{1-6}$-alkyl,
$C_{1-6}$-alkoxy optionally substituted by one or more $R^a$,
$C_{3-10}$-cycloalkyl optionally substituted by one or more $R^a$,
4 to 10 membered heterocycloalkyl optionally substituted by one or more $R^a$,
aryl optionally substituted by one or more $R^a$,
5 to 10 membered heteroaryl optionally substituted by one or more $R^a$, and
—$NR^bR^c$,
   wherein $R^b$ is H or $C_{1-6}$-alkyl and wherein $R^c$ is H, $C_{1-6}$-alkyl or aryl optionally
   substituted by one or more $R^a$;
wherein $R^a$ is selected from:
halo,
cyano,
oxo,
hydroxy,
halobenzenesulfonyl,
$C_{1-6}$-alkyl
$C_{1-6}$-haloalkyl,
—NH(CO)—$C_{1-6}$-alkyl,
di($C_{1-6}$)alkylamino,
—O(CO)—$C_{1-6}$-alkyl,
$C_{1-6}$-alkylsulfonyl,
$C_{1-6}$-alkoxy
$C_{1-6}$-haloalkoxy,
4 to 10 membered heterocycloalkyl
aryl,
aryloxy, and
5 to 10 membered heteroaryl;
as well as pharmaceutically acceptable salts thereof.

Compounds of formula (I) can form acid addition salts with acids, such as conventional pharmaceutically acceptable acids, for example hydrochloride, hydrobromide, phosphate, acetate, fumarate, maleate, salicylate, sulphate, pyruvate, citrate, lactate, mandelate, tartarate, and methanesulphonate. Preferred are the hydrochloride salts. Also solvates and hydrates of compounds of formula I and their salts form part of the present invention.

Compounds of formula (I) can have one or more asymmetric carbon atoms and can exist in the form of optically pure enantiomers, mixtures of enantiomers such as, for example, racemates, optically pure diastereoisomers, mixtures of diastereoisomers, diastereoisomeric racemates or mixtures of diastereoisomeric racemates. The optically active forms can be obtained for example by resolution of the racemates, by asymmetric synthesis or asymmetric chromatography (chromatography with a chiral adsorbens or eluant). The invention embraces all of these forms.

It will be appreciated, that the compounds of general formula (I) in this invention can be derivatized at functional groups to provide derivatives which are capable of conversion back to the parent compound in vivo. Physiologically acceptable and metabolically labile derivatives, which are capable of producing the parent compounds of general formula I in vivo are also within the scope of this invention.

Also encompassed by the compounds of formula (I) are those compounds wherein
each X is independently halogen, cyano; $C_{1-6}$-alkyl, $C_{1-6}$-alkoxy or $C_{1-6}$-haloalkyl;
n is 0, 1, 2 or 3;
$R^1$ is H or $C_{1-6}$-alkyl;
$R^2$ is

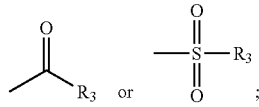

$R^3$ is hydrogen, $C_{1-6}$-alkyl, $C_{2-6}$-alkenyl, $C_{2-6}$-alkynyl, $C_{1-6}$-alkoxy, $C_{3-10}$-cycloalkyl, aryl, 4 to 10 membered heterocycloalkyl, or 5 to 10 membered heteroaryl, each of which is optionally substituted by one to five substituents selected from the group consisting of:
halo,
hydroxy,
$C_{1-6}$-alkyl,
$C_{1-6}$-haloalkyl,
—CO(O)—$C_{1-6}$-alkyl,
$C_{1-6}$-alkoxy optionally substituted by one or more $R^a$, $C_{3-10}$-cycloalkyl optionally substituted by one or more $R^a$,
4 to 10 membered heterocycloalkyl optionally substituted by one or more $R^a$,
aryl optionally substituted by one or more $R^a$,
5 to 10 membered heteroaryl optionally substituted by one or more $R^a$, and
—$NR^bR^c$,
wherein $R^b$ is H or $C_{1-6}$-alkyl and wherein $R^c$ is H, $C_{1-6}$-alkyl or aryl optionally
substituted by one or more $R^a$;
wherein $R^a$ is selected from:
halo,
cyano,
oxo,
hydroxy,
halobenzenesulfonyl,
$C_{1-6}$-alkyl
$C_{1-6}$-haloalkyl,
—NH(CO)—$C_{1-6}$-alkyl,
di($C_{1-6}$)alkylamino,
—O(CO)—$C_{1-6}$-alkyl,
$C_{1-6}$-alkylsulfonyl,
$C_{1-6}$-alkoxy
$C_{1-6}$-haloalkoxy,
4 to 10 membered heterocycloalkyl
aryl,
aryloxy, and
5 to 10 membered heteroaryl;
as well as pharmaceutically acceptable salts thereof.

Also encompassed by the compounds of formula (I) are those compounds wherein
each X is independently fluorine or chlorine;
n is 0, 1 or 2;
$R^1$ is hydrogen;
$R^2$ is

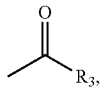

and
wherein $R^3$ is as defined hereinabove for formula (I) as well as pharmaceutically acceptable salts thereof.

Also encompassed by the compounds of formula (I) are the compounds of formula (Ia)

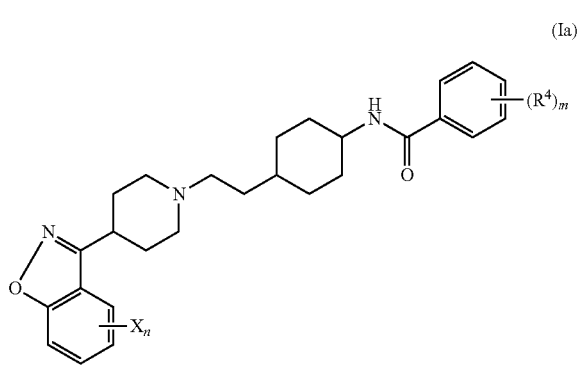

(Ia)

wherein
each X is independently fluorine or chlorine;

n is 0, 1 or 2;
m is 0, 1, 2 or 3;
$R^4$ is selected from the group consisting of:
halo,
cyano,
hydroxy,
$C_{1-6}$-alkyl,
$C_{1-6}$-haloalkyl,
di($C_{1-6}$)alkylamino,
—CO(O)—$C_{1-6}$-alkyl,
$C_{1-6}$-alkoxy optionally substituted by one or more $R^a$,
$C_{3-10}$-cycloalkyl optionally substituted by one or more $R^a$,
4 to 10 membered heterocycloalkyl optionally substituted by one or more $R^a$,
aryl optionally substituted by one or more $R^a$,
5 to 10 membered heteroaryl optionally substituted by one or more $R^a$, and
—$NR^bR^c$,
wherein $R^a$, $R^b$ and $R^c$ are as defined hereinabove for formula (I) as well as pharmaceutically acceptable salts thereof.

Preferred compounds of formula (Ia) are the compounds wherein
each X is independently fluorine or chlorine;
n is 1;
m is 0, 1 or 2;
$R^4$ is selected from the group consisting of:
halo,
$C_{1-6}$-alkoxy optionally substituted by one or more $R^a$,
6 membered heterocycloalkyl optionally substituted by one or more $R^a$, and
5 to 6 membered heteroaryl optionally substituted by one or more $R^a$,
wherein $R^a$ is selected from
halo,
oxo,
hydroxyl and
$C_{1-6}$-alkyl,
as well as pharmaceutically acceptable salts thereof.

Especially preferred compounds of formula (Ia) are for example the following compounds:
3-Fluoro-N-trans(4-{2-[4-(6-fluoro-benzo[d]isoxazol-3-yl)-piperidin-1-yl]-ethyl}-cyclohexyl)-4-morpholin-4-yl-benzamide,
N-trans-(4-{2-[4-(6-Fluoro-benzo[d]isoxazol-3-yl)-piperidin-1-yl]-ethyl}-cyclohexyl)-4-methoxy-benzamide
4-tert-Butoxy-N-trans(4-{2-[4-(6-fluoro-benzo[d]isoxazol-3-yl)-piperidin-1-yl]-ethyl}-cyclohexyl)-benzamide,
4-Chloro-N-trans(4-{2-[4-(6-fluoro-benzo[d]isoxazol-3-yl)-piperidin-1-yl]-ethyl}-cyclohexyl)-benzamide,
N-trans(4-{2-[4-(6-Fluoro-benzo[d]isoxazol-3-yl)-piperidin-1-yl]-ethyl}-cyclohexyl)-4-pyrrol-1-yl-benzamide,
Benzo[1,3]dioxole-5-carboxylic acid trans(4-{2-[4-(5-fluoro-benzo[d]isoxazol-3-yl)-piperidin-1-yl]-ethyl}-cyclohexyl)-amide, and
Benzo[1,3]dioxole-5-carboxylic acid trans(4-{2-[4-(6-fluoro-benzo[d]isoxazol-3-yl)-piperidin-1-yl]-ethyl}-cyclohexyl)-amide.

Also encompassed by the compounds of formula (I) are the compounds of formula (Ib):

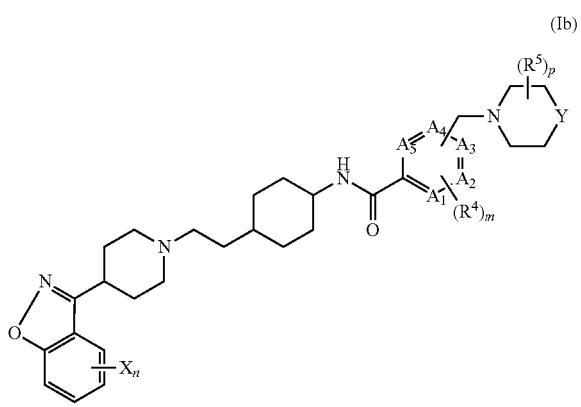

(Ib)

wherein
  each X is fluorine or chlorine;
  n is 0, 1 or 2;
  m and p are each independently 0, 1 or 2;
  $R^4$ and $R^5$ are each independently selected from the group consisting of:
    halo,
    cyano,
    hydroxy,
    $C_{1-6}$-alkyl,
    $C_{1-6}$-haloalkyl,
    —CO(O)—$C_{1-6}$-alkyl,
    $C_{1-6}$-alkoxy optionally substituted by one or more $R^a$,
    $C_{3-10}$-cycloalkyl optionally substituted by one or more $R^a$,
    4 to 10 membered heterocycloalkyl optionally substituted by one or more $R^a$,
    aryl optionally substituted by one or more $R^a$,
    5 to 10 membered heteroaryl optionally substituted by one or more $R^a$, and
    —$NR^bR^c$,
  wherein $R^a$, $R^b$ and $R^c$ are as defined in claim 1;
  Y is oxygen or —$SO_2$—;
  one, two or three of $A^1$, $A^2$, $A^3$, $A^4$ and $A^5$ are nitrogen and the others are $CR^6$, or $A^1$, $A^2$, $A^3$,
  $A^4$ and $A^5$ are $CR^6$ wherein
  each $R^6$ is independently hydrogen or $R^7$; and
  each $R^7$ is independently $C_{1-6}$alkyl, $C_{1-6}$alkyloxy, hydroxyl, amino, $C_{1-6}$alkylamino, N,N-di-($C_{1-6}$alkyl)-amino, halo, halo-$C_{1-6}$ alkyl, halo-$C_{1-6}$ alkoxy, hetero-$C_{1-6}$ alkyl, $C_{1-6}$ alkylsulfonyl, $C_{1-6}$alkylsulfanyl, or cyano;
as well as pharmaceutically acceptable salts thereof.

Preferred compounds of formula (Ib) are the compounds wherein
  X is fluorine;
  n and m are each independently 0 or 1;
  p is 0;
  $R^4$ is selected from the group consisting of:
    halo,
    cyano,
    hydroxy,
    $C_{1-6}$-alkyl, and
    $C_{1-6}$-haloalkyl,
  Y is oxygen or —$SO_2$—;
  one or two of $A^1$, $A^2$, $A^3$, $A^4$ and $A^5$ are nitrogen and the others are $CH_2$;
as well as pharmaceutically acceptable salts thereof.

Especially preferred compounds of formula (Ib) are for example the following compounds:
  N-trans-(4-{2-[4-(6-Fluoro-benzo[d]isoxazol-3-yl)-piperidin-1-yl]-ethyl}-cyclohexyl)-4-morpholin-4-yl-benzamide,
  N-trans(4-{2-[4-(5-Fluoro-benzo[d]isoxazol-3-yl)-piperidin-1-yl]-ethyl}-cyclohexyl)-4-morpholin-4-yl-benzamide,
  N-Trans (4-{2-[4-(6-Fluoro-benzo[d]isoxazol-3-yl)-piperidin-1-yl]-ethyl}-cyclohexyl)-6-morpholin-4-yl-nicotinamide,
  5-Morpholin-4-yl-pyrazine-2-carboxylic acid trans(4-{2-[4-(6-fluoro-benzo[d]isoxazol-3-yl)-piperidin-1-yl]-ethyl}-cyclohexyl)-amide,
  6-Morpholin-4-yl-pyridazine-3-carboxylic acid-trans(4-{2-[4-(6-fluoro-benzo[d]isoxazol-3-yl)-piperidin-1-yl]-ethyl}-cyclohexyl)-amide,
  2-Morpholin-4-yl-pyrimidine-5-carboxylic acid trans(4-{2-[4-(6-fluoro-benzo[d]isoxazol-3-yl)-piperidin-1-yl]-ethyl}-cyclohexyl)-amide,
  3-Fluoro-N-trans(4-{2-[4-(6-fluoro-benzo[d]isoxazol-3-yl)-piperidin-1-yl]-ethyl}-cyclohexyl)-4-morpholin-4-yl-benzamide,
  4-(1,1-Dioxo-1,6-thiomorpholin-4-yl)-N-trans(4-{2-[4-(6-fluoro-benzo[d]isoxazol-3-yl)-piperidin-1-yl]-ethyl}-cyclohexyl)-benzamide,
  N-trans(4-{2-[4-(6-Fluoro-benzo[d]isoxazol-3-yl)-piperidin-1-yl]-ethyl}-cyclohexyl)-2-morpholin-4-yl-isonicotinamide,
  N-trans(4-{2-[4-(6-Fluoro-benzo[d]isoxazol-3-yl)-piperidin-1-yl]-ethyl}-cyclohexyl)-4-piperidin-1-yl-benzamide,
  N-trans(4-{2-[4-(5-Fluoro-benzo[d]isoxazol-3-yl)-piperidin-1-yl]-ethyl}-cyclohexyl)-4-piperidin-1-yl-benzamide,
  4-(2,6-Dimethyl-morpholin-4-yl)-N-trans(4-{2-[4-(5-fluoro-benzo[d]isoxazol-3-yl)-piperidin-1-yl]-ethyl}-cyclohexyl)-benzamide,
  4-(2,6-Dimethyl-morpholin-4-yl)-N-trans(4-{2-[4-(6-fluoro-benzo[d]isoxazol-3-yl)-piperidin-1-yl]-ethyl}-cyclohexyl)-benzamide, and
  4-(1,1-Dioxo-1,6,4-thiomorpholin-4-yl)-N trans-(4-{2-[4-(5-fluoro-benzo[d]isoxazol-3-yl)-piperidin-1-yl]-ethyl}-cyclohexyl)-benzamide.

Also encompassed by the compounds of formula (I) are the compounds of formula (Ic):

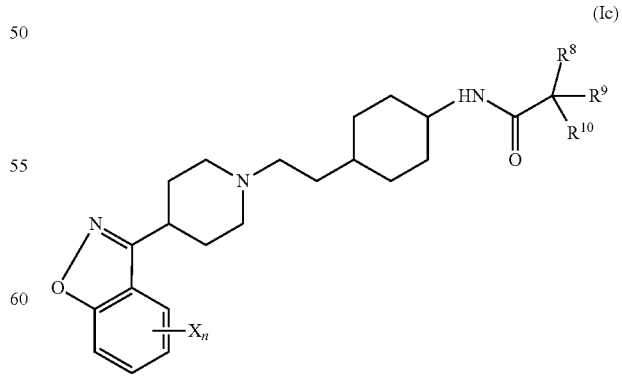

(Ic)

wherein
  each X is independently fluorine or chlorine;
  n is 0, 1 or 2;

$R^8$ and $R^9$ form a 3-, 4-, 5-, or 6-membered saturated ring, optionally comprising one or two heteroatoms selected from oxygen and nitrogen;

$R^{10}$ can be a substituent on the ring formed by $R^8$ and $R^9$ and is selected from the group consisting of
halogen,
cyano,
hydroxy,
$C_{1-6}$-alkyl,
$C_{1-6}$-haloalkyl and
$C_{1-6}$-alkoxy;

as well as pharmaceutically acceptable salts thereof.

Also encompassed by the compounds of formula (I) are the compounds of formula (Id):

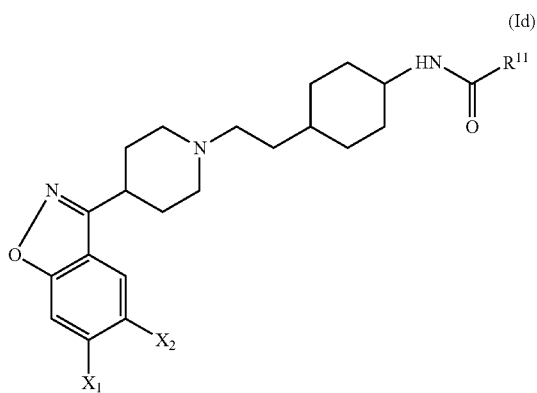

(Id)

wherein
$X_1$=H and $X_2$=fluoro or chloro; or
$X_2$=H and $X_1$=fluoro or chloro; and
$R^{11}$ is selected from the group consisting of $C_{1-6}$-alkyl and $C_{1-6}$-alkoxy, each of which is optionally substituted by halogen, hydroxy, $C_{1-6}$-alkyl, $C_{1-6}$-haloalkyl, $C_{1-6}$-alkoxy or $C_{5-6}$-cycloalkyl which is optionally substituted by $C_{1-6}$-alkyl or $C_{1-6}$-alkoxy;

as well as pharmaceutically acceptable salts thereof.

Special preference is given to the compounds of formula (Id'):

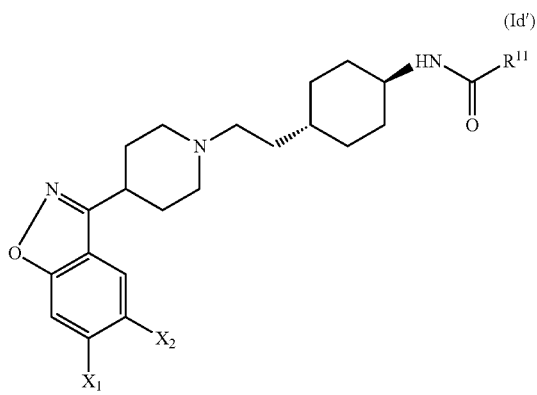

(Id')

wherein $X_1$, $X_2$, and $R^{11}$ are as defined hereinabove for formula (Id) as well as pharmaceutically acceptable salts thereof.

Especially preferred compounds of formula (Id') are for example the following compounds:

4N-trans(4-{2-[4-(6-Fluoro-benzo[d]isoxazol-3-yl)-piperidin-1-yl]-ethyl}-cyclohexyl)-acetamide, Tetrahydro-pyran-4-carboxylic acid trans(4-{2-[4-(6-fluoro-benzo[d]isoxazol-3-yl)-piperidin-1-yl]-ethyl}-cyclohexyl)-amide, N-trans(4-{2-[4-(6-Fluoro-benzo[d]isoxazol-3-yl)-piperidin-1-yl]-ethyl}-cyclohexyl)-3-methoxy-propionamide, N-trans(4-{2-[4-(5-Fluoro-benzo[d]isoxazol-3-yl)-piperidin-1-yl]-ethyl}-cyclohexyl)-acetamide, N-trans(4-{2-[4-(5-Fluoro-benzo[d]isoxazol-3-yl)-piperidin-1-yl]-ethyl}-cyclohexyl)-3-methoxy-propionamide, Trans 4-{2-[4-(6-Fluoro-benzo[d]isoxazol-3-yl)-piperidin-1-yl]-ethyl}-cyclohexylamine, 2,3-Dihydro-benzo[1,4]dioxine-2-carboxylic acid trans(4-{2-[4-(6-fluoro-benzo[d]isoxazol-3-yl)-piperidin-1-yl]-ethyl}-cyclohexyl)-amide, N-trans(4-{2-[4-(6-Fluoro-benzo[d]isoxazol-3-yl)-piperidin-1-yl]-ethyl}-cyclohexyl)-2-(3-methyl-pyrazol-1-yl)-acetamide, 3,3,3-Trifluoro-N-trans(4-{2-[4-(6-fluoro-benzo[d]isoxazol-3-yl)-piperidin-1-yl]-ethyl}-cyclohexyl)-propionamide, 2-(3,5-Dimethoxy-phenyl)-N-trans(4-{2-[4-(6-fluoro-benzo[d]isoxazol-3-yl)-piperidin-1-yl]-ethyl}-cyclohexyl)-acetamide, N-trans(4-{2-[4-(6-Chloro-benzo[d]isoxazol-3-yl)-piperidin-1-yl]-ethyl}-cyclohexyl)-3-methoxy-propionamide, N-trans(4-{2-[4-(6-Chloro-benzo[d]isoxazol-3-yl)-piperidin-1-yl]-ethyl}-cyclohexyl)-acetamide, N-trans-(4-{2-[4-(6-Chloro-benzo[d]isoxazol-3-yl)-piperidin-1-yl]-ethyl}-cyclohexyl)-3,3,3-trifluoro-2-hydroxy-propionamide, N-trans(4-{2-[4-(6-Chloro-benzo[d]isoxazol-3-yl)-piperidin-1-yl]-ethyl}-cyclohexyl)-2-(tetrahydro-pyran-2-yl)-acetamide, N-trans-(4-{2-[4-(6-Chloro-benzo[d]isoxazol-3-yl)-piperidin-1-yl]-ethyl}-cyclohexyl)-2-trans (4-methoxy-cyclohexyl)-acetamide, N-trans(4-{2-[4-(6-Chloro-benzo[d]isoxazol-3-yl)-piperidin-1-yl]-ethyl}-cyclohexyl)-2-(1,4-dioxa-spiro[4.5]dec-8-yl)-acetamide, and N-trans-(4-{2-[4-(6-Chloro-benzo[d]isoxazol-3-yl)-piperidin-1-yl]-ethyl}-cyclohexyl)-3,3-dimethoxy-propionamide.

Also encompassed by the compounds of formula (I) are the compounds of formula (Ie):

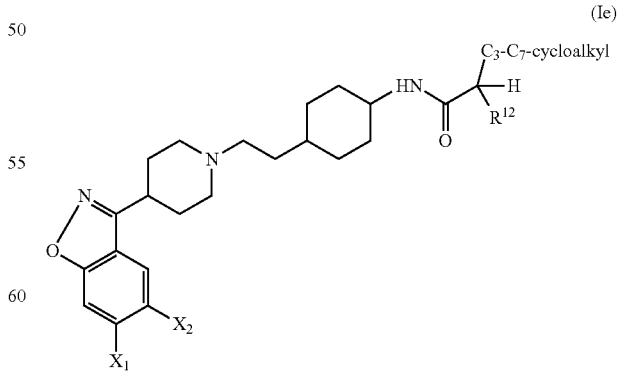

(Ie)

wherein
$X_1$=H and $X_2$=fluoro or chloro; or
$X_2$=H and $X_1$=fluoro or chloro; and $R^{12}$ is selected from the group consisting of
halo,
hydroxy,
cyano,
$C_{1-6}$-alkyl,
$C_{1-6}$-haloalkyl and
$C_{1-6}$-alkoxy;
as well as pharmaceutically acceptable salts thereof.

Special preference is given to the compounds of formula (Ie'):

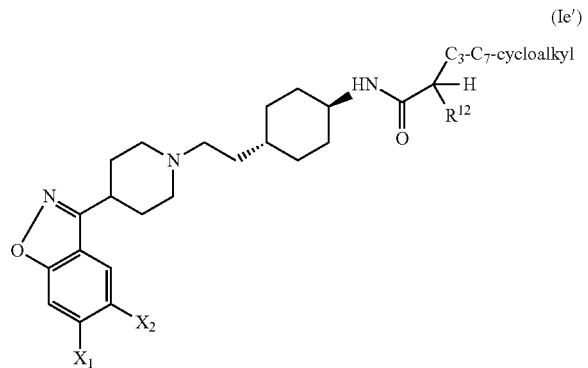

wherein $X_1$, $X_2$, and $R^{12}$ are as defined hereinabove for formula (Ie) as well as pharmaceutically acceptable salts thereof.

Especially preferred compounds of formula (Ie') are for example the following compounds:
1-Hydroxy-cyclopropanecarboxylic acid trans(4-{2-[4-(6-fluoro-benzo[d]isoxazol-3-yl)-piperidin-1-yl]-ethyl}-cyclohexyl)-amide, and
1-Trifluoromethyl-cyclobutanecarboxylic acid trans(4-{2-[4-(6-fluoro-benzo[d]isoxazol-3-yl)-piperidin-1-yl]-ethyl}-cyclohexyl)-amide.

Also encompassed by the compounds of formula (I) are the compounds of formula (Ig):

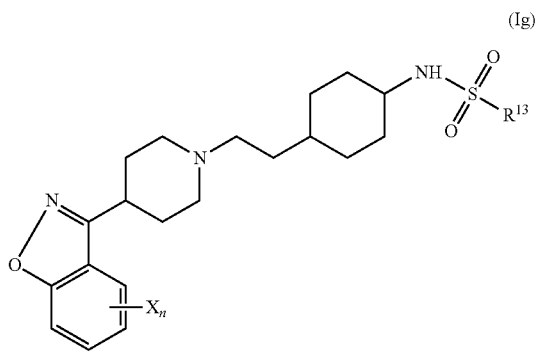

wherein
each X is independently fluorine or chlorine;
n is 0, 1 or 2;
$R^{13}$ is selected from the group consisting of
$C_{1-6}$-alkyl,
$C_{1-6}$-haloalkyl,
$C_{1-6}$-alkoxy,
aryl optionally substituted by one or more $R^a$, and
5 to 10 membered heteroaryl optionally substituted by one or more $R^a$;
$R^a$ is halo, $C_{1-6}$-alkyl or $C_{1-6}$-alkoxy;
as well as pharmaceutically acceptable salts thereof.

Especially preferred compounds of formula (Ig) are for example the following compounds:
Ethanesulfonic acid (4-trans {2-[4-(6-fluoro-benzo[d]isoxazol-3-yl)-piperidin-1-yl]-ethyl}-cyclohexyl)-amide,
4-Chloro-N-trans(4-{2-[4-(6-fluoro-benzo[d]isoxazol-3-yl)-piperidin-1-yl]-ethyl}-cyclohexyl)-benzenesulfonamide,
N-trans(4-{2-[4-(6-Fluoro-benzo[d]isoxazol-3-yl)-piperidin-1-yl]-ethyl}-cyclohexyl)-4-methoxy-benzenesulfonamide, and
Pyridine-3-sulfonic acid trans(4-{2-[4-(6-fluoro-benzo[d]isoxazol-3-yl)-piperidin-1-yl]-ethyl}-cyclohexyl)-amide.

Special preference is also given to the following compounds:
N-trans-(4-{2-[4-(6-Chloro-benzo[d]isoxazol-3-yl)-piperidin-1-yl]-ethyl}-cyclohexyl)-3-cyano-propionamide,
N-trans-(4-{2-[4-(6-Chloro-benzo[d]isoxazol-3-yl)-piperidin-1-yl]-ethyl}-cyclohexyl)-2-cyano-acetamide,
N-trans-(4-{2-[4-(6-Chloro-benzo[d]isoxazol-3-yl)-piperidin-1-yl]-ethyl}-cyclohexyl)-2-(R)-tetrahydro-furan-2-yl-acetamide,
N-trans-(4-{2-[4-(6-Chloro-benzo[d]isoxazol-3-yl)-piperidin-1-yl]-ethyl}-cyclohexyl)-2-cyclopropyl-acetamide,
N-trans-(4-{2-[4-(6-Chloro-benzo[d]isoxazol-3-yl)-piperidin-1-yl]-ethyl}-cyclohexyl)-2-hydroxy-acetamide,
N-trans-(4-{2-[4-(6-Chloro-benzo[d]isoxazol-3-yl)-piperidin-1-yl]-ethyl}-cyclohexyl)-2-methanesulfonyl-acetamide,
N-trans-(4-{2-[4-(6-Chloro-benzo[d]isoxazol-3-yl)-piperidin-1-yl]-ethyl}-cyclohexyl)-2-[1,3]dioxan-2-yl-acetamide,
N-trans-(4-{2-[4-(5-Chloro-benzo[d]isoxazol-3-yl)-piperidin-1-yl]-ethyl}-cyclohexyl)-2-(4-methoxy-cyclohexyl)-acetamide,
N-trans-(4-{2-[4-(5-Fluoro-benzo[d]isoxazol-3-yl)-piperidin-1-yl]-ethyl}-cyclohexyl)-methanesulfonamide,
N-trans-(4-{2-[4-(6-Chloro-5-fluoro-benzo[d]isoxazol-3-yl)-piperidin-1-yl]-ethyl}-cyclohexyl)-3-methoxy-propionamide,
N-trans-(4-{2-[4-(6-Chloro-5-fluoro-benzo[d]isoxazol-3-yl)-piperidin-1-yl]-ethyl}-cyclohexyl)-2-(tetrahydro-furan-2-yl)-acetamide,
N-trans-(4-{2-[4-(5,6-Difluoro-benzo[d]isoxazol-3-yl)-piperidin-1-yl]-ethyl}-cyclohexyl)-2-methoxy-acetamide,
N-trans-(4-{2-[4-(5,6-Difluoro-benzo[d]isoxazol-3-yl)-piperidin-1-yl]-ethyl}-cyclohexyl)-2-((1R,3R)-3-methoxy-cyclopentyl)-acetamide,
N-trans-(4-{2-[4-(5,6-Difluoro-benzo[d]isoxazol-3-yl)-piperidin-1-yl]-ethyl}-cyclohexyl)-2-(4-methoxy-cyclohexyl)-acetamide,
N-trans-(4-{2-[4-(5,6-Difluoro-benzo[d]isoxazol-3-yl)-piperidin-1-yl]-ethyl}-cyclohexyl)-3-methoxy-propionamide,
N-trans-(4-{2-[4-(5,6-Difluoro-benzo[d]isoxazol-3-yl)-piperidin-1-yl]-ethyl}-cyclohexyl)-acetamide,
N-trans-(4-{2-[4-(5,6-Difluoro-benzo[d]isoxazol-3-yl)-piperidin-1-yl]-ethyl}-cyclohexyl)-2-hydroxy-acetamide,
N-trans-(4-{2-[4-(5,6-Difluoro-benzo[d]isoxazol-3-yl)-piperidin-1-yl]-ethyl}-cyclohexyl)-3-hydroxy-propionamide,
N-trans-(4-{2-[4-(5,6-Difluoro-benzo[d]isoxazol-3-yl)-piperidin-1-yl]-ethyl}-cyclohexyl)-2-(4-hydroxy-cyclohexyl)-acetamide,
N-trans-(4-{2-[4-(5,6-Difluoro-benzo[d]isoxazol-3-yl)-piperidin-1-yl]-ethyl}-cyclohexyl)-2-((1R,3R)-3-hydroxy-cyclopentyl)-acetamide, Tetrahydro-pyran-4-carboxylic acid trans-(4-{2-[4-(5,6-difluoro-benzo[d]isoxazol-3-yl)-piperidin-1-yl]-ethyl}-cyclohexyl)-amide,
N-trans-(4-{2-[4-(5,6-Difluoro-benzo[d]isoxazol-3-yl)-piperidin-1-yl]-ethyl}-cyclohexyl)-2-[1,3]dioxan-2-yl-acetamide, and
N-trans-(4-{2-[4-(6-Methyl-benzo[d]isoxazol-3-yl)-piperidin-1-yl]-ethyl}-cyclohexyl)-acetamide.

A further aspect of the present invention relates to pharmaceutical compositions containing the compounds of formulae (I), (Ia), (Ib), (Ic), (Id) (Id'), (Ie), (Ie') and (Ig) and a pharmaceutically acceptable carrier.

In a further aspect the present invention provides processes for the manufacture of compounds of formula (I) as defined above.

The preparation of compounds of formula (I) of the present invention can be carried out in sequential or convergent synthetic routes. Syntheses of the invention are shown in the following schemes. The skills required for carrying out the reaction and purification of the resulting products are known to those skilled in the art. The substituents and indices used in the following description of the processes have the significance given herein before unless indicated to the contrary.

In more detail, the compounds of formula (I) can be manufactured by the methods given below, by the methods given in the examples or by analogous methods. Appropriate reaction conditions for the individual reaction steps are known to a person skilled in the art. Starting materials are either commercially available or can be prepared by methods analogous to the methods given below, by methods described in references cited in the description or in the examples, or by methods known in the art.

Scheme 1

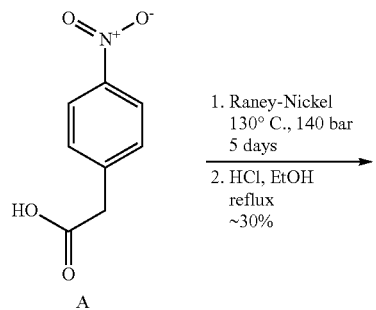

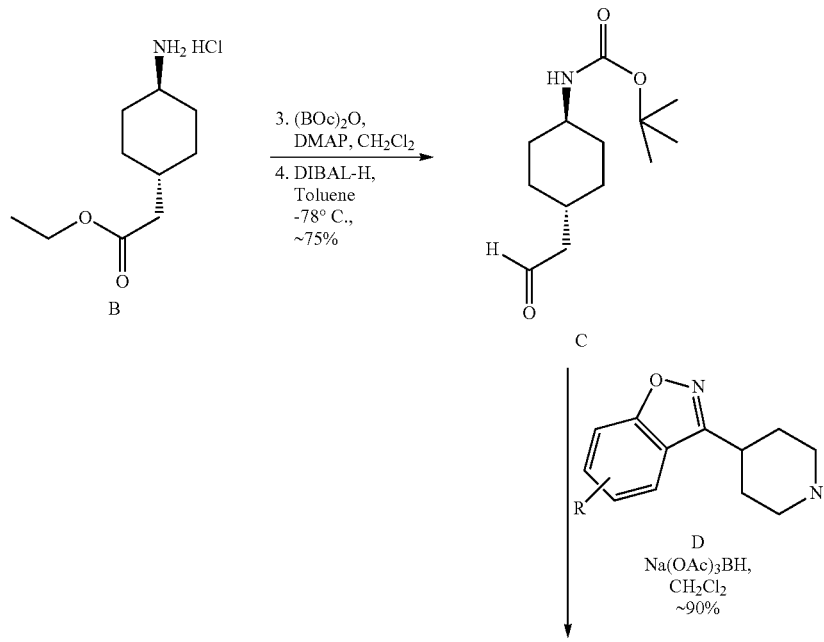

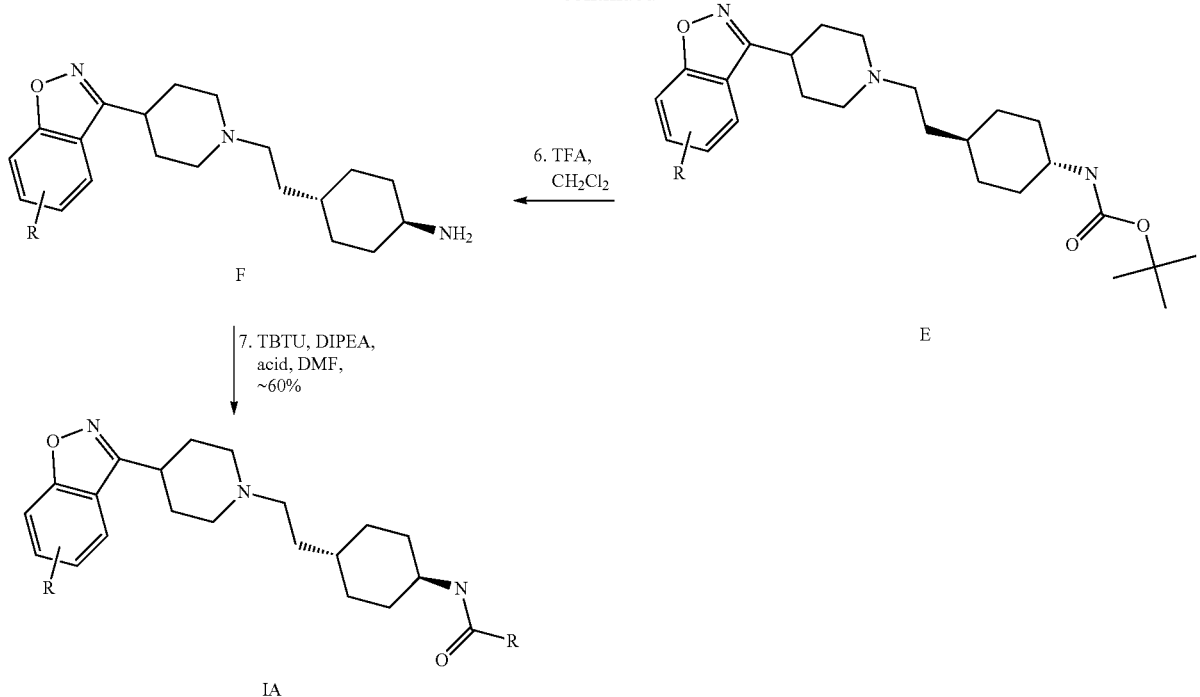

4-(benzo-isoxazol-3-yl)-piperidin-1-yl trans-ethyl-cyclohexyl-amides or trans-1,4-cyclohexyl ethyl derivates of formula IA can be prepared as depicted in scheme 1 starting from 4-nitro-phenylacetic acid that was hydrogenated using raney nickel as a catalyst. The hydrogenation with nickel leads preferentially to the desired trans-isomer (according to Journal of Medicinal Chemistry, 1998, 41, 760-771). The ethyl ester can be prepared according to methods known to those skilled in the art and described in the mentioned literature (e.g by treatment with ethanol on the presence of an acid such as HCl). The HCl salt can be crystallized and then the cis/trans mixture can be resolved into the pure trans amino ester chloride B. Reaction with a protecting group such as tert-butyl dicarbonate in the presence of a base, like triethylamine, and a catalyst, like dimethylaminopyridine, and reduction with diisobutylaluminium hydride (DIBAL-H) in an appropriate solvent, e.g. toluene at −78° C. gave the aldehyde C which can be used without purification in the next step. Reductive amination of aldehyde C with a substituted 4-(benzo[d]isoxazol-3-yl)-piperidine D can be performed using methods described in the literature, by methods described herein or by methods known in the art. The reductive amination can take place in the presence of a solvent, like 1,2-Dichloromethane, and/or a reducing agent, such as sodium triacetoxy borohydride, to yield intermediate E. Removal of the Boc protective group under acidic conditions, such as trifluoroacetic acid, in a suitable solvent, e.g. THF, yields the trans-amino cyclohexyl ethyl intermediate F (usually the TFA salt). The coupling of the amine intermediate F with carboxylic acids (either commercially available or accessible by methods described in references or by methods known in the art) is widely described in literature (e.g. Comprehensive Organic Transformations: A Guide to Functional Group Preparations, 2nd Edition, Richard C. Larock. John Wiley & Sons, New York, N.Y. 1999) and can be accomplished by employing coupling reagents such as, e.g. N,N-carbonyldiimidazole (CDI), 1-hydroxy-1,2,3-benzotriazole (HOBT) or O-benzotriazol-1-yl-N,N,N,N-tetramethyluronium tetrafluoroborate (TBTU) in a suitable solvent, e.g. dimethylformamide (DMF) or dioxane, in the presence of a base (e.g. triethylamine or diisopropylethylamine) to yield compounds of formula IA. In other cases an acid chloride can also be used in the presence of a base (e.g. triethylamine or diisopropylethylamine) in a solvent, like dichloromethane.

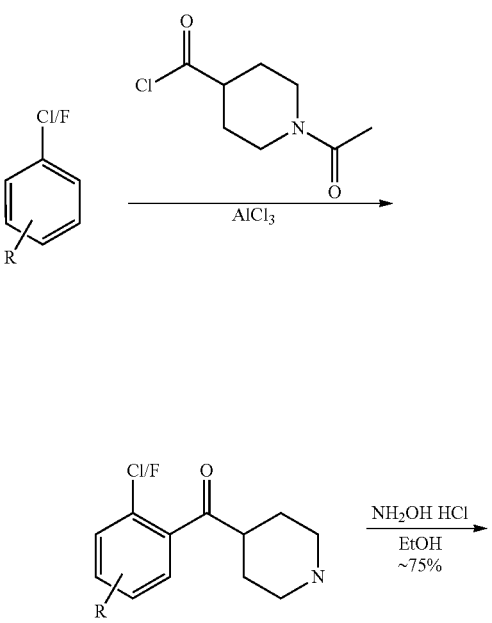

Scheme 2A

-continued

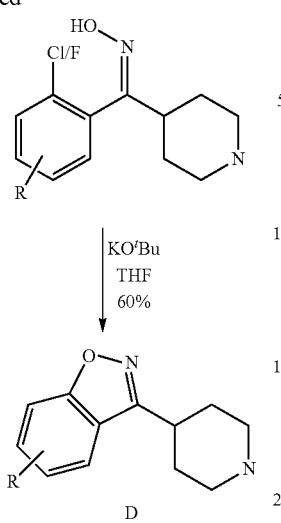

Some substituted 4-(benzo[d]isoxazol-3-yl)-piperidines of formula D can be obtained by Friedel-Crafts acylation of an adequate benzene derivative using an appropriate Lewis acid, like aluminium chloride, in the presence of 1-acetylisonipecotoyl chloride in a solvent, like dichlorobenzene, by heating to a temperature of about 70° C. as described in Journal of Medicinal Chemistry, 1985, 28, 761-769; Journal of Medicinal Chemistry, 1970, 13, 1-6; or U.S. Pat. No. 4,355,037.

Scheme 2B

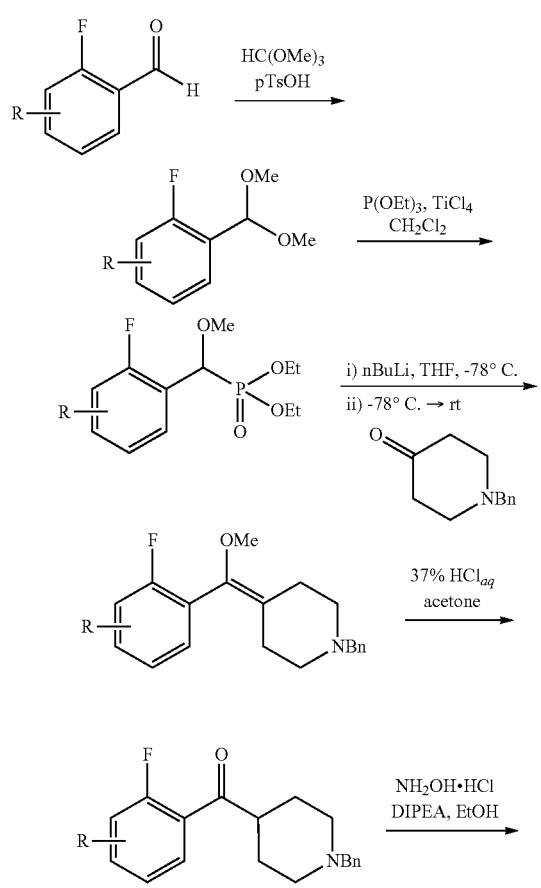

-continued

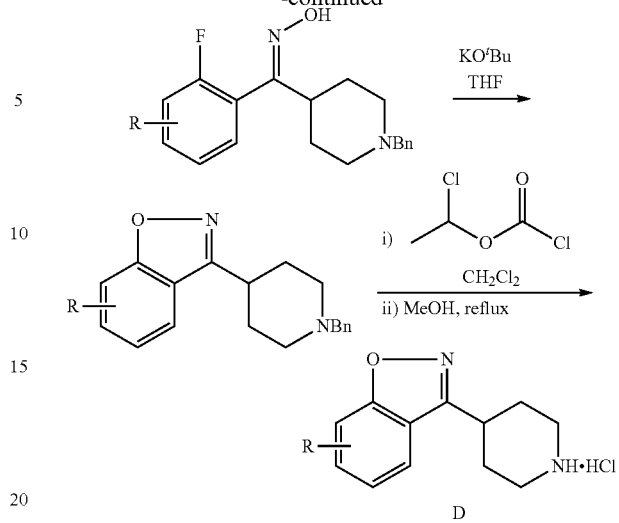

Alternatively 4-(benzo[d]isoxazol-3-yl)-piperidines of formula D can be obtained starting from an appropriately substituted benzaldehyde containing a leaving group such as for example F in the ortho position (in analogy to WO02066446). The benzaldehyde can be converted to a dimethyl acetal with a reagent, such as trimethyl orthoformiate, in the presence a catalytic amount of an acid, such as pTsOH. Reaction of the acetal with triethylorthophosphite in presence of a Lewis acid, such as $TiCl_4$, in a solvent, such as $CH_2Cl_2$, leads to a phosphonate that can be deprotonated with a base, such as nBuLi, in a solvent, like THF, and reacted with 1-benzyl-piperidin-4-one to obtain an enol ether as depicted in Scheme 2B. Treatment of the enol ether with an acid, such as concentrated aqueous HCl, in a solvent, such as acetone, yields the corresponding ketone. Reaction of the ketone with $NH_2OH·HCl$ in the presence of a base, such as DIPEA, in a solvent, like EtOH, followed by deprotonation of the oxime with a base, such as $KO^tBu$, in THF and intramolecular cyclization leads to the benzo[d]isoxazole derivative. The 4-(benzo[d]isoxazol-3-yl)-piperidines of formula D are then obtained by debenzylation employing methods known in the art, for example reaction with α-chloroethyl chloroformate and subsequent treatment with refluxing MeOH.

Scheme 3

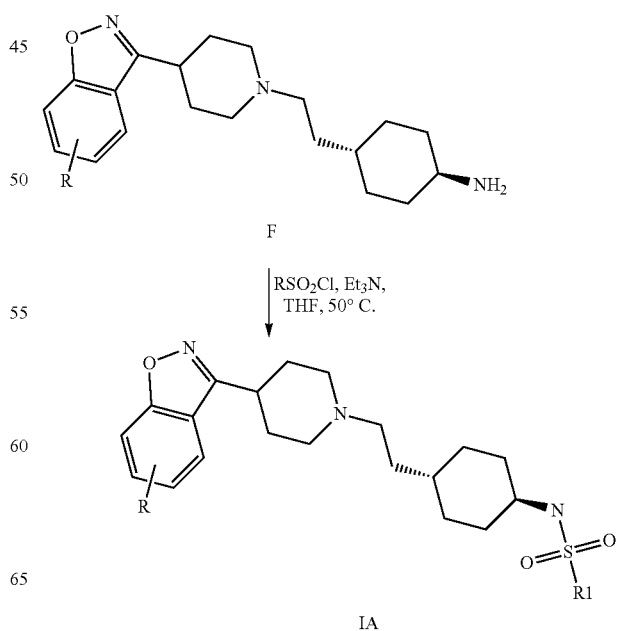

In other examples the intermediate F can also react with a sulfonyl chloride in the present of a base, like triethylamine, to give the corresponding sulfonyl derivative of the formula IA.

The ability of the compounds to bind to the 5-$HT_{2A}$, $D_3$ and $D_2$ receptors was determined using radioligand binding to cloned receptors selectively expressed in HEK-293 EBNA cells.

Membrane Preparation for Human $D_2$, Human $D_3$ and Human 5-$HT_{2A}$ Receptors HEK-293 EBNA cells were transiently transfected with expression plasmids encoding for the human $D_2$ or $D_3$ dopamine- or for the human 5-$HT_{2A}$ serotonin receptor, respectively. The cells were harvested 48 h post-transfection, washed three times with cold PBS and stored at −80° C. prior to use. The pellet was suspended in cold 50 mM Tris-HCl buffer containing 10 mM EDTA (pH 7.4) and homogenized with a Polytron (Kinematica AG, Basel, Switzerland) for 20-30 sec at 12,000 rpm. After centrifugation at 48,000×g for 30 min at 4° C., the pellet was resuspended in cold 10 mM Tris-HCl buffer containing 0.1 mM EDTA (pH 7.4), homogenized, and centrifuged as above. This pellet was further resuspended in a smaller volume of ice cold 10 mM Tris-HCl buffer containing 0.1 mM EDTA (pH 7.4) and homogenized with a Polytron for 20-30 sec at 12,000 rpm. The protein content of this homogenate was determined with the Bio-Rad (Bradford) Protein Assay (Biorad Laboratories GmbH, München, Germany) according to the instructions of the manufacturer using gamma globulin as the standard. This homogenate was stored at −80° C. in aliquots and thawed immediately prior to use.

Radioligand Binding Assay Conditions

Aliquots of membrane preparations were thawed at RT, resuspended in assay buffer ($D_2$, $D_3$: 50 mM Tris-HCl, 120 mM NaCl, 5 mM $MgCl_2$, 1 mM EDTA, 5 mM KCl, 1.5 mM $CaCl_2$, pH=7.4; 5-HT2A: 50 mM Tris-HCl, 10 mM $MgCl_2$, 1 mM EGTA, pH=7.4), homogenized with a Polytron for 20-30 sec at 12,000 rpm and adjusted to a final concentration of approximately 7.5 µg protein/well ($D_2$, $D_3$) and 15 µg protein/well (5-HT2A), respectively.

The binding affinity (Ki) of the compounds was determined using radioligand binding. Membranes were incubated in a total volume of 200 µl with a fixed concentration of radioligand (final concentration approximately 0.7 nM [$^3$H]-spiperone for $D_2$, 0.5 nM [$^3$H]-spiperone for $D_3$, and 1.1 nM [$^3$H]-ketanserin for 5-$HT_{2A}$) and ten concentrations of test compound in ranging between 10 µM-0.1 nM for 1 h at RT. At the end of the incubation, the reaction mixtures were filtered on to unifilter 96-well white microplates with bonded GF/C filters (Packard BioScience, Zürich, Switzerland; preincubated for 1 h in 0.1% polyethylenimine (PEI) in assay buffer) with a Filtermate 196 harvester (Packard BioScience) and washed 3 times with cold assay buffer. The nonspecific binding was determined with equally composed reaction mixtures in the presence of 10 µM unlabelled spiperone. Per well 45 µl of Microscint 40 (Perkin Elmer, Schwerzenbach, Switzerland) was added, plates for sealed, shaken for 20 min and counted for 3 min on a Topcount Microplate Scintillation Counter (Canberra Packard SA, Zürich, Switzerland) with quenching correction.

Data Calculation

The CPM value for each duplicate of a concentration of competing compound was averaged (y1), then the % specific binding was calculated according to the equation (((y1−nonspecific)/(total binding−non-specific))×100). Graphs were plotted with the % specific binding using XLfit, a curve fitting program that iteratively plots the data using Levenburg Marquardt algorithm. The single site competition analysis equation used was y=A+((B−A)/(1+((x/C)$^D$))), where y is the % specific binding, A is the minimum y, B is the maximum y, C is the $IC_{50}$, x is the $\log_{10}$ of the concentration of the competing compound and D is the slope of the curve (the Hill Coefficient). From these curves the $IC_{50}$ (inhibition concentration at which 50% specific binding of the radioligand was displaced) and Hill coefficient were determined. The affinity constant (Ki) was calculated using the Cheng-Prusoff equation Ki=($IC_{50}$/1+([L]/Kd), where [L] is the concentration of radioligand and Kd is the dissociation constant of the radioligand at the receptor as determined by the saturation isotherm.

The compounds of the present invention are selective dual modulators of the serotonin 5-$HT_{2a}$ and dopamine $D_3$ receptors as shown in the activity table hereinafter which gives the Ki values in µM for the serotonin 5-$HT_{2a}$, dopamine $D_3$ and dopamine $D_2$ receptors for some examples of the compounds of the present invention:

Activity table

| Ex. | Compound | Name | Ki 5-$HT_{2a}$: Human (5HT2a) | Ki dopamine d3 receptor: human (D3) |
|---|---|---|---|---|
| 1 | 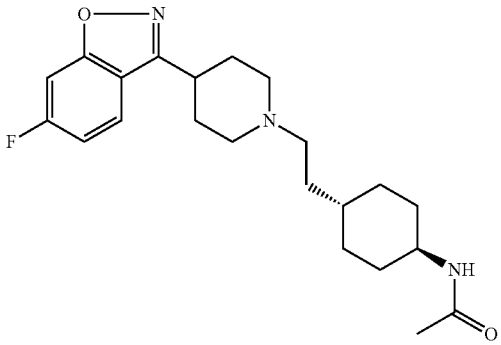 [SMILES: CC(=O)N[C@H]1CC[C@H](CCN2CCC(c3noc4cc(F)ccc34)CC2)CC1] | 4N-trans(4-{2-[4-(6-Fluoro-benzo[d]isoxazol-3-yl)-piperidin-1-yl]-ethyl}-cyclohexyl)-acetamide | 0.002224 | 0.004964 |

-continued

Activity table

| Ex. | Compound | Name | Ki 5-HT$_{2a}$: Human (5HT2a) | Ki dopamine d3 receptor: human (D3) |
|---|---|---|---|---|
| 2 | | Tetrahydro-pyran-4-carboxylic acid trans (4-{2-[4-(6-fluoro-benzo[d]isoxazol-3-yl)-piperidin-1-yl]-ethyl}-cyclohexyl)-amide | 0.001739 | 0.009744 |
| 3 | | N-trans (4-{2-[4-(6-Fluoro-benzo[d]isoxazol-3-yl)-piperidin-1-yl]-ethyl}-cyclohexyl)-3-methoxy-propionamide | 0.001809 | 0.004749 |
| 4 | | N-trans-(4-{2-[4-(6-Fluoro-benzo[d]isoxazol-3-yl)-piperidin-1-yl]-ethyl}-cyclohexyl)-4-morpholin-4-yl-benzamide | 0.009519 | 0.028161 |

Activity table

| Ex. | Compound | Name | Ki 5-HT$_{2a}$: Human (5HT2a) | Ki dopamine d3 receptor: human (D3) |
|---|---|---|---|---|
| 4A | | N-Trans (4-{2-[4-(6-Fluoro-benzo[d]isoxazol-3-yl)-piperidin-1-yl]-ethyl}-cyclohexyl)-6-morpholin-4-yl-nicotinamide | 0.002701 | 0.007948 |
| 4B | | 5-Morpholin-4-yl-pyrazine-2-carboxylic acid trans (4-{2-[4-(6-fluoro-benzo[isoxazol-3-yl)-piperidin-1-yl]-ethyl}-cyclohexyl)-amide | 0.00381 | 0.019443 |
| 4C | | 6-Morpholin-4-yl-pyridazine-3-carboxylic acid-trans (4-{2-[4-(6-fluoro-benzo[d]isoxazol-3-yl)-piperidin-1-yl]-ethyl}-cyclohexyl)-amide | 0.003181 | 0.025326 |

-continued

Activity table

| Ex. | Compound | Name | Ki 5-HT$_{2a}$: Human (5HT2a) | Ki dopamine d3 receptor: human (D3) |
|---|---|---|---|---|
| 4D | | 2-Morpholin-4-yl-pyrimidine-5-carboxylic acid trans (4-{2-[4-(6-fluoro-benzo[d]isoxazol-3-yl)-piperidin-1-yl]-ethyl}-cyclohexyl)-amide | 0.002453 | 0.01534 |
| 5 | | 3-Fluoro-N-trans (4-{2-[4-(6-fluoro-benzo[d]isoxazol-3-yl)-piperidin-1-yl]-ethyl}-cyclohexyl)-4-morpholin-4-yl-benzamide | 0.01746 | 0.045277 |
| 6 | | 3-Fluoro-N-trans (4-{2-[4-(6-fluoro-benzo[d]isoxazol-3-yl)-piperidin-1-yl]-ethyl}-cyclohexyl)-4-morpholin-4-yl-benzamide | 0.011383 | 0.01152 |

-continued

Activity table

| Ex. | Compound | Name | Ki 5-HT$_{2a}$: Human (5HT2a) | Ki dopamine d3 receptor: human (D3) |
|---|---|---|---|---|
| 7 | | Trans 4-{2-[4-(6-Fluoro-benzo[d]isoxazol-3-yl)-piperidin-1-yl]-ethyl}-cyclohexylamine (could be obtained as the trifluoroacetic acid salt) and 3,4-(methylenedioxy) phenylacetic acid | 0.002087 | 0.004015 |
| 8 | | N-trans-(4-{2-[4-(6-Fluoro-benzo[d]isoxazol-3-yl)-piperidin-1-yl]-ethyl}-cyclohexyl)-4-methoxy-benzamide | 0.003654 | 0.004525 |
| 9 | | 4-tert-Butoxy-N-trans (4-{2-[4-(6-fluoro-benzo[d]isoxazol-3-yl)-piperidin-1-yl]-ethyl}-cyclohexyl)-benzamide | 0.001724 | 0.003417 |

-continued

Activity table

| Ex. | Compound | Name | Ki 5-HT$_{2a}$: Human (5HT2a) | Ki dopamine d3 receptor: human (D3) |
|---|---|---|---|---|
| 10 | | 4-Chloro-N-trans (4-{2-[4-(6-fluoro-benzo[d]isoxazol-3-yl)-piperidin-1-yl]-ethyl}-cyclohexyl)-benzamide | 0.002666 | 0.003498 |
| 11 | | 4-(1,1-Dioxo-1,6-thiomorpholin-4-yl)-N-trans (4-{2-[4-(6-fluoro-benzo[d]isoxazol-3-yl)-piperidin-1-yl]-ethyl}-cyclohexyl)-benzamide | 0.002483 | 0.004674 |
| 12 | | N-trans (4-{2-[4-(6-Fluoro-benzo[d]isoxazol-3-yl)-piperidin-1-yl]-ethyl-cyclohexyl)-2-morpholin-4-yl-isonicotinamide | 0.002459 | 0.005747 |

-continued

| | | Activity table | | |
|---|---|---|---|---|
| Ex. | Compound | Name | Ki 5-HT$_{2a}$: Human (5HT2a) | Ki dopamine d3 receptor: human (D3) |
| 13 | | N-trans (4-{2-[4-(6-Fluoro-benzo[d]isoxazol-3-yl)-piperidin-1-yl]-ethyl}-cyclohexyl)-2-methoxy-isonicotinamide | 0.001623 | 0.003738 |
| 14 | | N-trans (4-{2-[4-(6-Fluoro-benzo[d]isoxazol-3-yl)-piperidin-1-yl]-ethyl}-cyclohexyl)-4-piperidin-1-yl-benzamide | 0.002598 | 0.008685 |
| 15 | | 2,3-Dihydro-benzo[1,4]dioxine-2-carboxylic acid trans (4-{2-[4-(6-fluoro-benzo[d]isoxazol-3-yl)-piperidin-1-yl]-ethyl}-cyclohexyl)-amide | 0.00257 | 0.01266 |

-continued

Activity table

| Ex. | Compound | Name | Ki 5-HT$_{2a}$: Human (5HT2a) | Ki dopamine d3 receptor: human (D3) |
|---|---|---|---|---|
| 16 |  | N-trans (4-{2-[4-(6-Fluoro-benzo[d]isoxazol-3-yl)-piperidin-1-yl]-ethyl}-cyclohexyl)-2-(3-methyl-pyrazol-1-yl)-acetamide | 0.002795 | 0.027618 |
| 17 |  | N-trans(4-{2-[4-(6-Fluoro-benzo[d]isoxazol-3-yl)-piperidin-1-yl]-ethyl}-cyclohexyl)-4-pyrrol-1-yl-benzamide | 0.00245 | 0.002607 |
| 18 |  | 1-Hydroxy-cyclopropanecarboxylic acid trans (4-{2-[4-(6-fluoro-benzo[d]isoxazol-3-yl)-piperidin-1-yl]-ethyl}-cyclohexyl)-amide | 0.001444 | 0.005916 |

-continued

Activity table

| Ex. | Compound | Name | Ki 5-HT$_{2a}$: Human (5HT2a) | Ki dopamine d3 receptor: human (D3) |
|---|---|---|---|---|
| 19 | | 1-Trifluoromethyl-cyclobutanecarboxylic acid trans (4-{2-[4-(6-fluoro-benzo[d]isoxazol-3-yl)-piperidin-1-yl]-ethyl}-cyclohexyl)-amide | 0.002257 | 0.00774 |
| 20 | | 3,3,3-Trifluoro-N-trans (4-{2-[4-(6-fluoro-benzo[d]isoxazol-3-yl)-piperidin-1-yl]-ethyl}-cyclohexyl)-propionamide | 0.002782 | 0.005189 |
| 21 | | 2-(3,5-Dimethoxy-phenyl)-N-trans (4-{2-[4-(6-fluoro-benzo[d]isoxazol-3-yl)-piperidin-1-yl]-ethyl}-cyclohexyl)-acetamide | 0.002953 | 0.008772 |

-continued

Activity table

| Ex. | Compound | Name | Ki 5-HT$_{2a}$: Human (5HT2a) | Ki dopamine d3 receptor: human (D3) |
|---|---|---|---|---|
| 22 | | 4-(2,6-Dimethyl-morpholin-4-yl)-N-trans (4-{2-[4-(6-fluoro-benzo[d]isoxazol-3-yl)-piperidin-1-yl]-ethyl}-cyclohexyl)-benzamide | 0.021224 | 0.136625 |
| 23 | | Benzo[1,3]dioxole-5-carboxylic acid trans (4-{2-[4-(6-fluoro-benzo[d]isoxazol-3-yl)-piperidin-1-yl]-ethyl}-cyclohexyl)-amide | 0.001714 | 0.002746 |
| 24 | | N-trans (4-{2-[4-(5-Fluoro-benzo[d]isoxazol-3-yl)-piperidin-1-yl]-ethyl}-cyclohexyl)-acetamide | 0.046865 | 0.002438 |

-continued

Activity table

| Ex. | Compound | Name | Ki 5-HT$_{2a}$: Human (5HT2a) | Ki dopamine d3 receptor: human (D3) |
|---|---|---|---|---|
| 25 | | N-trans (4-{2-[4-(5-Fluoro-benzo[d]isoxazol-3-yl)-piperidin-1-yl]-ethyl}-cyclohexyl)-4-morpholin-4-yl-benzamide | 0.02232 | 0.009036 |
| 26 | | N-trans (4-{2-[4-(5-Fluoro-benzo[d]isoxazol-3-yl)-piperidin-1-yl]-ethyl}-cyclohexyl)-3-methoxy-propionamide | 0.036954 | 0.003099 |
| 27 | | N-trans (4-{2-[4-(5-Fluoro-benzo[d]isoxazol-3-yl)-piperidin-1-yl]-ethyl}-cyclohexyl)-4-piperidin-1-yl-benzamide | 0.007004 | 0.0077 |

-continued

Activity table

| Ex. | Compound | Name | Ki 5-HT$_{2a}$: Human (5HT2a) | Ki dopamine d3 receptor: human (D3) |
|---|---|---|---|---|
| 28 | | 4-(2,6-Dimethyl-morpholin-4-yl)-N-trans (4-{2-[4-(5-fluoro-benzo[d]isoxazol-3-yl)-piperidin-1-yl]-ethyl}-cyclohexyl)-benzamide | 0.099138 | 0.085773 |
| 29 | | 4-(1,1-Dioxo-1,6,4-thiomorpholin-4-yl)-N-trans-(4-{2-[4-(5-fluoro-benzo[d]isoxazol-3-yl)-piperidin-1-yl]-ethyl}-cyclohexyl)-benzamide | 0.012352 | 0.005936 |
| 30 | | Benzo[1,3]dioxole-5-carboxylic acid trans (4-{2-[4-(5-fluoro-benzo[d]isoxazol-3-yl)-piperidin-1-yl]-ethyl}-cyclohexyl)-amide | 0.011217 | 0.003861 |
| 32 | | N-trans (4-{2-[4-(6-Chloro-benzo[d]isoxazol-3-yl)-piperidin-1-yl]-ethyl}-cyclohexyl)-3-methoxy-propionamide | 0.01655 | 0.008497 |

-continued

| Ex. | Compound | Name | Ki 5-HT$_{2a}$: Human (5HT2a) | Ki dopamine d3 receptor: human (D3) |
|---|---|---|---|---|
| 33 | | N-trans-(4-{2-[4-(6-Chloro-benzo[d]isoxazol-3-yl)-piperidin-1-yl]-ethyl}-cyclohexyl)-3,3,3-trifluoro-2-hydroxy-propionamide | 0.021866 | 0.011029 |
| 34 | | N-trans (4-{2-[4-(6-Chloro-benzo[d]isoxazol-3-yl)-piperidin-1-yl]-ethyl}-cyclohexyl)-2-(tetrahydro-pyran-2-yl)-acetamide | 0.005829 | 0.010734 |
| 34A | | N-trans (4-{2-[4-(6-Chloro-benzo[d]isoxazol-3-yl)-piperidin-1-yl]-ethyl}-cyclohexyl)-2-(R)-tetrahydro-pyran-2-yl-acetamide | 0.01368 | 0.010734 |

Activity table

| Ex. | Compound | Name | Ki 5-HT$_{2a}$: Human (5HT2a) | Ki dopamine d3 receptor: human (D3) |
|---|---|---|---|---|
| 34B | | N-trans (4-{2-[4-(6-Chloro-benzo[d]isoxazol-3-yl)-piperidin-1-yl]-ethyl}-cyclohexyl)-2-(S)-tetrahydro-pyran-2-yl-acetamide | 0.015304 | 0.003708 |
| 35 | | N-trans-(4-{2-[4-(6-Chloro-benzo[d]isoxazol-3-yl)-piperidin-1-yl]-ethyl}-cyclohexyl)-2-trans (4-methoxy-cyclohexyl)-acetamide | 0.009637 | 0.011578 |
| 36 | | N-trans (4-{2-[4-(6-Chloro-benzo[d]isoxazol-3-yl)-piperidin-1-yl]-ethyl}-cyclohexyl)-2-(1,4-dioxa-spiro[4.5]dec-8-yl)-acetamide | 0.00831 | 0.012221 |
| 37 | | N-trans-(4-{2-[4-(6-Chloro-benzo[d]isoxazol-3-yl)-piperidin-1-yl]-ethyl}-cyclohexyl)-3,3-dimethoxy-propionamide | 0.01365 | 0.00903 |
| 38 | | N-trans-(4-{2-[4-(6-Chloro-benzo[d]isoxazol-3-yl)-piperidin-1-yl]-ethyl}-cyclohexyl)-2-(tetrahydro-furan-2-yl)-acetamide | 0.013 | 0.009 |

-continued

Activity table

| Ex. | Compound | Name | Ki 5-HT$_{2a}$: Human (5HT2a) | Ki dopamine d3 receptor: human (D3) |
|---|---|---|---|---|
| 39 | | (R)-N-trans (4-{2-[4-(6-Chloro-benzo[d]isoxazol-3-yl)-piperidin-1-yl]-ethyl}-cyclohexyl)-3-hydroxy-butyramide | 0.013 | 0.017 |
| 40 | | N-trans (4-{2-[4-(6-Chloro-benzo[d]isoxazol-3-yl)-piperidin-1-yl]-ethyl}-cyclohexyl)-2-((S)-2,2-dimethyl-[1,3]dioxolan-4-yl)-acetamide | 0.025 | 0.006 |
| 41 | | N-trans (4-{2-[4-(6-Chloro-benzo[d]isoxazol-3-yl)-piperidin-1-yl]-ethyl}-cyclohexyl)-2-((1S,3S)-3-methoxy-cyclopentyl)-acetamide | 0.014 | 0.010 |
| 42 | | N-trans (4-{2-[4-(6-Chloro-benzo[d]isoxazol-3-yl)-piperidin-1-yl]-ethyl}-cyclohexyl)-2-(4-methoxy-4-methyl-cyclohexyl)-acetamide | 0.019 | 0.008 |
| 42A | | N-trans (4-{2-[4-(6-Chloro-benzo[d]isoxazol-3-yl)-piperidin-1-yl]-ethyl}-cyclohexyl)-2-(4-trans-methoxy-4-methyl-cyclohexyl)-acetamide | 0.016 | 0.006 |

-continued

Activity table

| Ex. | Compound | Name | Ki 5-HT$_{2a}$: Human (5HT2a) | Ki dopamine d3 receptor: human (D3) |
|---|---|---|---|---|
| 42B | | N-trans (4-{2-[4-(6-Chloro-benzo[d]isoxazol-3-yl)-piperidin-1-yl]-ethyl}-cyclohexyl)-2-(4-cis-methoxy-4-methyl-cyclohexyl)-acetamide | 0.014 | 0.004 |
| 43 | | N-trans (4-{2-[4-(6-Chloro-benzo[d]isoxazol-3-yl)-piperidin-1-yl]-ethyl}-cyclohexyl)-3-methoxy-butyramide | 0.013 | 0.010 |
| 43A | | (R)-N-trans (4-{2-[4-(6-Chloro-benzo[d]isoxazol-3-yl)-piperidin-1-yl]-ethyl}-cyclohexyl)-3-methoxy-butyramide | 0.016 | 0.015 |
| 43B | | (S)-N-(4-{2-(4-(6-Chloro-benzo[d]isoxazol-3-yl)-piperidin-1-yl]-ethyl}-cyclohexyl)-3-methoxy-butyramide | 0.016 | 0.006 |

-continued

| Ex. | Compound | Name | Ki 5-HT$_{2a}$: Human (5HT2a) | Ki dopamine d3 receptor: human (D3) |
|---|---|---|---|---|
| 44 | | N-trans-(4-{2-[4-(6-Chloro-benzo[d]isoxazol-3-yl)-piperidin-1-yl]-ethyl}-cyclohexyl)-2-trans (4-methoxymethyl-cyclohexyl)-acetamide | 0.019 | 0.009 |
| 45 | | N-trans (4-{2-[4-(6-Chloro-benzo[d]isoxazol-3-yl)-piperidin-1-yl]-ethyl}-cyclohexyl)-2-(4-hydroxy-4-methyl-cyclohexyl)-acetamide | 0.015 | 0.007 |
| 46 | | N-trans (4-{2-[4-(6-Chloro-benzo[d]isoxazol-3-yl)-piperidin-1-yl]-ethyl}-cyclohexyl)-acetamide | 0.023745 | 0.008189 |
| 47 | | Ethanesulfonic acid (4-trans {2-[4-(6-fluoro-benzo[d]isoxazol-3-yl)-piperidin-1-yl]-ethyl}-cyclohexyl)-amide | 0.001664 | 0.005852 |

-continued

Activity table

| Ex. | Compound | Name | Ki 5-HT$_{2a}$: Human (5HT2a) | Ki dopamine d3 receptor: human (D3) |
|---|---|---|---|---|
| 48 | | 4-Chloro-N-trans (4-{2-[4-(6-fluoro-benzo[d]isoxazol-3-yl)-piperidin-1-yl]-ethyl}-cyclohexyl)-benzenesulfonamide | 0.005132 | 0.005867 |
| 49 | | N-trans(4-{2-[4-(6-Fluoro-benzo[d]isoxazol-3-yl)-piperidin-1-yl]-ethyl}-cyclohexyl)-4-methoxy-benzenesulfonamide | 0.004394 | 0.003719 |
| 50 | | Pyridine-3-sulfonic acid trans(4-{2-[4-(6-fluoro-benzo[d]isoxazol-3-yl)-piperidin-1-yl]-ethyl}-cyclohexyl)-amide | 0.002476 | 0.00195 |
| 51 | | N-trans-(4-{2-[4-(6-Chloro-benzo[d]isoxazol-3-yl)-piperidin-1-yl]-ethyl}-cyclohexyl)-3-cyano-propionamide | 0.023745 | 0.008189 |

-continued

Activity table

| Ex. | Compound | Name | Ki 5-HT$_{2a}$: Human (5HT2a) | Ki dopamine d3 receptor: human (D3) |
|---|---|---|---|---|
| 52 | | N-trans-(4-{2-[4-(6-Chloro-benzo[d]isoxazol-3-yl)-piperidin-1-yl]-ethyl}-cyclohexyl)-2-cyano-acetamide | 0.015582 | 0.008772 |
| 53 | | N-trans-(4-{2-[4-(6-Chloro-benzo[d]isoxazol-3-yl)-piperidin-1-yl]-ethyl}-cyclohexyl)-2-(R)-tetrahydro-furan-2-yl-acetamide | 0.006193 | 0.014446 |
| 54 | | N-trans-(4-{2-[4-(6-Chloro-benzo[d]isoxazol-3-yl)-piperidin-1-yl]-ethyl}-cyclohexyl)-2-cyclopropyl-acetamide | 0.013092 | 0.003206 |
| 55 | | N-trans-(4-{2-[4-(6-Chloro-benzo[d]isoxazol-3-yl)-piperidin-1-yl]-ethyl}-cyclohexyl)-2-hydroxy-acetamide | 0.014991 | 0.01681 |
| 56 | | N-trans-(4-{2-[4-(6-Chloro-benzo[d]isoxazol-3-yl)-piperidin-1-yl]-ethyl}-cyclohexyl)-2-methanesulfonyl-acetamide | 0.015216 | 0.014784 |
| 57 | | N-trans-(4-{2-[4-(6-Chloro-benzo[d]isoxazol-3-yl)-piperidin-1-yl]-ethyl}-cyclohexyl)-2-[1,3]dioxan-2-yl-acetamide | 0.017625 | 0.00613 |

-continued

Activity table

| Ex. | Compound | Name | Ki 5-HT$_{2a}$: Human (5HT2a) | Ki dopamine d3 receptor: human (D3) |
|---|---|---|---|---|
| 58 | | N-trans-(4-{2-[4-(5-Chloro-benzo[d]isoxazol-3-yl)-piperidin-1-yl]-ethyl}-cyclohexyl)-2-(4-methoxy-cyclohexyl)-acetamide | 0.02467 | 0.008381 |
| 59 | | N-trans-(4-{2-[4-(5-Fluoro-benzo[d]isoxazol-3-yl)-piperidin-1-yl]-ethyl}-cyclohexyl)-methanesulfonamide | 0.027483 | 0.00798 |
| 60 | | N-trans-(4-{2-[4-(6-Chloro-5-fluoro-benzo[d]isoxazol-3-yl)-pipendm-1-yl]-ethyl}-cyclohexyl)-3-methoxy-propionamide | 0.043968 | 0.01354 |
| 61 | | N-trans- (4-{2-[4-(6-Chloro-5-fluoro-benzo[d]isoxazol-3-yl)-piperidin-1-yl]-ethyl}-cyclohexyl)-2-(tetrahydro-furan-2-yl)-acetamide | 0.031001 | 0.017732 |
| 62 | | N-trans- (4-{2-(4-(5,6-Difluoro-benzo[d]isoxazol-3-yl)-piperidin-1-yl]-ethyl}-cyclohexyl)-2-methoxy-acetamide | 0.01052 | 0.032674 |
| 63 | | N-trans- (4-{2-(4-(5,6-Difluoro-benzo[d]isoxazol-3-yl)-piperidin-1-yl]-ethyl}-cyclohexyl)-2-((1R,3R)-3-methoxy-cyclopentyl)-acetamide | 0.013209 | 0.019994 |
| 64 | | N-trans-(4-{2-(4-(5,6-Difluoro-benzo[d]isoxazol-3-yl)-piperidin-1-yl]-ethyl}-cyclohexyl)-2-(4-methoxy-cyclohexyl)-acetamide | 0.00767 | 0.017303 |

-continued

Activity table

| Ex. | Compound | Name | Ki 5-HT$_{2a}$: Human (5HT2a) | Ki dopamine d3 receptor: human (D3) |
|---|---|---|---|---|
| 65 | | N-trans-(4-{2-[4-(5,6-Difluoro-benzo[d]isoxazol-3-yl)-piperidin-1-yl]-ethyl}-cyclohexyl)-3-methoxy-propionamide | 0.012918 | 0.011356 |
| 66 | | N-trans-(4-{2-[4-(5,6-Difluoro-benzo[d]isoxazol-3-yl)-piperidin-1-yl]-ethyl}-cyclohexyl)-acetamide | 0.017739 | 0.011368 |
| 67 | | N-trans-(4-{2-[4-(5,6-Difluoro-benzo[d]isoxazol-3-yl)-piperidin-1-yl]-ethyl}-cyclohexyl)-2-hydroxy-acetamide | 0.011782 | 0.01995 |
| 68 | | N-trans-(4-{2-[4-(5,6-Difluoro-benzo[d]isoxazol-3-yl)-piperidin-1-yl]-ethyl}-cyclohexyl)-3-hydroxy-propionamide | 0.024792 | 0.01172 |
| 69 | | N-trans- (4-{2-[4-(5,6-Difluoro-benzo[d]isoxazol-3-yl)-piperidin-1-yl]-ethyl}-cyclohexyl)-2-(4-hydroxy-cyclohexyl)-acetamide | 0.007848 | 0.020912 |
| 70 | | N-trans- (4-{2-[4-(5,6-Difluoro-benzo[d]isoxazol-3-yl)-piperidin-1-yl]-ethyl}-cyclohexyl)-2-((1R,3R)-3-hydroxy-cyclopentyl)-acetamide | 0.011439 | 0.019756 |
| 71 | | Tetrahydro-pyran-4-carboxylic acid trans-(4-{2-[4-(5,6-difluoro-benzo[d]isoxazol-3-yl)-piperidin-1-yl]-ethyl}-cyclohexyl)-amide | 0.00786 | 0.018169 |

-continued

Activity table

| Ex. | Compound | Name | Ki 5-HT$_{2a}$: Human (5HT2a) | Ki dopamine d3 receptor: human (D3) |
|---|---|---|---|---|
| 72 | | N-trans-(4-{2-[4-(5,6-Difluoro-benzo[d]isoxazol-3-yl)-piperidin-1-yl]-ethyl}-cyclohexyl)-2-[1,3]dioxan-2-yl-acetamide | 0.009394 | 0.013512 |
| 73 | | N-trans-(4-{2-[4-(6-Methyl-benzo[d]isoxazol-3-yl)-piperidin-1-yl]-ethyl}-cyclohexyl)-acetamide | 0.016758 | 0.009275 |

The present invention also provides pharmaceutical compositions containing compounds of the invention, for example, compounds of formula I or pharmaceutically acceptable salts thereof and a pharmaceutically acceptable carrier. Such pharmaceutical compositions can be in the form of tablets, coated tablets, dragées, hard and soft gelatin capsules, solutions, emulsions or suspensions. The pharmaceutical compositions also can be in the form of suppositories or injectable solutions.

The pharmaceutical compositions of the invention, in addition to one or more compounds of the invention, contain a pharmaceutically acceptable carrier. Suitable pharmaceutically acceptable carriers include pharmaceutically inert, inorganic or organic carriers. Lactose, corn starch or derivatives thereof, talc, stearic acid or its salts and the like can be used, for example, as such as carriers for tablets, coated tablets, dragées and hard gelatine capsules. Suitable carriers for soft gelatine capsules are, for example, vegetable oils, waxes, fats, semi-solid and liquid polyols and the like; depending on the nature of the active substance no carriers are, however, usually required in the case of soft gelatine capsules. Suitable carriers for the production of solutions and syrups are, for example, water, polyols, sucrose, invert sugar, glucose and the like. Adjuvants, such as alcohols, polyols, glycerol, vegetable oils and the like, can be used for aqueous injection solutions of water-soluble salts of compounds of formula I, but as a rule are not necessary. Suitable carriers for suppositories are, for example, natural or hardened oils, waxes, fats, semi-liquid or liquid polyols and the like.

In addition, the pharmaceutical compositions can contain preservatives, solubilizers, stabilizers, wetting agents, emulsifiers, sweeteners, colorants, flavorants, salts for varying the osmotic pressure, buffers, masking agents or antioxidants. They can also contain still other therapeutically valuable substances.

The present invention also provides a method for the manufacture of pharmaceutical compositions. Such process comprises bringing one or more compounds of formula I and/or pharmaceutically acceptable acid addition salts thereof and, if desired, one or more other therapeutically valuable substances into a galenical administration form together with one or more therapeutically inert carriers.

The compounds and compositions of the present invention can be administered in a conventional manner, for example, orally, rectally, or parenterally. The pharmaceutical compositions of the invention can be administered orally, for example, in the form of tablets, coated tablets, dragées, hard and soft gelatine capsules, solutions, emulsions, or suspensions. The pharmaceutical compositions also can be administered rectally, for example, in the form of suppositories, or parenterally, for example, in the form of injectable solutions.

As mentioned hereinabove, the compounds of the invention have high affinity for the dopamine $D_3$ and serotonin 5-HT$_{2A}$ receptors and are expected to be effective in the treatment of psychotic disorders which include schizophrenia, schizoaffective disorders, bipolar disease, mania, psychotic depression, and other psychoses involving paranoia and delusions (Reavill-C, et al. (2000) Pharmacological actions of a novel, high-affinity, and selective human dopamine D3 receptor antagonist, SB-277011-A. JPET 294:1154-1165; Harrison, P. J. (1999) Neurochemical alterations in schizophrenia affecting the putative receptor targets of atypical antipsychotics.

Focus on dopamine (D1, D3, D4) and 5-HT2A receptors. Br. J. Psychiatry Suppl. 38, 12-22; de Angelis, L. (2002) 5-HT2A antagonists in psychiatric disorders. Curr. Opin. Investig. Drugs 3, 106-112; Joyce, J. N. and Millan, M. J., (2005) Dopamine D3 receptor antagonists as therapeutic agents. Drug Discovery Today, 1 July, Vol. 10, No. 13, P. 917-25); drug dependency and abuse and withdrawal (Vorel, S. R. et al. (2002) Dopamine D3 receptor antagonism inhibits cocaine-seeking and cocaine-enhanced brain reward in rats. J. Neurosci., 22, 9595-9603; Campos, A. C. et al. (2003) The dopamine D3 receptor antagonist SB277011A antagonizes nicotine-enhanced brain-stimulation reward in rat. Soc. Neurosci. Abstr., 322.8; Ashby, et al. (2003) Acute administration of the selective D3 receptor antagonist SB-277011-A blocks the acquisition and expression of the conditioned place preference response to heroin in male rats. Synapse, 48, 154-156); anxiety, and depression (Reavill-C et al. (2000) Pharmacological actions of a novel, high-affinity, and selective human dopamine D3 receptor antagonist, SB-277011-A. JPET 294: 1154-1165; Drescher, K. et al. (2002) In vivo effects of the selective dopamine D3 receptor antagonist A-437203. Am. Soc. Neurosci. 894.6).

The dosage at which compounds of the invention can be administered can vary within wide limits and will, of course, be fitted to the individual requirements in each particular case. In general, the effective dosage for oral or parenteral administration is between 0.01-20 mg/kg/day, with a dosage of 0.1-10 mg/kg/day being preferred for all of the indications described. The daily dosage for an adult human being weighing 70 kg accordingly lies between 0.7-1400 mg per day, preferably between 7 and 700 mg per day.

The following examples are provided to further elucidate the invention:

Example 1

4N-trans(4-{2-[4-(6-Fluoro-benzo[d]isoxazol-3-yl)-piperidin-1-yl]-ethyl}-cyclohexyl)-acetamide Intermediate B Trans-(4-amino-cyclohexyl)-acetic acid ethyl ester Step 1

(4-Nitro-phenyl)-acetic acid (50 g, 276 mmol) was added to a stirred solution of 22.08 g of 50% sodium hydroxide solution in 450 mL deionized water. The clear yellow solution is transferred into a high-pressure autoclave that it charged with 30 g (511 mmol) of water-wet sponge nickel catalyst. The autoclave is sealed, flushed with nitrogen and then pressurized to 115 bar with hydrogen. The reaction mixture is stirred and heated to 125° C. for 48 h. At that time the autoclave is cooled, vented and charged under nitrogen with another 30 g (511 mmol) of the sponge nickel catalyst. The autoclave is flushed again with nitrogen and then pressurized to 115 bar and the vessel is heated to 130° C. while stirring (a maximum pressure of 130 bars is observed). Hydrogenation is continued for 5 days to 130° C. The autoclave is then cooled, vented and flushed with nitrogen and the contents are removed and filtered through filter aid to remove catalyst. After removal of the solvent 74 g of crude material was obtained. The intermediated is used directly in the next step without purification. MS (m/e): 158.3 (M+H$^+$)

Step 2

A solution of the trans-(4-amino-cyclohexyl)-acetic acid obtained (74 g, 476 mmol) is adjusted to pH 5 with 25% HCl. The mixture was evaporated to dryness and dried under vacuum overnight. The residue was suspended in 146 mL of a 6.5N ethanolic HCl solution and 0.6 L of ethanol were added to the mixture. After 4 h refluxing, the mixture is cooled and filtered and the filtrate is concentrated to dryness under vacuum. The residue is dissolved in ethanol, treated with ether and cooled overnight in the refrigerator to give the trans-(4-Amino-cyclohexyl)-acetic acid ethyl ester hydrochloride (19.7 g, 32% on the two steps) as a white solid which was filtered and dried under vacuum. MS (m/e): 186.1 (M+H$^+$)

Intermediate C

Step 1

Trans-(4-tert-Butoxycarbonylamino-cyclohexyl)-acetic acid ethyl ester

To a solution of trans-(4-Amino-cyclohexyl)-acetic acid ethyl ester (1.28 g, 7 mmol), in dichloromethane (15 mL), di-tert-butyl-dicarbonate (2.26 g, 10 mmol), triethylamine (0.699 mL, 7 mmol) and 4-dimethylaminopyridine (0.042 mL, 0.35 mmol) were added. The mixture was stirred for 8 h until TLC indicated completion of the reaction. Water was added and the solution was extracted three times with dichloromethane. The combined organic layers were washed with water and brine, dried over magnesium sulfate, filtered and evaporated. The crude product was purified by flash-chromatography on silica gel with hexane:ethyl acetate (4:2 to 3:2) to give 1.2 g (60%) of the product as a white solid. MS (m/e): 284.4 (M–H$^+$).

Step 2

Trans-[4-(2-Oxo-ethyl)-cyclohexyl]-carbamic acid tert-butyl ester

To a solution of trans-(4-tert-Butoxycarbonylamino-cyclohexyl)-acetic acid ethyl ester (1.04 g, 4 mmol), in toluene (10 mL) at −78° C. a 1.2M solution of DIBAL-H (5.1 mL, 6 mmol) in toluene was added. The mixture was stirred at −78° C. until TLC after 0.5 h indicated completion of the reaction. Water was added and the solution was extracted three times with dichloromethane. The combined organic layers were washed with water and brine, dried over magnesium sulfate, filtered and evaporated. The crude product was used without purification on the next step. MS (m/e): 242.3 (M+H$^+$).

Intermediate E

Trans (4-{2-[4-(6-Fluoro-benzo[d]isoxazol-3-yl)-piperidin-1-yl]-ethyl}-cyclohexyl)-carbamic acid tert-butyl ester A mixture of 6-fluoro-3-(4-piperidinyl)-1,2-benzisoxazole (4 g, 18.1 mmol), trans-[4-(2-oxo-ethyl)-cyclohexyl]-carbamic acid tert-butyl ester (5.4 g, 22.7 mmol), in 1,2 dichloroethane (55 mL) was stirred for 4 h at room temperature and sodium triacetoxyborohydride (6.9 g, 32.7 mmol) was added slowly and the resulting solution was stirred for 12 hours until the TLC indicated completion of the reaction. The mixture was filtrated and concentrated to dryness and purified with column chromatography on silica gel using $CH_2Cl_2$—$CH_2Cl_2$/MeOH (1-9:1). The product fractions were concentrated to give 9.4 g (21 mmol, 100% yield) of a light brown solid. MS (m/e): 446.3 (M+H$^+$).

Intermediate F

Trans 4-{2-[4-(6-Fluoro-benzo[d]isoxazol-3-yl)-piperidin-1-yl]-ethyl}-cyclohexylamine (could be obtained as the trifluoroacetic acid salt)

9.4 g (21 mmol) of (4-{2-[4-(6-Fluoro-benzo[d]isoxazol-3-yl)-piperidin-1-yl]-ethyl}-cyclohexyl)-carbamic acid tert-butyl ester is solved in dichloromethane (100 mL) and trifluoroacetic acid is added at 0° C. (13.3 mL, 174 mmol) and the mixture is stirred at room temperature overnight. NaHCO$_3$ is slowly added until pH 9 and the mixture extracted 3 times with dichloromethane and ethyl acetate. The solvent was evaporated to yield 5.5 g (16 mmol, 77%) of a light brown solid that was used without purification on the next steps. MS (m/e): 346.5 (M+H$^+$).

4N-trans(4-{2-[4-(6-Fluoro-benzo[d]isoxazol-3-yl)-piperidin-1-yl]-ethyl}-cyclohexyl)-acetamide 4-{2-[4-(6-Fluoro-benzo[d]isoxazol-3-yl)-piperidin-1-yl]-ethyl}-cyclohexylamine (0.03 g, 0.087 mmol) is suspended in dichloromethane (0.600 mL) and triethylamine is added (0.013 mL, 0.096 mmol) followed by acetylchloride (0.008 mL, 0.104 mmol) and the mixture was stirred for 30 minutes at room temperature until TLC indicated the end of the reaction. Sodium bicarbonate solution was added until pH 9 and the reaction extracted 3 times with dichloromethane. The organic phase was dried and purified with column chromatography on silica gel using $CH_2Cl_2$—$CH_2Cl_2$/MeOH (1-9:1). The product fractions were concentrated to give 0.022 g (0.056 mmol, 65% yield) of a white solid. MS (m/e): 388.5 (M+H$^+$).

Example 2

Tetrahydro-pyran-4-carboxylic acid trans(4-{2-[4-(6-fluoro-benzo[d]isoxazol-3-yl)-piperidin-1-yl]-ethyl}-cyclohexyl)-amide Tetrahydro-pyran-4-carboxylic acid (0.013 g, 0.096 mmol), 2-(1H-benzotriazol-1-yl)-1,1,3,3-tetramethyl uronium tetrafluoroborate (0.026 g, 0.08 mmol) and (0.04 mL, 0.24 mmol) of N-ethyldiisopropylamine were stirred in 0.6 mL of DMF for 0.5 h at room temperature and Trans 4-{2-[4-(6-Fluoro-benzo[d]isoxazol-3-yl)-piperidin-1-yl]-ethyl}-cyclohexylamine (could be obtained as the trifluoroacetic acid salt) (trifluoro acetic acid salt) (0.030 g, 0.08 mmol) was added. The mixture was stirred for 12 hours at room temperature. The mixture was concentrated to dryness and the residue was taken up on methanol and purified with preparative HPLC on reversed phase eluting with acetonitrile/water. The combined producted fractions were evaporated under reduced pressure to yield 0.027 g of a off-white solid (0.06 mmol, 74%). MS (m/e): 458.5 (M+H$^+$).

According to the procedure described for the synthesis of example 2 further derivatives have been synthesized from the respective Trans 4-{2-[4-(6-Fluoro-benzo[d]isoxazol-3-yl)-piperidin-1-yl]-ethyl}-cyclohexylamine (could be obtained as the trifluoroacetic acid salt) and the corresponding acid. They comprise examples 2 to 41 on Table 1.

TABLE 1

| Ex. | Systematic name | MW | Starting materials | MW found (M + H)$^+$ |
| --- | --- | --- | --- | --- |
| 2 | Tetrahydro-pyran-4-carboxylic acid trans (4-{2-[4-(6-fluoro-benzo[d]isoxazol-3-yl)-piperidin-1-yl]-ethyl}-cyclohexyl)-amide | 457.59 | Trans 4-{2-[4-(6-Fluoro-benzo[d]isoxazol-3-yl)-piperidin-1-yl]-ethyl}-cyclohexylamine (could be obtained as the trifluoroacetic acid salt) and Tetrahydro-pyran-4-carboxylic acid | 458.5 |
| 3 | N-trans (4-{2-[4-(6-Fluoro-benzo[d]isoxazol-3-yl)-piperidin-1-yl]-ethyl}-cyclohexyl)-3-methoxy-propionamide | 431.55 | Trans 4-{2-[4-(6-Fluoro-benzo[d]isoxazol-3-yl)-piperidin-1-yl]-ethyl}-cyclohexylamine (could be obtained as the trifluoroacetic acid salt) and 3-methoxy-propionic acid | 432.2 |
| 4 | N-trans-(4-{2-[4-(6-Fluoro-benzo[d]isoxazol-3-yl)-piperidin-1-yl]-ethyl}-cyclohexyl)-4-morpholin-4-yl-benzamide | 534.68 | Trans 4-{2-[4-(6-Fluoro-benzo[d]isoxazol-3-yl)-piperidin-1-yl]-ethyl}-cyclohexylamine (could be obtained as the trifluoroacetic acid salt) and 4-morpholin-4-yl-benzoic acid | 535.5 |
| 4A | N-Trans (4-{2-[4-(6-Fluoro-benzo[d]isoxazol-3-yl)-piperidin-1-yl]-ethyl}-cyclohexyl)-6-morpholin-4-yl-nicotinamide | 535.6 | Trans 4-{2-[4-(6-Fluoro-benzo[d]isoxazol-3-yl)-piperidin-1-yl]-ethyl}-cyclohexylamine (could be obtained as the trifluoroacetic acid salt) and 6-morpholino nicotinic acid | 536.0 |
| 4B | 5-Morpholin-4-yl-pyrazine-2-carboxylic acid trans (4-{2-[4-(6-fluoro-benzo[d]isoxazol-3-yl)-piperidin-1-yl]-ethyl}-cyclohexyl)-amide | 536.6 | Trans 4-{2-[4-(6-Fluoro-benzo[d]isoxazol-3-yl)-piperidin-1-yl]-ethyl}-cyclohexylamine (could be obtained as the trifluoroacetic acid salt) and 5-Morpholin-4-yl-pyrazine-2-carboxylic acid (ester prepared by substitution of Chloro derivative using Morpholine with TEA in Dioxane at 45° C. during 16 hours) | 537.2 |
| 4C | 6-Morpholin-4-yl-pyridazine-3-carboxylic acid-trans (4-{2-[4-(6-fluoro-benzo[d]isoxazol-3-yl)-piperidin-1-yl]-ethyl}-cyclohexyl)-amide | 536.6 | Trans 4-{2-[4-(6-Fluoro-benzo[d]isoxazol-3-yl)-piperidin-1-yl]-ethyl}-cyclohexylamine (could be obtained as the trifluoroacetic acid salt) and 6-Morpholin-4-yl-pyridazine-3-carboxylic acid (ester prepared by substitution of Chloro derivative using Morpholine with TEA in | 537.5 |

TABLE 1-continued

| Ex. | Systematic name | MW | Starting materials | MW found (M + H)+ |
|---|---|---|---|---|
| | | | Dioxane at 45° C. during 16 hours | |
| 4D | 2-Morpholin-4-yl-pyrimidine-5-carboxylic acid trans (4-{2-[4-(6-fluoro-benzo[d]isoxazol-3-yl)-piperidin-1-yl]-ethyl}-cyclohexyl)-amide | 536.6 | Trans 4-{2-[4-(6-Fluoro-benzo[d]isoxazol-3-yl)-piperidin-1-yl]-ethyl}-cyclohexylamine (could be obtained as the trifluoroacetic acid salt) and 2-morpholin-4-yl-pyrimidine-5-carboxylic acid (commercial available) | 537.7 |
| 5 | 3-Fluoro-N-trans (4-{2-[4-(6-fluoro-benzo[d]isoxazol-3-yl)-piperidin-1-yl]-ethyl}-cyclohexyl)-4-morpholin-4-yl-benzamide | 552.6 | Trans 4-{2-[4-(6-Fluoro-benzo[d]isoxazol-3-yl)-piperidin-1-yl]-ethyl}-cyclohexylamine (could be obtained as the trifluoroacetic acid salt) and 3-Fluoro-4-morpholin-4-yl-benzoic acid (prepared by LiOH hydrolysis of the methyl ester commercial available) | 553.5 |
| 6 | 4-Dimethylamino-N-trans (4-{2-[4-(6-fluoro-benzo[d]isoxazol-3-yl)-piperidin-1-yl]-ethyl}-cyclohexyl)-benzamide | 492.6 | Trans 4-{2-[4-(6-Fluoro-benzo[d]isoxazol-3-yl)-piperidin-1-yl]-ethyl}-cyclohexylamine (could be obtained as the trifluoroacetic acid salt) and 4-Dimethylamino benzoic acid | 493.1 |
| 7 | 2-Benzo[1,3]dioxol-5-yl-N-trans (4-{2-[4-(6-fluoro-benzo[d]isoxazol-3-yl)-piperidin-1-yl]-ethyl}-cyclohexyl)-acetamide | 507.6 | Trans 4-{2-[4-(6-Fluoro-benzo[d]isoxazol-3-yl)-piperidin-1-yl]-ethyl}-cyclohexylamine (could be obtained as the trifluoroacetic acid salt) and 3,4-(methylenedioxy) phenylacetic acid | 508.4 |
| 8 | N-trans-(4-{2-[4-(6-Fluoro-benzo[d]isoxazol-3-yl)-piperidin-1-yl]-ethyl}-cyclohexyl)-4-methoxy-benzamide | 479.6 | Trans 4-{2-[4-(6-Fluoro-benzo[d]isoxazol-3-yl)-piperidin-1-yl]-ethyl}-cyclohexylamine (could be obtained as the trifluoroacetic acid salt) and 4-methoxy-benzoic acid | 480.3 |
| 9 | 4-tert-Butoxy-N-trans (4-{2[4-(6-fluoro-benzo[d]isoxazol-3-yl)-piperidin-1-yl]-ethyl}-cyclohexyl)-benzamide | 521.7 | Trans 4-{2-[4-(6-Fluoro-benzo[d]isoxazol-3-yl)-piperidin-1-yl]-ethyl}-cyclohexylamine (could be obtained as the trifluoroacetic acid salt) and 4-tert-Butoxy-benzoic acid | 522.7 |
| 10 | 4-Chloro-N-trans (4-{2-[4-(6-fluoro-benzo[d]isoxazol-3-yl)-piperidin-1-yl]-ethyl}-cyclohexyl)-benzamide | 484.01 | Trans 4-{2-[4-(6-Fluoro-benzo[d]isoxazol-3-yl)-piperidin-1-yl]-ethyl}-cyclohexylamine (could be obtained as the trifluoroacetic acid salt) and 4-tert-chloro-benzoic acid | 484.4 |
| 11 | 4-(1,1-Dioxo-1,6-thiomorpholin-4-yl)-N-trans (4-[2-[4-(6-fluoro-benzo[d]isoxazol-3-yl)-piperidin-1-yl]-ethyl}-cyclohexyl)-benzamide | 582.74 | Trans 4-{2-[4-(6-Fluoro-benzo[d]isoxazol-3-yl)-piperidin-1-yl]-ethyl}-cyclohexylamine (could be obtained as the trifluoroacetic acid salt) and 4-(1,1-Dioxo-1,6-thiomorpholin-4-yl)-benzoic acid | 583.2 |
| 12 | N-trans (4-{2-[4-(6-Fluoro-benzo[d]isoxazol-3-yl)-piperidin-1-yl]-ethyl}-cyclohexyl)-2-morpholin-4-yl-isonicotinamide | 535.66 | Trans 4-{2-[4-(6-Fluoro-benzo[d]isoxazol-3-yl)-piperidin-1-yl]-ethyl}-cyclohexylamine (could be obtained as the trifluoroacetic acid salt) and 2-morpholin-4-yl-isonicotinic acid | 536.5 |
| 13 | N-trans (4-{2-[4-(6-Fluoro-benzo[d]isoxazol-3-yl)-piperidin-1-yl]-ethyl}-cyclohexyl)-2-methoxy-isonicotinamide | 480.6 | Trans 4-{2-[4-(6-Fluoro-benzo[d]isoxazol-3-yl)-piperidin-1-yl]-ethyl}-cyclohexylamine (could be obtained as the trifluoroacetic | 481.4 |

TABLE 1-continued

| Ex. | Systematic name | MW | Starting materials | MW found (M + H)+ |
|---|---|---|---|---|
| | | | acid salt) and 2-methoxy-isonicotic acid | |
| 14 | N-trans (4-{2-[4-(6-Fluoro-benzo[d]isoxazol-3-yl)-piperidin-1-yl]-ethyl}-cyclohexyl)-4-piperidin-1-yl-benzamide | 532.7 | Trans 4-{2-[4-(6-Fluoro-benzo[d]isoxazol-3-yl)-piperidin-1-yl]-ethyl}-cyclohexylamine (could be obtained as the trifluoroacetic acid salt) and 4-piperidin-1-yl-benzoic acid | 533.3 |
| 15 | 2,3-Dihydro-benzo[1,4]dioxine-2-carboxylic acid trans (4-{2-[4-(6-fluoro-benzo[d]isoxazol-3-yl)-piperidin-1-yl]-ethyl}-cyclohexyl)-amide | 507.6 | Trans 4-{2-[4-(6-Fluoro-benzo[d]isoxazol-3-yl)-piperidin-1-yl]-ethyl}-cyclohexylamine (could be obtained as the trifluoroacetic acid salt) and 2,3-Dihydro-benzo[1,4]dioxine-2-carboxylic acid | 508.4 |
| 16 | N-trans (4-{2-[4-(6-Fluoro-benzo[d]isoxazol-3-yl)-piperidin-1-yl]-ethyl}-cyclohexyl)-2-(3-methyl-pyrazol-1-yl)-acetamide | 467.6 | Trans 4-{2-[4-(6-Fluoro-benzo[d]isoxazol-3-yl)-piperidin-1-yl]-ethyl}-cyclohexylamine (could be obtained as the trifluoroacetic acid salt) and (3-Methyl-pyrazol-1-yl)-acetic acid | 468.4 |
| 17 | N-trans(4-{2-[4-(6-Fluoro-benzo[d]isoxazol-3-yl)-piperidin-1-yl]-ethyl}-cyclohexyl)-4-pyrrol-1-yl-benzamide | 514.6 | Trans 4-{2-[4-(6-Fluoro-benzo[d]isoxazol-3-yl)-piperidin-1-yl]-ethyl}-cyclohexylamine (could be obtained as the trifluoroacetic acid salt) and 4-pyrrol-1-yl-benzoic acid | 515.0 |
| 18 | 1-Hydroxy-cyclopropanecarboxylic acid trans (4-{2-[4-(6-fluoro-benzo[d]isoxazol-3-yl)-piperidin-1-yl]-ethyl}-cyclohexyl)-amide | 429.5 | Trans 4-{2-[4-(6-Fluoro-benzo[d]isoxazol-3-yl)-piperidin-1-yl]-ethyl}-cyclohexylamine (could be obtained as the trifluoroacetic acid salt) and 1-Hydroxy-cyclopropanecarboxylic acid | 430.3 |
| 19 | 1-Trifluoromethyl-cyclobutanecarboxylic acid trans (4-{2-[4-(6-fluoro-benzo[d]isoxazol-3-yl)-piperidin-1-yl]-ethyl}-cyclohexyl)-amide | 495.6 | Trans 4-{2-[4-(6-Fluoro-benzo[d]isoxazol-3-yl)-piperidin-1-yl]-ethyl}-cyclohexylamine (could be obtained as the trifluoroacetic acid salt) and 1-Trifluoromethyl-cyclobutanecarboxylic acid | 496.1 |
| 20 | 3,3,3-Trifluoro-N-trans (4-{2-[4-(6-fluoro-benzo[d]isoxazol-3-yl)-piperidin-1-yl]-ethyl}-cyclohexyl)-propionamide | 455.5 | Trans 4-{2-[4-(6-Fluoro-benzo[d]isoxazol-3-yl)-piperidin-1-yl]-ethyl}-cyclohexylamine (could be obtained as the trifluoroacetic acid salt) and 3,3,3-Trifluoro propionic acid | 456.3 |
| 21 | 2-(3,5-Dimethoxy-phenyl)-N-trans (4-{2-[4-(6-fluoro-benzo[d]isoxazol-3-yl)-piperidin-1-yl]-ethyl}-cyclohexyl)-acetamide | 523.6 | Trans 4-{2-[4-(6-Fluoro-benzo[d]isoxazol-3-yl)-piperidin-1-yl]-ethyl}-cyclohexylamine (could be obtained as the trifluoroacetic acid salt) and 2-(3,5-Dimethoxy-phenyl)-acetic acid | 524.3 |
| 22 | 4-(2,6-Dimethyl-morpholin-4-yl)-N-trans (4-{2-[4-(6-fluoro-benzo[d]isoxazol-3-yl)-piperidin-1-yl]-ethyl}-cyclohexyl)-benzamide | 562.7 | Trans 4-{2-[4-(6-Fluoro-benzo[d]isoxazol-3-yl)-piperidin-1-yl]-ethyl}-cyclohexylamine (could be obtained as the trifluoroacetic acid salt) and 4-(2,6-Dimethyl-morpholin-4-yl)-benzoic acid | 563.5 |
| 23 | Benzo[1,3]dioxole-5-carboxylic acid trans (4-{2-[4-(6-fluoro-benzo[d]isoxazol-3-yl)-piperidin-1-yl]-ethyl}-cyclohexyl)-amide | 498.6 | Trans 4-{2-[4-(6-Fluoro-benzo[d]isoxazol-3-yl)-piperidin-1-yl]-ethyl}-cyclohexylamine (could be obtained as the trifluoroacetic acid salt) and Benzo[1,3]dioxole-5-carboxylic acid | 499.5 |

Example 24

N-trans(4-{2-[4-(5-Fluoro-benzo[d]isoxazol-3-yl)-piperidin-1-yl]-ethyl}-cyclohexyl)-acetamide

Intermediate E

Trans (4-{2-[4-(5-Fluoro-benzo[d]isoxazol-3-yl)-piperidin-1-yl]-ethyl}-cyclohexyl)-carbamic acid tert-butyl ester A mixture of 5-fluoro-3-(4-piperidinyl)-1,2-benzisoxazole (1.3 g, 5 mmol), trans-[4-(2-oxo-ethyl)-cyclohexyl]-carbamic acid tert-butyl ester (example 1, intermediate C) (1.6 g, 6 mmol), triethylamine (0.64 mL, 5 mmol) in 1,2 dichloroethane (27 mL) was stirred for 4 h at room temperature and sodium triacetoxyborohydride (1.9 g, 9 mmol) was added slowly and the resulting solution was stirred for 12 hours until the TLC indicated completion of the reaction. The mixture was filtrated and concentrated to dryness and purified with column chromatography on silica gel using $CH_2Cl_2$—$CH_2Cl_2$/MeOH (1-9:1). The product fractions were concentrated to give 2.3 g (5.1 mmol, 100% yield) of a off-white solid. MS (m/e): 446.3 (M+H$^+$).

Intermediate F

Trans 4-{2-[4-(5-Fluoro-benzo[d]isoxazol-3-yl)-piperidin-1-yl]-ethyl}-cyclohexylamine; compound with trifluoro-acetic acid 2.3 g (5 mmol) of trans(4-{2-[4-(5-Fluoro-benzo[d]isoxazol-3-yl)-piperidin-1-yl]-ethyl}-cyclohexyl)-carbamic acid tert-butyl ester is solved in dichloromethane (15 mL) and trifluoroacetic acid is added at 0° C. (10.7 mL, 46 mmol) and the mixture is stirred at room temperature overnight. NaHCO$_3$ is slowly added until pH 9 and the mixture extracted 3 times with dichloromethane and ethyl acetate. The solvent was evaporated to yield 1.86 g (5.3 mmol, 100%) of a white solid that was used without purification on the next steps. MS (m/e): 346.3 (M+H$^+$).

N-trans(4-{2-[4-(5-Fluoro-benzo[d]isoxazol-3-yl)-piperidin-1-yl]-ethyl}-cyclohexyl)-acetamide Prepared as described on example 1 from Trans 4-{2-[4-(5-Fluoro-benzo[d]isoxazol-3-yl)-piperidin-1-yl]-ethyl}-cyclohexylamine in dichloromethane with triethylamine and acetylchloride. MS (m/e): 388.3 (M+H$^+$).

Example 25

N-trans(4-{2-[4-(5-Fluoro-benzo[d]isoxazol-3-yl)-piperidin-1-yl]-ethyl}-cyclohexyl)-4-morpholin-4-yl-benzamide 4-morpholinobenzoic acid (0.153 g, 0.74 mmol), 2-(1H-benzotriazol-1-yl)-1,1,3,3-tetramethyl uronium tetrafluoroborate (0.026 g, 0.69 mmol) and (0.350 mL, 2.02 mmol) of N-ethyldiisopropylamine were stirred in 5 mL of DMF for 0.5 h at room temperature and Trans 4-{2-[4-(5-Fluoro-benzo[d]isoxazol-3-yl)-piperidin-1-yl]-ethyl}-cyclohexylamine (trifluoro acetic acid salt) (0.300 g, 0.69 mmol) was added. The mixture was stirred for 12 hours at room temperature. The mixture was concentrated to dryness and the residue was taken up on methanol and purified with chromatography eluting with $CH_2Cl_2$—$CH_2Cl_2$/MeOH (1-9:1). The combined produced fractions were evaporated under reduced pressure to yield 0.24 g of an off-white solid (0.5 mmol, 70%). MS (m/e): 535.3 (M+H$^+$).

Example 26

N-trans(4-{2-[4-(5-Fluoro-benzo[d]isoxazol-3-yl)-piperidin-1-yl]-ethyl}-cyclohexyl)-3-methoxy-propionamide Prepared as described on example 25 using 3-methoxy-propionic acid and), 2-(1H-benzotriazol-1-yl)-1,1,3,3-tetramethyl uronium tetrafluoroborate, N-ethyldiisopropylamine in DMF and Trans 4-{2-[4-(5-Fluoro-benzo[d]isoxazol-3-yl)-piperidin-1-yl]-ethyl}-cyclohexylamine (trifluoroacetic acid salt) to yield 0.023 g of a white solid (0.05 mmol, 37%). MS (m/e): 332.4 (M+H$^+$).

Example 27

N-trans(4-{2-[4-(5-Fluoro-benzo[d]isoxazol-3-yl)-piperidin-1-yl]-ethyl}-cyclohexyl)-4-piperidin-1-yl-benzamide Prepared as described on example 26 using 4-piperidin-1-yl-benzoic acid, 2-(1H-benzotriazol-1-yl)-1,1,3,3-tetramethyl uronium tetrafluoroborate, N-ethyldiisopropylamine in DMF and Trans 4-{2-[4-(5-Fluoro-benzo[d]isoxazol-3-yl)-piperidin-1-yl]-ethyl}-cyclohexylamine (trifluoroacetic acid salt). The mixture was stirred for 12 hours at room temperature. The mixture was concentrated to dryness and the residue was taken up on methanol and purified with preparative HPLC on reversed phase eluting with acetonitrile/water.

The combined produced fractions were evaporated under reduced pressure to yield 0.028 g of a off-white solid (0.05 mmol, 49%). MS (m/e): 533.0 (M+H$^+$).

According to the procedure described for the synthesis of example 26 further derivatives have been synthesized from the respective Trans 4-{2-[4-(5-Fluoro-benzo[d]isoxazol-3-yl)-piperidin-1-yl]-ethyl}-cyclohexylamine (trifluoroacetic acid salt) and the corresponding acid. They comprise examples 28 to 30 on Table 2.

TABLE 2

| Ex. | Systematic name | MW | Starting materials | MW found (M + H)$^+$ |
|---|---|---|---|---|
| 28 | 4-(2,6-Dimethyl-morpholin-4-yl)-N-trans (4-{2-[4-(5-fluoro-benzo[d]isoxazol-3-yl)-piperidin-1-yl]-ethyl}-cyclohexyl)-benzamide | 562.7 | Trans 4-{2-[4-(5-Fluoro-benzo[d]isoxazol-3-yl)-piperidin-1-yl]-ethyl}-cyclohexylamine (trifluoroacetic acid salt) and 4-morpholinobenzoic acid | 563.0 |
| 29 | 4-(1,1-Dioxo-1,6,4-thiomorpholin-4-yl)-N trans-(4-{2-[4-(5-fluoro- | 582.7 | Trans 4-{2-[4-(5-Fluoro-benzo[d]isoxazol-3-yl)-piperidin-1-yl]-ethyl}- | 583.2 |

TABLE 2-continued

| Ex. | Systematic name | MW | Starting materials | MW found (M + H)+ |
|---|---|---|---|---|
|  | benzo[d]isoxazol-3-yl)-piperidin-1-yl]-ethyl}-cyclohexyl)-benzamide |  | cyclohexylamine (trifluoroacetic acid salt) and 4-(1,1-Dioxo thiomorpholino) benzoic acid |  |
| 30 | Benzo[1,3]dioxole-5-carboxylic acid trans (4-{2-[4-(5-fluoro-benzo[d]isoxazol-3-yl)-piperidin-1-yl]-ethyl}-cyclohexyl)-amide | 493.5 | Trans 4-{2-[4-(5-Fluoro-benzo[d]isoxazol-3-yl)-piperidin-1-yl]-ethyl}-cyclohexylamine (trifluoroacetic acid salt) and Benzo[1,3]dioxole-5-carboxylic acid | 494.4 |

Example 32

N-trans(4-{2-[4-(6-Chloro-benzo[d]isoxazol-3-yl)-piperidin-1-yl]-ethyl}-cyclohexyl)-3-methoxy-propionamide Intermediate D 1-[4-(2,4-Dichloro-benzoyl)-piperidin-1-yl]-ethanone Aluminium chloride (11, 24 g, 84 mmol) is added portionwise to 23 mL of dichlorobenzene (200 mmol). To this suspension 8 g of 1-acetylisonipecotoyl chloride (42 mmol) was added also portionwise. The mixture was stirred 10 minutes at room temperature and then at 90° C. for 4 hours until TLC indicated completion of the reaction that changed from a yellow/orange solution changed into dark orange upon heating. Water was added and the solution was extracted three times with dichloromethane. The combined organic layers were washed with water and brine, dried over magnesium sulfate, filtered and evaporated. The crude product was purified by flash-chromatography on silica gel with hexane:ethyl acetate (1:0 to 0:1) to give 6.3 g (50%) of the product as an orange oil. MS (m/e): 300.2 (M+).

1-(4-{(2,4-Dichloro-phenyl)-[(E)-hydroxyimino]-methyl}-piperidin-1-yl)-ethanone

1-[4-(2,4-Dichloro-benzoyl)-piperidin-1-yl]-ethanone (5.6 g, 19 mmol) was solved in ethanol (140 mL). Hydroxylamine (5.2 g, 75 mmol) was added followed by N,N-diisopropyl ethyl amine (12.8 mL, 75 mmol) and the reaction was refluxed to 100° C. for 12-20 hours until TLC indicated completion of the reaction. Water was added and the solution was extracted three times with dichloromethane. The combined organic layers were washed with water and brine, dried over magnesium sulfate, filtered and evaporated. The crude product was purified by flash-chromatography on silica gel with hexane:ethyl acetate (1:0 to 0:1) to give 2.15 g (37%) of the product as a white solid and 1.12 g of the starting material that was recovered. MS (m/e): 315.1 (M+H+).

1-[4-(6-Chloro-benzo[d]isoxazol-3-yl)-piperidin-1-yl]-ethanone 1-(4-{(2,4-Dichloro-phenyl)-[(E)-hydroxyimino]-methyl}-piperidin-1-yl)-ethanone (2.15 g, 7 mmol) was solved in THF (34 mL) and potassium tert-butoxide was added (0.844 g, 7.5 mmol). The mixture was stirred for 2 hours until TLC indicated the end of the reaction. The solvent was removed and the mixture purified by flash-chromatography on silica gel with hexane:ethyl acetate (1:0 to 0:1). The combined producted fractions were evaporated under reduced pressure to yield 1.45 g of a colourless oil (75%). MS (m/e): 279.1 (M+H+).

6-Chloro-3-piperidin-4-yl-benzo[d]isoxazole hydrochloride

1-[4-(6-Chloro-benzo[d]isoxazol-3-yl)-piperidin-1-yl]-ethanone (1.45 g, 5.3 mmol) was diluted with an aqueous solution of HCl 6N (13.8 mL, 16 mmol) and the mixture was refluxed overnight. After cooling, 2×20 mL of ether was added and the mixture extracted. A solution of NaOH was added to the aqueous phase until pH 11 and the mixture was extracted with ethyl acetate three times. The combined ethyl acetate fractions were dried and evaporated under reduced pressure to yield 1.14 g of a light brown solid (93%). MS (m/e): 236.9 (M+H+).

Intermediate E

Trans (4-{2-[4-(6-Chloro-benzo[d]isoxazol-3-yl)-piperidin-1-yl]-ethyl}-cyclohexyl)-carbamic acid tert-butyl ester Prepared as described for intermediate F (example 1) from a mixture 6-Chloro-3-piperidin-4-yl-benzo[d]isoxazole hydrochloride (0.942 g, 4 mmol), trans-[4-(2-Oxo-ethyl)-cyclohexyl]-carbamic acid tert-butyl ester (1.06 g, 4 mmol) and sodium triacetoxyborohydride (1.51 g, 7 mmol) in 1,2 dichloroethane (9.8 mL) The product fractions were concentrated to give 1.2 g (2.6 mmol, 64.3% yield) of a light brown solid. MS (m/e): 462.4 (M+H+).

Intermediate F

Trans 4-{2-[4-(6-Chloro-benzo[d]isoxazol-3-yl)-piperidin-1-yl]-ethyl}-cyclohexylamine (could be obtained as the trifluoroacetic acid salt)

Prepared as described for example 1 from Trans (4-{2-[4-(6-Chloro-benzo[d]isoxazol-3-yl)-piperidin-1-yl]-ethyl}-cyclohexyl)-carbamic acid tert-butyl ester and trifluoroacetic acid at 0° C. The product was obtained as a light yellow solid (0.197 g, 52%). MS (m/e): 362.4 (M+H+).

N-trans(4-{2-[4-(6-Chloro-benzo[d]isoxazol-3-yl)-piperidin-1-yl]-ethyl}-cyclohexyl)-3-methoxy-propionamide Prepared as described for example 2 from 3-methoxy-propionic acid, 2-(1H-benzotriazol-1-yl)-1,1,3,3-tetramethyl uronium tetrafluoroborate, N-ethyldiisopropylamine and Trans 4-{2-[4-(6-Chloro-benzo[d]isoxazol-3-yl)-piperidin-1-yl]-ethyl}-cyclohexylamine (trifluoro acetic acid salt) in DMF for 12 hours at room temperature. The mixture was concentrated to dryness and the residue was taken up on methanol and purified with chromatography eluting with $CH_2Cl_2$—$CH_2Cl_2$/MeOH (1-9:1). The combined producted fractions were evaporated under reduced pressure to yield 0.022 g of an off-white solid (0.05 mmol, 45%). MS (m/e): 448.3 (M+H$^+$).

According to the procedure described for the synthesis of example 32 further derivatives have been synthesized from Trans 4-{2-[4-(6-Chloro-benzo[d]isoxazol-3-yl)-piperidin-1-yl]-ethyl}-cyclohexylamine and the corresponding acids: commercially available, or obtained by methods known on the art (e.g. hydrolysis of the corresponding ester) or by methods described hereinbefore (see Table 3).

TABLE 3

| Ex. No | Systematic name | MW | Starting materials | MW found (M + H)+ |
|---|---|---|---|---|
| 33 | N-trans-(4{2-[4-(6-Chloro-benzo[d]isoxazol-3-yl)-piperidin-1-yl]-ethyl}-cyclohexyl)-3,3,3-trifluoro-2-hydroxy-propionamide | 487.9 | Trans 4-{2-[4-(6-Chloro-benzo[d]isoxazol-3-yl)-piperidin-1-yl]-ethyl}-cyclohexylamine (trifluoro-acetic acid salt) and 3,3,3-trifluoro-2-hydroxy- propionic acid (commercially available) | 488.1 |
| 34 34A 34B | N-trans (4-{2-[4-(6-Chloro-benzo[d]isoxazol-3-yl)-piperidin-1-yl]-ethyl}-cyclohexyl)-2-(tetrahydro-pyran-2-yl)-acetamide | 488.0 | Trans 4-{2-[4-(6-Chloro-benzo[d]isoxazol-3-yl)-piperidin-1-yl]-ethyl}-cyclohexylamine (trifluoro-acetic acid salt) and 2-(tetrahydro-pyran-2-yl)-acetic acid (commercially available) Note: Chiral separation yields both enantiomers. | 488.3 |
| 34A | N-trans (4-{2-[4-(6-Chloro-benzo[d]isoxazol-3-yl)-piperidin-1-yl]-ethyl}-cyclohexyl)-2-(R)-tetrahydro-pyran-2-yl-acetamide | 488.0 | Separation of racemic mixture by chiral column | 488.4 |
| 34B | N-trans (4-{2-[4-(6-Chloro-benzo[d]isoxazol-3-yl)-piperidin-1-yl]-ethyl}-cyclohexyl)-2-(S)-tetrahydro-pyran-2-yl-acetamide | 488.0 | Separation of racemic mixture by chiral column | 488.4 |
| 35 | N-trans-(4-{2-[4-(6-Chloro-benzo[d]isoxazol-3-yl)-piperidin-1-yl]-ethyl}-cyclohexyl)-2-trans (4-methoxy-cyclohexyl)-acetamide | 516.12 | Trans 4-{2-[4-(6-Chloro-benzo[d]isoxazol-3-yl)-piperidin-1-yl]-ethyl}-cyclohexylamine (trifluoro-acetic acid salt) and Trans (4-Methoxy-cyclohexyl)-acetic acid (prepared from Methyl 4-hydroxyphenyl acetate and Nickel-aluminum alloy in MeOH and posterior methylation with NaH, MeI and ester hydrolysis with LiOH) | 516.5 |
| 36 | N-trans (4-{2-[4-(6-Chloro-benzo[d]isoxazol-3-yl)-piperidin-1-yl]-ethyl}-cyclohexyl)-2-(1,4-dioxa-spiro[4.5]dec-8-yl)-acetamide | 544.1 | Trans 4-{2-[4-(6-Chloro-benzo[d]isoxazol-3-yl)-piperidin-1-yl]-ethyl}-cyclohexylamine (trifluoro-acetic acid salt) and (1,4-Dioxa-spiro[4.5]dec-8-yl)-acetic acid (prepared by hydrolysis of the ethyl ester commercially available) | 544.0 |
| 37 | N-trans-(4-{2-[4-(6-Chloro-benzo[d]isoxazol-3-yl)-piperidin-1-yl]-ethyl}-cyclohexyl)-3,3-dimethoxy-propionamide | 478.0 | Trans 4-{2-[4-(6-Chloro-benzo[d]isoxazol-3-yl)-piperidin-1-yl]-ethyl}-cyclohexylamine (trifluoro-acetic acid salt) and 3,3-dimethoxy-propionic acid (prepared by hydrolysis of the commercially available methyl ester) | 478.1 |
| 38 | N-trans-(4-{2-[4-(6-Chloro-benzo[d]isoxazol-3-yl)-piperidin-1-yl]-ethyl}-cyclohexyl)-2-(tetrahydro-furan-2-yl)-acetamide | 474.0 | Trans 4-{2-[4-(6-Chloro-benzo[d]isoxazol-3-yl)-piperidin-1-yl]-ethyl}-cyclohexylamine (trifluoro-acetic acid salt) and 2-(tetrahydro-furan-2-yl)-acetic acid (prepared by hydrolysis of | 474.1 |

TABLE 3-continued

| Ex. No | Systematic name | MW | Starting materials | MW found (M + H)+ |
|---|---|---|---|---|
| 39 | (R)-N-trans (4-{2-[4-(6-Chloro-benzo[d]isoxazol-3-yl)-piperidin-1-yl]-ethyl}-cyclohexyl)-3-hydroxy-butyramide | 448.0 | the commercial available methyl ester) Trans 4-{2-[4-(6-Chloro-benzo[d]isoxazol-3-yl)-piperidin-1-yl]-ethyl}-cyclohexylamine (trifluoro-acetic acid salt) and (R)-3-hydroxy-butyric acid | 448.1 |
| 40 | N-trans (4-{2-[4-(6-Chloro-benzo[d]isoxazol-3-yl)-piperidin-1-yl]-ethyl}-cyclohexyl)-2-((S)-2,2-dimethyl-[1,3]dioxolan-4-yl)-acetamide | 504.0 | Trans 4-{2-[4-(6-Chloro-benzo[d]isoxazol-3-yl)-piperidin-1-yl]-ethyl}-cyclohexylamine (trifluoro-acetic acid salt) and -(4S-2,2-dimethyl-[1,3]dioxolan-4-yl)-acetic acid potassium salt (prepared by KO$^t$SiMe$_3$ conversion of methyl ester to the anhydrous acid salt following Tet. Letters, 25(51), 1984, 5831-5834) | 504.0 |
| 41 | N-trans (4-{2-[4-(6-Chloro-benzo[d]isoxazol-3-yl)-piperidin-1-yl]-ethyl}-cyclohexyl)-2-((1S,3S)-3-methoxy-cyclopentyl)-acetamide | 502.1 | Trans 4-{2-[4-(6-Chloro-benzo[d]isoxazol-3-yl)-piperidin-1-yl]-ethyl}-cyclohexylamine (trifluoro-acetic acid salt) and ((1S,3S)-3-Methoxy-cyclopentyl)-acetic acid potassium salt (prepared by KO$^t$SiMe$_3$ conversion of methyl ester to the anhydrous acid of the corresponding methyl ester synthesized following Helvetica Chimica Acta, Vol 75, 1992, 1945-1950) | 502.1 |

Example 42

N-trans(4-{2-[4-(6-Chloro-benzo[d]isoxazol-3-yl)-piperidin-1-yl]-ethyl}-cyclohexyl)-2-(4-methoxy-4-methyl-cyclohexyl)-acetamide 8-Methyl-1,4-dioxa-spiro(4,5) decan-8-ol Prepared by treatment of 1,4,-cyclohexanedione monoethylene acetal with methyl lithium in ether or MeMg I according to the procedure described on Journal of Organic Chemistry, 71(22), 2006, 8424-8430.

4-Methoxy-4-methyl-cyclohexanone

Prepared from reaction of 8-Methyl-1,4-dioxa-spiro(4,5) decan-8-ol (11.7 g, 68 mmol), NaH (137 mmol), MeI (273 mmol) and Me4NBr (17 mmol) in tetrahydrofuran (150 mL) at room temperature to obtain the o-methylated 1,4-dioxa spiro compound followed by treatment with 25% HCl (13.5 mL) in acetone to obtain (9.48 g, 97.6%) of the desired 4-Methoxy-4-methyl-cyclohexanone as an oil.

(4-Methoxy-4 methyl-cyclohexylidene)-acetic acid methyl ester

A mixture of trimethyl phosphonoacetate (9.11 mL, 56 mmol) and (40 mL, 64 mmol) of n-BuLi (1.6N) in DME (60 mL) is stirred for 10 minutes at 0° C. 4-Hydroxy-4-methyl-cyclohexanone (8 g, 56 mmol) was added and the mixture stirred 2.5 hours at 0° C. until TCL indicated complexion of the reaction. Product was obtained after extraction with dichloromethane (7.71 g, 69%).

(4-cis/trans-Methoxy-4-methyl-cyclohexyl)acetic acid methyl ester

Prepared from (4-Methoxy-4 methyl-cyclohexexylidene)-acetic acid methyl ester (7 g, 35 mmol) with Pd/C (10%) (35 mmol) in ethyl acetate under hydrogen overnight at room temperature. MS (m/e): 201.2 (M+H$^+$).

N-trans(4-{2-[4-(6-Chloro-benzo[d]isoxazol-3-yl)-piperidin-1-yl]-ethyl}-cyclohexyl)-2-(4-cis,trans-methoxy-4-methyl-cyclohexyl)-acetamide (4-cis/trans-Methoxy-4-methyl-cyclohexyl)acetic acid (anhydrous potassium salt) was prepared by conversion of (4-cis/trans-Methoxy-4-methyl-cyclohexyl)acetic acid methyl ester (0.157 g, 1 mmol) to the anhydrous acid salt using potassium trimethylsilanolate KO$^t$SiMe$_3$ (0.202 g, 2 mmol) and stirring with 2 mL of dichloromethane overnight following Tet. Letters, 25(51), 1984, 5831-5834. The solvent was evaporated and the obtained salt was solved on DMF (2 mL) and reacted as described for example 32, with Trans 4-{2-[4-(6-Chloro-benzo[d]isoxazol-3-yl)-piperidin-1-yl]-ethyl}-cyclohexylamine (trifluoro acetic acid salt) (0.300 g, 1 mol) 2-(1H-benzotriazol-1-yl)-1,1,3,3-tetramethyl uronium tetrafluoroborate (0.328 g, 1 mmol) and (0.530 mL, 3 mmol) of N-ethyldiisopropylamine for 12 hours at room temperature. MS (m/e): 530.0 (M+H$^+$).

Example 42A

N-trans(4-{2-[4-(6-Chloro-benzo[d]isoxazol-3-yl)-piperidin-1-yl]-ethyl}-cyclohexyl)-2-(4-trans-methoxy-4-methyl-cyclohexyl)-acetamide Obtained from separation using a chiral column (chiralpak AD) of the cis and trans mixture of N-trans(4-{2-[4-(6-

Chloro-benzo[d]isoxazol-3-yl)-piperidin-1-yl]-ethyl}-cyclohexyl)-2-(4-methoxy-4-methyl-cyclohexyl)-acetamide. MS (m/e): 530.0 (M+H⁺).

Example 42B

N-trans(4-{2-[4-(6-Chloro-benzo[d]isoxazol-3-yl)-piperidin-1-yl]-ethyl}-cyclohexyl)-2-(4-cis-methoxy-4-methyl-cyclohexyl)-acetamide Obtained from separation using a chiral column (chiralpak AD) of the cis and trans mixture of N-trans(4-{2-[4-(6-Chloro-benzo[d]isoxazol-3-yl)-piperidin-1-yl]-ethyl}-cyclohexyl)-2-(4-cis-methoxy-4-methyl-cyclohexyl)-acetamide. MS (m/e): 530.1 (M+H⁺).

Example 43

N-trans(4-{2-[4-(6-Chloro-benzo[d]isoxazol-3-yl)-piperidin-1-yl]-ethyl}-cyclohexyl)-3-methoxy-butyramide Prepared as described for example 32 from 3-methoxy-butyric acid and Trans 4-{2-[4-(6-Chloro-benzo[d]isoxazol-3-yl)-piperidin-1-yl]-ethyl}-cyclohexylamine (trifluoro acetic acid salt) in DMF for 4-12 hours at room temperature. MS (m/e): 462.3 (M+H⁺).

Example 43A (R)—N-trans(4-{2-[4-(6-Chloro-benzo[d]isoxazol-3-yl)-piperidin-1-yl]-ethyl}-cyclohexyl)-3-methoxy-butyramide Obtained from separation using a chiral column (chiralpak AD) of N-trans(4-{2-[4-(6-Chloro-benzo[d]isoxazol-3-yl)-piperidin-1-yl]-ethyl}-cyclohexyl)-3-methoxy-butyramide. MS (m/e): 462.5 (M+H⁺).

Example 43B (S)—N-(4-{2-[4-(6-Chloro-benzo[d]isoxazol-3-yl)-piperidin-1-yl]-ethyl}-cyclohexyl)-3-methoxy-butyramide Obtained from separation using a chiral column (chiralpak AD) of N-trans(4-{2-[4-(6-Chloro-benzo[d]isoxazol-3-yl)-piperidin-1-yl]-ethyl}-cyclohexyl)-3-methoxy-butyramide. MS (m/e): 462.5 (M+H⁺).

Example 44

N-trans-(4-{2-[4-(6-Chloro-benzo[d]isoxazol-3-yl)-piperidin-1-yl]-ethyl}-cyclohexyl)-2-trans (4-methoxymethyl-cyclohexyl)-acetamide 8-Methoxymethyl-1,4-dioxa-spiro[4.5]decane 1,4-Dioxaspiro[4.5]decane-8-methanol (2 g, 1 mmol) (commercial available or prepared as in Bioorganic & Medicinal Chemistry, 13(23), 6309-6323; 2005) is methylated using MeI (1.81 mL, 29 mmol) and NaH (0.813 g, 20 mmol) in tetrahydrofuran to obtain after 2 hours of stirring at room temperature 1.4 g (7.8 mmol) of the desired compound. MS (m/e): 187.3 (M+H⁺).

(4-Methoxymethyl-cyclohexylidene)-acetic acid methyl ester

4-Methoxymethyl-cyclohexanone was obtained by treatment of 8-Methoxymethyl-1,4-dioxa-spiro[4.5]decane (1.45 g, 8 mmol) with HCl 1N (15.6 mL, 16 mmol) in acetone (35 mL). Acetone was removed and the product was extracted with dichloromethane. The crude 4-Methoxymethyl-cyclohexanone was solved in 1 mL of dimethoxyethane and added into a mixture previously prepared by adding n-BuLi (3.54 mL, 6 mmol) to methyl diethylphosphonoacetate ((1.03 g, 5 mmol) in DME by stirring for 10 minutes at 0° C. After 2 hours TLC indicated formation of the (4-Methoxymethyl-cyclohexylidene)-acetic acid methyl ester (0.552 g, 2.7 mmol). MS (m/e): 199.1 (M+H⁺).

(4-Methoxymethyl-cyclohexyl)-acetic acid methyl ester

Prepared from (4-Methoxymethyl-cyclohexylidene)-acetic acid methyl ester (0.550 g, 3 mol) by hydrogenation using Pd/C (10%) (0.295 g, 0.3 mmol) in ethylacetate (15 mL). 1/3 cis/trans mixture.

N-trans-(4-{2-[4-(6-Chloro-benzo[d]isoxazol-3-yl)-piperidin-1-yl]-ethyl}-cyclohexyl)-2-trans (4-methoxymethyl-cyclohexyl)-acetamide Prepared from KO$^t$SiMe$_3$ and (4-Methoxymethyl-cyclohexyl)-acetic acid methyl ester to its potassium salt as described on example 42 and reaction of the salt with Trans 4-{2-[4-(6-Chloro-benzo[d]isoxazol-3-yl)-piperidin-1-yl]-ethyl}-cyclohexylamine (trifluoro acetic acid salt), 2-(1H-benzotriazol-1-yl)-1,1,3,3-tetramethyl uronium tetrafluoroborate and N-ethyldiisopropylamine for 12 hours at room temperature. Addition of ether and filtration yields the major trans isomer as a white solid. MS (m/e): 530.2 (M+H⁺).

Example 45

N-trans(4-{2-[4-(6-Chloro-benzo[d]isoxazol-3-yl)-piperidin-1-yl]-ethyl}-cyclohexyl)-2-(4-hydroxy-4-methyl-cyclohexyl)-acetamide (4-Oxo-cyclohexyl)-acetic acid Prepared from LiOH hydrolysis of (4-Oxo-Cyclohexyl)-acetic acid methyl ester (commercially available).

(4-Hydroxy-4-methyl-cyclohexyl)-acetic acid

Prepared using an excess of MeMgBr (26 mmol) in THF (20 ml) with (4-Oxo-cyclohexyl)-acetic acid (13 mmol) as described on Journal of American Society 93 (1), 1971, 121-129.

N-trans(4-{2-[4-(6-Chloro-benzo[d]isoxazol-3-yl)-piperidin-1-yl]-ethyl}-cyclohexyl)-2-(4-hydroxy-4-methyl-cyclohexyl)-acetamide Prepared as described for example 32 from (4-Hydroxy-4-methyl-cyclohexyl)-acetic acid and Trans 4-{2-[4-(6-Chloro-benzo[d]isoxazol-3-yl)-piperidin-1-yl]-ethyl}-cyclohexylamine (trifluoro acetic acid salt) in DMF for 4-12 hours at room temperature. MS (m/e): 516.1 (M+H⁺).

Example 46

N-trans(4-{2-[4-(6-Chloro-benzo[d]isoxazol-3-yl)-piperidin-1-yl]-ethyl}-cyclohexyl)-acetamide Prepared as described on example 1 from Trans 4-{2-[4-(6-Chloro-benzo[d]isoxazol-3-yl)-piperidin-1-yl]-ethyl}- cyclohexylamine (trifluoro acetic acid salt) in dichloromethane with triethylamine and acetylchloride. MS (m/e): 404.4 (M+H$^+$).

Example 47

Ethanesulfonic acid (4-trans {2-[4-(6-fluoro-benzo[d]isoxazol-3-yl)-piperidin-1-yl]-ethyl}-cyclohexyl)-amide Trans 4-{2-[4-(6-Fluoro-benzo[d]isoxazol-3-yl)-piperidin-1-yl]-ethyl}-cyclohexylamine (could be obtained as the trifluoroacetic acid salt) (intermediate F, example 1) (0.038 g, 0.11 mmol) was solved in THF (0.6 mL), ethanesulfonyl chloride was added followed by triethylamine (0.018 mL, 0.13 mmol) and the solution was stirred overnight. The mixture was concentrated to dryness and the residue was taken up on methanol and purified with preparative HPLC on reversed phase eluting with acetonitrile/water. The combined producted fractions were evaporated under reduced pressure to yield (0.023 g, 49%) of the product as a white solid. MS (m/e):: 438.1 (M+H$^+$).

According to the procedure described for the synthesis of example 47 further derivatives have been synthesized from the respective Trans 4-{2-[4-(6-Fluoro-benzo[d]isoxazol-3-yl)-piperidin-1-yl]-ethyl}-cyclohexylamine (could be obtained as the trifluoroacetic acid salt) and the corresponding sulfonyl chloride. They comprise examples 48 to 50 in table 4 hereinafter.

Example 52

N-trans-(4-{2-[4-(6-Chloro-benzo[d]isoxazol-3-yl)-piperidin-1-yl]-ethyl}-cyclohexyl)-3-cyano-propionamide Prepared in analogy to example 40 from trans-4-{2-[4-(6-chloro-benzo[d]isoxazol-3-yl)-piperidin-1-yl]-ethyl}-cyclohexylamine (trifluoro-acetic acid salt) and 3-cyanopropionic acid potassium salt (prepared by KO'SiMe$_3$ conversion of the methyl ester to the anhydrous acid salt following Tett. Letters, 25(51), 1984, 5831-5834). MS (m/e): 443.2 (M+H$^+$).

Example 53

N-trans-(4-{2-[4-(6-Chloro-benzo[d]isoxazol-3-yl)-piperidin-1-yl]-ethyl}-cyclohexyl)-2-(R)-tetrahydro-furan-2-yl-acetamide Obtained from separation using a chiral column (chiralpak AD) of N-trans-(4-{2-[4-(6-Chloro-benzo[d]isoxazol-3-yl)-piperidin-1-yl]-ethyl}-cyclohexyl)-2-(tetrahydro-furan-2-yl)-acetamide (Example 38). MS (m/e): 474.2 (M+H$^+$).

TABLE 4

| Ex. No | Systematic name | MW | Starting materials | MW found (M + H)$^+$ |
| --- | --- | --- | --- | --- |
| 48 | 4-Chloro-N-trans (4-{2-[4-(6-fluoro-benzo[d]isoxazol-3-yl)-piperidin-1-yl]-ethyl}-cyclohexyl)-benzenesulfonamide | 520.1 | Trans 4-{2-[4-(6-Fluoro-benzo[d]isoxazol-3-yl)-piperidin-1-yl]-ethyl}-cyclohexylamine (could be obtained as the trifluoroacetic acid salt) and benzenesulfonyl chloride | 520.3 |
| 49 | N-trans(4-{2-[4-(6-Fluoro-benzo[d]isoxazol-3-yl)-piperidin-1-yl]-ethyl}-cyclohexyl)-4-methoxy-benzenesulfonamide | 515.7 | Trans 4-{2-[4-(6-Fluoro-benzo[d]isoxazol-3-yl)-piperidin-1-yl]-ethyl}-cyclohexylamine (could be obtained as the trifluoroacetic acid salt) and 4-methoxy-benzene sulfonyl chloride | 516.3 |
| 50 | Pyridine-3-sulfonic acid trans(4-{2-[4-(6-fluoro-benzo[d]isoxazol-3-yl)-piperidin-1-yl]-ethyl}-cyclohexyl)-amide | 487.6 | Trans 4-{2-[4-(6-Fluoro-benzo[d]isoxazol-3-yl)-piperidin-1-yl]-ethyl}-cyclohexylamine (could be obtained as the trifluoroacetic acid salt) and pyridine-3-sulfonyl chloride hydrochloride | 488.2 |

Example 51

N-trans-(4-{2-[4-(6-Chloro-benzo[d]isoxazol-3-yl)-piperidin-1-yl]-ethyl}-cyclohexyl)-2-cyano-acetamide Prepared in analogy of example 32 from trans 4-{2-[4-(6-chloro-benzo[d]isoxazol-3-yl)-piperidin-1-yl]-ethyl}-cyclohexylamine (trifluoro acetic acid salt) and cyanoacetic acid with triethyl amine as the base. MS (m/e): 429.4 (M+H$^+$).

Example 54

N-trans-(4-{2-[4-(6-Chloro-benzo[d]isoxazol-3-yl)-piperidin-1-yl]-ethyl}-cyclohexyl)-2-cyclopropyl-acetamide The title compound, MS: m/e=444.3 (M+H$^+$), was prepared in accordance with the general method of example 32 from trans 4-{2-[4-(6-chloro-benzo[d]isoxazol-3-yl)-piperidin-1-yl]-ethyl}-cyclohexylamine (hydrochloric acid salt) and cyclopropylacetic acid.

Example 55

N-trans-(4-{2-[4-(6-Chloro-benzo[d]isoxazol-3-yl)-piperidin-1-yl]-ethyl}-cyclohexyl)-2-hydroxy-acetamide The title compound, MS: m/e=420.2 (M+H$^+$), was prepared in accordance with the general method of example 32 from trans 4-{2-[4-(6-chloro-benzo[d]isoxazol-3-yl)-piperidin-1-yl]-ethyl}-cyclohexylamine (hydrochloric acid salt) and glycolic acid.

Example 56

N-trans-(4-{2-[4-(6-Chloro-benzo[d]isoxazol-3-yl)-piperidin-1-yl]-ethyl}-cyclohexyl)-2-methanesulfonyl-acetamide The title compound, MS: m/e=482.1/484.0 (M+H$^+$), was prepared in accordance with the general method of example 32 from trans 4-{2-[4-(6-chloro-benzo[d]isoxazol-3-yl)-piperidin-1-yl]-ethyl}-cyclohexylamine (hydrochloric acid salt) and methanesulfonylacetic acid.

Example 57

N-trans-(4-{2-[4-(6-Chloro-benzo[d]isoxazol-3-yl)-piperidin-1-yl]-ethyl}-cyclohexyl)-2-[1,3]dioxan-2-yl-acetamide Step 1: [1,3]Dioxan-2-yl-acetic acid methyl ester Propane-1,-3-diol (2.45 ml, 36 mmol) was dissolved in 100 ml THF and cooled to 0-5° C. Sodium hydride (1.43 g, 40 mmol, 55%) was added and the reaction mixture stirred for 15 minutes at 0-5° C. Propyonic acid methyl ester (2.97 ml, 36 mmol) dissolved in 10 ml THF was added drop wise and stirred for 3 hours at 0-5° C. The reaction mixture was quenched with 2N HCl-solution and extracted two times with ethyl acetate. The organic extracts were washed with brine, dried with sodium sulfate, filtered and evaporated. The crude product was purified by flash chromatography on silica gel (dichloromethane). The desired compound was obtained as a colourless liquid (2.96 g, 52%).

Step 2: N-trans-(4-{2-[4-(6-Chloro-benzo[d]isoxazol-3-yl)-piperidin-1-yl]-ethyl}-cyclohexyl)-2-[1,3]dioxan-2-yl-acetamide

[1,3]Dioxan-2-yl-acetic acid methyl ester (130 mg, 0.81 mmol) (Step 1) was dissolved in 2 ml THF, 1 ml methanol and 1 ml water. Lithium hydroxide monohydrate (102 mg, 2.43 mmol) was added and the reaction mixture stirred for 16 hours at room temperature. The organic solvent was evaporated and the aqueous mixture was acidified with 2N HCl to pH 1. The mixture was evaporated to dryness and trans 4-{2-[4-(6-chloro-benzo[d]isoxazol-3-yl)-piperidin-1-yl]-ethyl}-cyclohexylamine (as a hydrochloric acid salt) (150 mg, 0.41 mmol) (Example 32, Intermediate F) in 1 ml DMF was added. N,N-Diisopropylethylamine (205 µl, 1.22 mmol) and 2-(1H-benzotriazol-1-yl)-1,1,3,3-tetramethyl uronium tetrafluoroborate [TBTU] (157 mg, 0.49 mmol) were added and the reaction stirred for 2 hours at room temperature. The reaction mixture was quenched with saturated NaHCO$_3$-solution and extracted with dichloromethane. The organic extract was washed with brine, dried with sodium sulfate, filtered and evaporated.

The crude product was purified by flash chromatography on silica gel (dichloromethane/methanol 100:0->90:10 gradient). The desired compound was obtained as a light yellow solid (61 mg, 33%), MS: m/e=490.3 (M+H$^+$).

Example 58

N-trans-(4-{2-[4-(5-Chloro-benzo[d]isoxazol-3-yl)-piperidin-1-yl]-ethyl}-cyclohexyl)-2-(4-methoxy-cyclohexyl)-acetamide Step 1: 5-Chloro-3-piperidin-4-yl-benzo[d]isoxazole hydrochloride The title compound can be prepared in accordance with literature described in the patent WO02066446 (Example 46 and 48) by using 5-chloro-2-fluorobenzaldehyde as starting material.

Step 2: Trans-(4-{2-[4-(5-Chloro-benzo[d]isoxazol-3-yl)-piperidin-1-yl]-ethyl}-cyclohexyl)-carbamic acid tert-butyl ester The title compound, MS: m/e=462.3 (M+H$^+$), was prepared in accordance with the general method of example 1, intermediate E from a mixture of 5-chloro-3-piperidin-4-yl-benzo[d]isoxazole hydrochloride and trans-[4-(2-oxo-ethyl)-cyclohexyl]-carbamic acid tert-butyl ester (Example 1, Intermediate C).

Step 3: Trans-4-{2-[4-(5-Chloro-benzo[d]isoxazol-3-yl)-piperidin-1-yl]-ethyl}-cyclohexylamine hydrochloride Trans-(4-{2-[4-(5-Chloro-benzo[d]isoxazol-3-yl)-piperidin-1-yl]-ethyl}-cyclohexyl)-carbamic acid tert-butyl ester (1.35 g, 2.92 mmol) was dissolved in 2 ml dichloromethane and 4N HCl in dioxane (8.8 ml, 38.8 mmol) was added. The white suspension was stirred for 4 hours at room temperature, diluted with diisopropylether and filtered. The crystals were washed with diisopropylether and dried for 2 hours at 50° C. and <20 mbar, to get the desired salt as a white solid (1.65 g, quant.) [MS: m/e=362.2 (M+H$^+$)].

Step 4: N-trans-(4-{2-[4-(5-Chloro-benzo[d]isoxazol-3-yl)-piperidin-1-yl]-ethyl}-cyclohexyl)-2-(4-methoxy-cyclohexyl)-acetamide Prepared as described for Example 40 from trans-4-{2-[4-(5-chloro-benzo[d]isoxazol-3-yl)-piperidin-1-yl]-ethyl}-cyclohexylamine hydrochloride (example 58, step 3) and trans-(4-methoxy-cyclohexyl)-acetic acid potassium salt (prepared from methyl 4-hydroxyphenyl acetate and Nickel-aluminum alloy in MeOH and posterior methylation with NaH, MeI and by KO$^t$SiMe$_3$ conversion of the methyl ester to the anhydrous acid salt following Tett. Letters, 25(51), 1984, 5831-5834). MS: m/e=516.0/517.1 (M+H$^+$).

Example 59

N-trans-(4-{2-[4-(5-Fluoro-benzo[d]isoxazol-3-yl)-piperidin-1-yl]-ethyl}-cyclohexyl)-methanesulfonamide Step 1: Trans-4-{2-[4-(5-Fluoro-benzo[d]isoxazol-3-yl)-piperidin-1-yl]-ethyl}-cyclohexylamine hydrochloride The title compound, MS: m/e=346.2 (M+H$^+$), was prepared in accordance with the general method of example 58, step 1, 2 and 3 starting from 2,5-difluorobenzaldehyde.

Step 2: N-trans-(4-{2-[4-(5-Fluoro-benzo[d]isoxazol-3-yl)-piperidin-1-yl]-ethyl}-cyclohexyl)-methanesulfonamide The title compound, MS: m/e=424.2 (M+H$^+$), was prepared in accordance with the general method of example 47 from trans-4-{2-[4-(5-fluoro-benzo[d]isoxazol-3-yl)-piperidin-1-yl]-ethyl}-cyclohexylamine hydrochloride and methansulfonyl chloride.

Example 60

N-trans-(4-{2-[4-(6-Chloro-5-fluoro-benzo[d]isoxazol-3-yl)-piperidin-1-yl]-ethyl}-cyclohexyl)-3-methoxy-propionamide

Step 1: Trans-4-{2-[4-(6-Chloro-5-fluoro-benzo[d]isoxazol-3-yl)-piperidin-1-yl]-ethyl}-cyclohexylamine hydrochloride The title compound, MS: m/e=380.3/382.3 (M+H$^+$), was prepared in accordance with the general method of example 58, step 1, 2 and 3 starting from 4-chloro-2,5-difluorobenzaldehyde.

Step 2: N-trans-(4-{2-[4-(6-Chloro-5-fluoro-benzo[d]isoxazol-3-yl)-piperidin-1-yl]-ethyl}-cyclohexyl)-3-methoxy-propionamide The title compound, MS: m/e=466.1/468.3 (M+H$^+$), was prepared in accordance with the general method of example 32 from trans-4-{2-[4-(6-chloro-5-fluoro-benzo[d]isoxazol-3-yl)-piperidin-1-yl]-ethyl}-cyclohexylamine hydrochloride and 3-methoxypropionic acid.

Example 61

N-trans-(4-{2-[4-(6-Chloro-5-fluoro-benzo[d]isoxazol-3-yl)-piperidin-1-yl]-ethyl}-cyclohexyl)-2-(tetrahydro-furan-2-yl)-acetamide The title compound, MS: m/e=492.3 (M+H$^+$), was prepared in accordance with the general method of example 60 from trans-4-{2-[4-(6-chloro-5-fluoro-benzo[d]isoxazol-3-yl)-piperidin-1-yl]-ethyl}-cyclohexylamine hydrochloride and 2-(tetrahydro-furan-2-yl)-acetic acid (prepared by hydrolysis of the commercial available methyl ester).

Example 62

N-trans-(4-{2-[4-(5,6-Difluoro-benzo[d]isoxazol-3-yl)-piperidin-1-yl]-ethyl}-cyclohexyl)-2-methoxy-acetamide

Step 1: Trans-4-{2-[4-(5,6-Difluoro-benzo[d]isoxazol-3-yl)-piperidin-1-yl]-ethyl}-cyclohexylamine hydrochloride The title compound, MS: m/e=364.4 (M+H$^+$), was prepared in accordance with the general method of example 58, step 1, 2 and 3 starting from 2,4,5-trifluorobenzaldehyde.

Step 2: N-trans-(4-{2-[4-(5,6-Difluoro-benzo[d]isoxazol-3-yl)-piperidin-1-yl]-ethyl}-cyclohexyl)-2-methoxy-acetamide The title compound, MS: m/e=436.3/437.4 (M+H$^+$), was prepared in accordance with the general method of example 32 from trans-4-{2-[4-(6-chloro-5-fluoro-benzo[d]isoxazol-3-yl)-piperidin-1-yl]-ethyl}-cyclohexylamine hydrochloride and methoxyacetic acid.

Example 63

N-trans-(4-{2-[4-(5,6-Difluoro-benzo[d]isoxazol-3-yl)-piperidin-1-yl]-ethyl}-cyclohexyl)-2-((1R,3R)-3-methoxy-cyclopentyl)-acetamide The title compound, MS: m/e=504.3 (M+H$^+$), was prepared in accordance with the general method of example 40 from trans-4-{2-[4-(5,6-difluoro-benzo[d]isoxazol-3-yl)-piperidin-1-yl]-ethyl}-cyclohexylamine hydrochloride (example 62, step 1) and rac-trans-(3-methoxy-cyclopentyl)-acetic acid potassium salt (prepared from rac-trans-(3-hydroxy-cyclopentyl)-acetic acid methyl ester (*Helvetica Chimica Acta—Vol.* 75 (1992) Page 1945 and 1950) and posterior methylation with NaH, MeI and by KO$^r$SiMe$_3$ conversion of the methyl ester to the anhydrous acid salt following Tett. Letters, 25(51), 1984, 5831-5834).

Example 64

N-trans-(4-{2-[4-(5,6-Difluoro-benzo[d]isoxazol-3-yl)-piperidin-1-yl]-ethyl}-cyclohexyl)-2-(4-methoxy-cyclohexyl)-acetamide The title compound, MS: m/e=518.4 (M+H$^+$), was prepared in accordance with the general method of example 40 from trans-4-{2-[4-(5,6-difluoro-benzo[d]isoxazol-3-yl)-piperidin-1-yl]-ethyl}-cyclohexylamine hydrochloride (example 62, step 1) and trans-(4-methoxy-cyclohexyl)-acetic acid potassium salt (prepared from methyl 4-hydroxyphenyl acetate and Nickel-aluminum alloy in MeOH and posterior methylation with NaH, MeI and by KO$^r$SiMe$_3$ conversion of the methyl ester to the anhydrous acid salt following Tett. Letters, 25(51), 1984, 5831-5834).

Example 65

N-trans-(4-{2-[4-(5,6-Difluoro-benzo[d]isoxazol-3-yl)-piperidin-1-yl]-ethyl}-cyclohexyl)-3-methoxy-propionamide The title compound, MS: m/e=450.3 (M+H$^+$), was prepared in accordance with the general method of example 32 from trans-4-{2-[4-(5,6-difluoro-benzo[d]isoxazol-3-yl)-piperidin-1-yl]-ethyl}-cyclohexylamine hydrochloride (example 62, step 1) and 3-methoxypropionic acid.

Example 66

N-trans-(4-{2-[4-(5,6-Difluoro-benzo[d]isoxazol-3-yl)-piperidin-1-yl]-ethyl}-cyclohexyl)-acetamide The title compound, MS: m/e=406.3 (M+H$^+$), was prepared in accordance with the general method of example 32 from trans-4-{2-[4-(5,6-difluoro-benzo[d]isoxazol-3-yl)-piperidin-1-yl]-ethyl}-cyclohexylamine hydrochloride (example 62, step 1) and acetic acid.

Example 67

N-trans-(4-{2-[4-(5,6-Difluoro-benzo[d]isoxazol-3-yl)-piperidin-1-yl]-ethyl}-cyclohexyl)-2-hydroxy-acetamide The title compound, MS: m/e=422.2 (M+H$^+$), was prepared in accordance with the general method of example 32 from trans-4-{2-[4-(5,6-difluoro-benzo[d]isoxazol-3-yl)-piperidin-1-yl]-ethyl}-cyclohexylamine hydrochloride (example 62, step 1) and glycolic acid.

Example 68

N-trans-(4-{2-[4-(5,6-Difluoro-benzo[d]isoxazol-3-yl)-piperidin-1-yl]-ethyl}-cyclohexyl)-3-hydroxy-propionamide The title compound, MS: m/e=436.0 (M+H$^+$), was prepared in accordance with the general method of example 32 from trans-4-{2-[4-(5,6-difluoro-benzo[d]isoxazol-3-yl)-piperidin-1-yl]-ethyl}-cyclohexylamine hydrochloride (example 62, step 1) and 3-hydroxypropionic acid.

Example 69

N-trans-(4-{2-[4-(5,6-Difluoro-benzo[d]isoxazol-3-yl)-piperidin-1-yl]-ethyl}-cyclohexyl)-2-(4-hydroxy-cyclohexyl)-acetamide The title compound, MS: m/e=504.1 (M+H$^+$), was prepared in accordance with the general method of example 40 from trans-4-{2-[4-(5,6-difluoro-benzo[d]isoxazol-3-yl)-piperidin-1-yl]-ethyl}-cyclohexylamine hydrochloride (example 62, step 1) and trans-(4-hydroxy-cyclohexyl)-acetic acid potassium salt (prepared from methyl 4-hydroxyphenyl acetate and Nickel-aluminum alloy in MeOH and by KO$^t$SiMe$_3$ conversion of the methyl ester to the anhydrous acid salt following Tett. Letters, 25(51), 1984, 5831-5834).

Example 70

N-trans-(4-{2-[4-(5,6-Difluoro-benzo[d]isoxazol-3-yl)-piperidin-1-yl]-ethyl}-cyclohexyl)-2-((1R,3R)-3-hydroxy-cyclopentyl)-acetamide The title compound, MS: m/e=490.4 (M+H$^+$), was prepared in accordance with the general method of example 40 from trans-4-{2-[4-(5,6-difluoro-benzo[d]isoxazol-3-yl)-piperidin-1-yl]-ethyl}-cyclohexylamine hydrochloride (example 62, step 1) and rac-trans-(3-hydroxy-cyclopentyl)-acetic acid potassium salt (prepared as described in literature *Helvetica Chimica Acta—Vol.* 75 (1992) Page 1945 and 1950 and by KO$^t$SiMe$_3$ conversion of the methyl ester to the anhydrous acid salt following Tett. Letters, 25(51), 1984, 5831-5834).

Example 71

Tetrahydro-pyran-4-carboxylic acid trans-(4-{2-[4-(5,6-difluoro-benzo[d]isoxazol-3-yl)-piperidin-1-yl]-ethyl}-cyclohexyl)-amide The title compound, MS: m/e=476.3 (M+H$^+$), was prepared in accordance with the general method of example 32 from trans-4-{2-[4-(5,6-difluoro-benzo[d]isoxazol-3-yl)-piperidin-1-yl]-ethyl}-cyclohexylamine hydrochloride (example 62, step 1) and tetrahydro-pyran-4-carboxylic acid.

Example 72

N-trans-(4-{2-[4-(5,6-Difluoro-benzo[d]isoxazol-3-yl)-piperidin-1-yl]-ethyl}-cyclohexyl)-2-[1,3]dioxan-2-yl-acetamide The title compound, MS: m/e=492.3 (M+H$^+$), was prepared in accordance with the general method of example 40 from trans-4-{2-[4-(5,6-difluoro-benzo[d]isoxazol-3-yl)-piperidin-1-yl]-ethyl}-cyclohexylamine hydrochloride (example 62, step 1) and [1,3]Dioxan-2-yl-acetic acid potassium salt (prepared as described in example 57, step 1 and by KO$^t$SiMe$_3$ conversion of the methyl ester to the anhydrous acid salt following Tett. Letters, 25(51), 1984, 5831-5834).

Example 73

N-trans-(4-{2-[4-(6-Methyl-benzo[d]isoxazol-3-yl)-piperidin-1-yl]-ethyl}-cyclohexyl)-acetamide Step 1: Trans-4-{2-[4-(6-Methyl-benzo[d]isoxazol-3-yl)-piperidin-1-yl]-ethyl}-cyclohexylamine hydrochloride The title compound, MS: m/e=342.3 (M+H$^+$), was prepared in accordance with the general method of example 58, step 1, 2 and 3 starting from 2-fluoro-4-methylbenzaldehyde.

Step 2: N-trans-(4-{2-[4-(6-Methyl-benzo[d]isoxazol-3-yl)-piperidin-1-yl]-ethyl}-cyclohexyl)-acetamide The title compound, MS: m/e=384.3 (M+H$^+$), was prepared in accordance with the general method of example 32 from trans-4-{2-[4-(6-methyl-benzo[d]isoxazol-3-yl)-piperidin-1-yl]-ethyl}-cyclohexylamine hydrochloride and acetic acid.

Example A

Film coated tablets containing the following ingredients can be manufactured in a conventional manner:

| Ingredients | Per tablet | |
| --- | --- | --- |
| Kernel: | | |
| Compound of formula (I) | 10.0 mg | 200.0 mg |
| Microcrystalline cellulose | 23.5 mg | 43.5 mg |
| Lactose hydrous | 60.0 mg | 70.0 mg |
| Povidone K30 | 12.5 mg | 15.0 mg |
| Sodium starch glycolate | 12.5 mg | 17.0 mg |
| Magnesium stearate | 1.5 mg | 4.5 mg |
| (Kernel Weight) | 120.0 mg | 350.0 mg |
| Film Coat: | | |
| Hydroxypropyl methyl cellulose | 3.5 mg | 7.0 mg |
| Polyethylene glycol 6000 | 0.8 mg | 1.6 mg |
| Talc | 1.3 mg | 2.6 mg |
| Iron oxide (yellow) | 0.8 mg | 1.6 mg |
| Titanium dioxide | 0.8 mg | 1.6 mg |

The active ingredient can be sieved and mixed with microcrystalline cellulose, and the mixture can be granulated with a solution of polyvinylpyrrolidone in water. The granulate can be mixed with sodium starch glycolate and magnesiumstearate and compressed to yield kernels of 120 or 350 mg respectively. The kernels then can be lacquered with an aqueous solution/suspension of the above mentioned film coat.

Example B

Capsules containing the following ingredients can be manufactured in a conventional manner:

| Ingredients | Per capsule |
| --- | --- |
| Compound of formula (I) | 25.0 mg |
| Lactose | 150.0 mg |
| Maize starch | 20.0 mg |
| Talc | 5.0 mg |

The components can be sieved and mixed and filled into capsules of size 2.

Example C

Injection solutions can have the following composition:

| Compound of formula (I) | 3.0 mg |
| --- | --- |
| Gelatine | 150.0 mg |
| Phenol | 4.7 mg |
| Sodium carbonate | to obtain a final pH of 7 |
| Water for injection solutions | ad 1.0 ml |

Example D

Soft gelatin capsules containing the following ingredients can be manufactured in a conventional manner:

| Capsule contents | |
| --- | --- |
| Compound of formula (I) | 5.0 mg |
| Yellow wax | 8.0 mg |
| Hydrogenated Soya bean oil | 8.0 mg |
| Capsule contents | |
| Partially hydrogenated plant oils | 34.0 mg |
| Soya bean oil | 110.0 mg |
| Weight of capsule contents | 165.0 mg |
| Gelatin capsule | |
| Gelatin | 75.0 mg |
| Glycerol 85% | 32.0 mg |
| Karion 83 | 8.0 mg (dry matter) |
| Titanium dioxide | 0.4 mg |
| Iron oxide yellow | 1.1 mg |

The active ingredient can be dissolved in a warm melting of the other ingredients, and the mixture can be filled into soft gelatin capsules of appropriate size. The filled soft gelatin capsules then can be treated according to the usual procedures.

Example E

Sachets containing the following ingredients can be manufactured in a conventional manner:

| Compound of formula (I) | 50.0 mg |
| --- | --- |
| Lactose, fine powder | 1015.0 mg |
| Microcrystalline cellulose (AVICEL PH 102) | 1400.0 mg |
| Sodium carboxymethyl cellulose | 14.0 mg |
| Polyvinylpyrrolidone K 30 | 10.0 mg |
| Magnesium stearate | 10.0 mg |
| Flavoring additives | 1.0 mg |

The active ingredient can be mixed with lactose, microcrystalline cellulose and sodium carboxymethyl cellulose and granulated with a mixture of polyvinylpyrrolidone in water. The granulate can be mixed with magnesium stearate and the flavoring additives and be filled into sachets.

The invention claimed is:

1. A compound of formula (I):

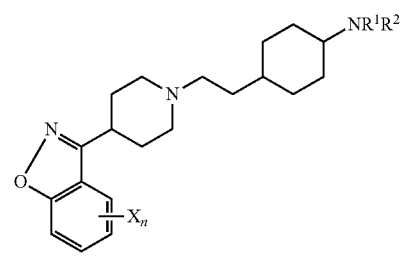

wherein:
each X is independently halogen, cyano; $C_{1-6}$-alkyl, $C_{1-6}$-alkoxy or $C_{1-6}$-haloalkyl;
n is 0, 1, 2 or 3;
$R^1$ is H or $C_{1-6}$-alkyl;
$R^2$ is

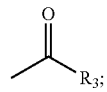

$R^3$ is hydrogen, $C_{1-6}$-alkyl, $C_{2-6}$-alkenyl, $C_{2-6}$-alkynyl, $C_{1-6}$-alkoxy, $C_{3-10}$-cycloalkyl, aryl, each of which is optionally substituted by one to five substituents selected from the group consisting of:
halo,
cyano,
—$SO_2$—$C_{1-6}$-alkyl,
hydroxyl,
$C_{1-6}$-alkyl,
$C_{1-6}$-haloalkyl,
—CO(O)—$C_{1-6}$-alkyl,
$C_{1-6}$-alkoxy optionally substituted by one or more $R^a$,
$C_{3-10}$-cycloalkyl optionally substituted by one or more $R^a$,
aryl optionally substituted by one or more $R^a$,
and
—$NR^bR^c$,
wherein $R^b$ is H or $C_{1-6}$-alkyl and wherein $R^c$ is H, $C_{1-6}$-alkyl or aryl optionally substituted by one or more $R^a$;
wherein $R^a$ is selected from:
halo,
cyano,
oxo,
hydroxyl,
halobenzenesulfonyl,
$C_{1-6}$-alkyl $C_{1-6}$-haloalkyl,
—NH(CO)—$C_{1-6}$-alkyl,
di($C_{1-6}$)alkylamino,
—O(CO)—$C_{1-6}$-alkyl,
$C_{1-6}$-alkylsulfonyl, and
$C_{1-6}$-alkoxy $C_{1-6}$-haloalkoxy,
or a pharmaceutically acceptable salt thereof and wherein the substitution at the central cyclohexyl ring is in the trans configuration.

2. The compound of claim 1, wherein:
each X is independently fluorine or chlorine;
n is 0, 1 or 2;
$R^1$ is hydrogen;

$R^2$ is

and
or a pharmaceutically acceptable salt thereof.

3. The compound of claim 1 having formula (Ia):

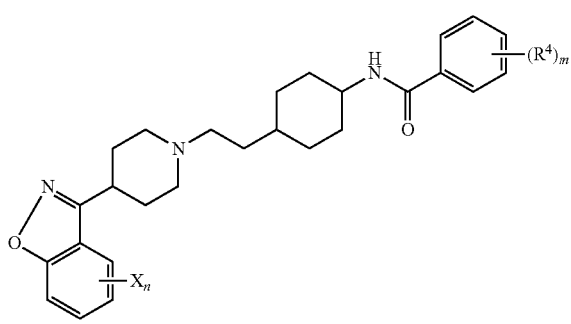

(Ia)

wherein
each X is independently fluorine or chlorine;
n is 0, 1 or 2;
m is 0, 1, 2 or 3;
$R^4$ is selected from the group consisting of:
  halo,
  cyano,
  hydroxy,
  $C_{1-6}$-haloalkyl,
  di($C_{1-6}$)alkylamino,
  —CO(O)—$C_{1-6}$-alkyl,
  $C_{1-6}$-alkoxy optionally substituted by one or more $R^a$,
  $C_{3-10}$-cycloalkyl optionally substituted by one or more $R^a$,
  aryl optionally substituted by one or more $R^a$, and
  —$NR^bR^c$,
wherein $R^a$, $R^b$ and $R^c$ are as defined in claim 1;
or a pharmaceutically acceptable salt thereof.

4. The compound of claim 3, wherein
each X is independently fluorine or chlorine;
n is 1;
m is 0, 1 or 2;
$R^4$ is selected from the group consisting of:
  halo, and
  $C_{1-6}$-alkyl optionally substituted by one or more $R^a$,
wherein $R^a$ is selected from
  halo,
  oxo,
  hydroxyl and
  $C_{1-6}$-alkyl
or a pharmaceutically acceptable salt thereof.

5. The compound of claim 3, selected from the group consisting of
  N-trans-(4-{2-[4-(6-Fluoro-benzo[d]isoxazol-3-yl)-piperidin-1-yl]-ethyl}-cyclohexyl)-4-methoxy-benzamide
  4-tert-Butoxy-N-trans(4-{2-[4-(6-fluoro-benzo[d]isoxazol-3-yl]-piperidin-1-yl]-ethyl}-cyclohexyl)-benzamide, and
  4-Chloro-N-trans(4-{2-[4-(6-fluoro-benzo[d]isoxazol-3-yl)-piperidin-1-yl]-ethyl}-cyclohexyl)-benzamide.

6. The compound of claim 1 having formula (Ic):

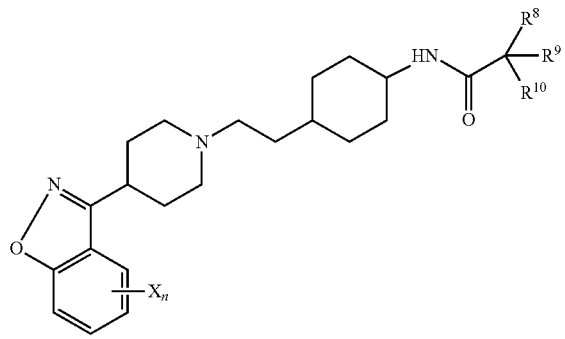

(Ic)

wherein
each X is independently fluorine or chlorine;
n is 0, 1 or 2;
$R^8$ and $R^9$ form a 3-, 4-, 5-, or 6-membered saturated ring, two;
$R^{10}$ is selected from the group consisting of halogen, cyano, hydroxy, $C_{1-6}$-alkyl, $C_{1-6}$-haloalkyl and $C_{1-6}$-alkoxy;
or a pharmaceutically acceptable salt thereof.

7. The compound of claim 1 having formula (Id):

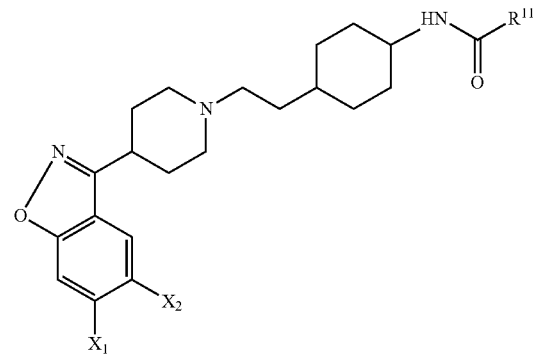

(Id)

wherein
$X_1$=H and $X_2$=fluoro or chloro; or
$X_2$=H and $X_1$=fluoro or chloro; and
$R^{11}$ is selected from the group consisting of $C_{1-6}$-alkyl and $C_{1-6}$-alkoxy, each of which is optionally substituted by halogen, hydroxy, $C_{1-6}$-alkyl, $C_{1-6}$-haloalkyl, $C_{1-6}$-alkoxy or $C_{5-6}$-cycloalkyl which is optionally substituted by $C_{1-6}$-alkyl or $C_{1-6}$-alkoxy; or a pharmaceutically acceptable salt thereof.

8. The compound of claim 7 having formula (Id'):

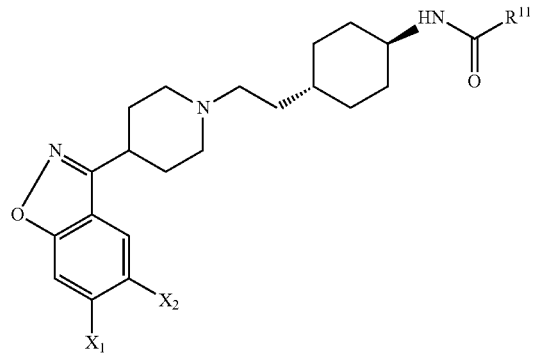

(Id')

or a pharmaceutically acceptable salt thereof.

9. The compound of claim 8, selected from the group consisting of 4N-trans(4-{2-[4-(6-Fluoro-benzo[d]isoxazol-3-yl)-piperidin-1-yl]-ethyl}-cyclohexyl)-acetamide, N-trans(4-{2-[4-(6-Fluoro-benzo[d]isoxazol-3-yl)-piperidin-1-yl]-ethyl}-cyclohexyl)-3-methoxy-propionamide, N-trans(4-{2-[4-(5-Fluoro-benzo[d]isoxazol-3-yl)-piperidin-1-yl]-ethyl}-cyclohexyl)-acetamide,-N-trans(4-{2-[4-(5-Fluoro-benzo[d]isoxazol-3-yl)-piperidin-1-yl]-ethyl}-cyclohexyl)-3-methoxy-propionamide, Trans 4-{2-[4-(6-Fluoro-benzo[d]isoxazol-3-yl)-piperidin-1-yl]-ethyl}-cyclohexylamine, 3,3,3-Trifluoro-N-trans(4-{2-[4-(6-fluoro-benzo[d]isoxazol-3-yl)-piperidin-1-yl]-ethyl}-cyclohexyl)-propionamide.

10. The compound of claim 8, selected from the group consisting of 2-(3,5-Dimethoxy-phenyl)-N-trans(4-{2-[4-(6-fluoro-benzo[d]isoxazol-3-yl)-piperidin-1-yl]-ethyl}-cyclohexyl)-acetamide, N-trans(4-{2-[4-(6-Chloro-benzo[d]isoxazol-3-yl)-piperidin-1-yl]-ethyl}-cyclohexyl)-3-methoxy-propionamide, N-trans(4-{2-[4-(6-Chloro-benzo[d]isoxazol-3-yl)-piperidin-1-yl]-ethyl}-cyclohexyl)-acetamide, N-trans-(4-{2-[4-(6-Chloro-benzo[d]isoxazol-3-yl)-piperidin-1-yl]-ethyl}-cyclohexyl)-3,3,3-trifluoro-2-hydroxy-propionamide, N-trans-(4-{2-[4-(6-Chloro-benzo[d]isoxazol-3-yl)-piperidin-1-yl]-ethyl}-cyclohexyl)-2-trans (4-methoxy-cyclohexyl)-acetamide, and N-trans-(4-{2-[4-(6-Chloro-benzo[d]isoxazol-3-yl)-piperidin-1-yl]-ethyl}-cyclohexyl)-3,3-dimethoxy-propionamide.

11. The compound of claim 1 having formula (Ie):

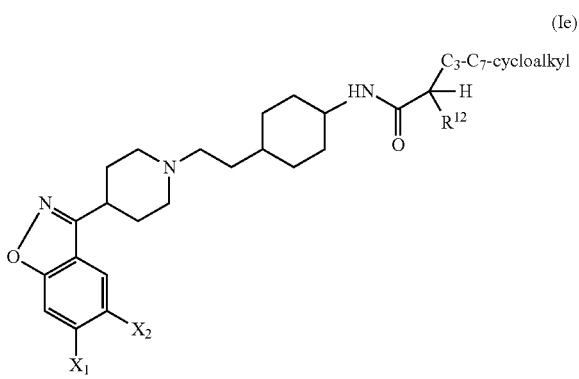

(Ie)

wherein $X_1$=H and $X_2$=fluoro or chloro; or $X_2$=H and $X_1$=fluoro or chloro; and $R^{12}$ is selected from the group consisting of halo, hydroxy, cyano, $C_{1-6}$-alkyl, $C_{1-6}$-haloalkyl and $C_{1-6}$-alkoxy;

or a pharmaceutically acceptable salt thereof.

12. The compound of claim 11 having formula (Ie'):

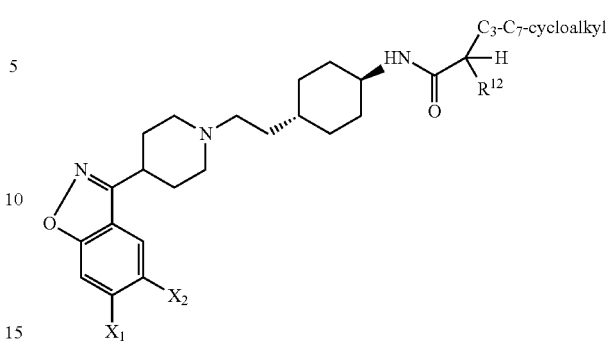

(Ie')

or a pharmaceutically acceptable salt thereof.

13. The compound of claim 12, selected from the group consisting of 1-Hydroxy-cyclopropanecarboxylic acid trans (4-{2-[4-(6-fluoro-benzo[d]isoxazol-3-yl)-piperidin-1-yl]-ethyl}-cyclohexyl)-amide, and 1-Trifluoromethyl-cyclobutanecarboxylic acid trans(4-{2-[4-(6-fluoro-benzo[d]isoxazol-3-yl)-piperidin-1-yl]-ethyl}-cyclohexyl)-amide.

14. The compound of claim 1, selected from the group consisting of:

(R)—N-trans(4-{2-[4-(6-Chloro-benzo[d]isoxazol-3-yl)-piperidin-1-yl]-ethyl}-cyclohexyl)-3-hydroxy-butyramide, N-trans(4-{2-[4-(6-Chloro-benzo[d]isoxazol-3-yl)-piperidin-1-yl]-ethyl}-cyclohexyl)-2-((1S,3S)-3-methoxy-cyclopentyl)-acetamide, and N-trans(4-{2-[4-(6-Chloro-benzo[d]isoxazol-3-yl)-piperidin-1-yl]-ethyl}-cyclohexyl)-2-(4-methoxy-4-methyl-cyclohexyl)-acetamide.

15. The compound of claim 1, selected from the group consisting of

N-trans(4-{2-[4-(6-Chloro-benzo[d]isoxazol-3-yl)-piperidin-1-yl]-ethyl}-cyclohexyl)-2-(4-trans-methoxy-4-methyl-cyclohexyl)-acetamide, N-trans(4-{2-[4-(6-Chloro-benzo[d]isoxazol-3-yl)-piperidin-1-yl]-ethyl}-cyclohexyl)-2-(4-cis-methoxy-4-methyl-cyclohexyl)-acetamide, (R)—N-trans(4-{2-[4-(6-Chloro-benzo[d]isoxazol-3-yl)-piperidin-1-yl]-ethyl}-cyclohexyl)-3-methoxy-butyramide, (S)—N-(4-{2-[4-(6-Chloro-benzo[d]isoxazol-3-yl)-piperidin-1-yl]-ethyl}-cyclohexyl)-3-methoxybutyramide, N-trans-(4-{2-[4-(6-Chloro-benzo[d]isoxazol-3-yl)-piperidin-1-yl]-ethyl}-cyclohexyl)-2-trans(4-methoxymethyl-cyclohexyl)-acetamide, N-trans(4-{2-[4-(6-Chloro-benzo[d]isoxazol-3-yl)-piperidin-1-yl]-ethyl}-cyclohexyl)-2-(4-hydroxy-4-methyl-cyclohexyl)-acetamide, N-trans-(4-{2-[4-(6-Chloro-benzo[d]isoxazol-3-yl)-piperidin-1-yl]-ethyl}-cyclohexyl)-3-cyano-propionamide, and N-trans-(4-{2-[4-(6-Chloro-benzo[d]isoxazol-3-yl)-piperidin-1-yl]-ethyl}-cyclohexyl)-2-cyano-acetamide.

16. The compound of claim 1, selected from the group consisting of

N-trans-(4-{2-[4-(6-Chloro-benzo[d]isoxazol-3-yl)-piperidin-1-yl]-ethyl}-cyclohexyl)-2-cyclopropyl-acetamide, N-trans-(4-{2-[4-(6-Chloro-benzo[d]isoxazol-3-yl)-piperidin-1-yl]-ethyl}-cyclohexyl)-2-hydroxy-acetamide, N-trans-(4-{2-[4-(6-Chloro-benzo[d]isoxazol-3-yl)-piperidin-1-yl]-ethyl}-cyclohexyl)-2-methanesulfonyl-acetamide, N-trans-(4-{2-[4-(5-Chloro-benzo[d]isoxazol-3-yl)-piperidin-1-yl]-ethyl}-cyclohexyl)-2-(4-methoxy-cyclohexyl)-acetamide,
N-trans-(4-{2-[4-(6-Chloro-5-fluoro-benzo[d]isoxazol-3-yl)-piperidin-1-yl]-ethyl}-cyclohexyl)-3-methoxy-propionamide,
N-trans-(4-{2-[4-(5,6-Difluoro-benzo[d]isoxazol-3-yl)-piperidin-1-yl]-ethyl}-cyclohexyl)-2-methoxy-acetamide, and
N-trans-(4-{2-[4-(5,6-Difluoro-benzo[d]isoxazol-3-yl)-piperidin-1-yl]-ethyl}-cyclohexyl)-2-((1R,3R)-3-methoxy-cyclopentyl)-acetamide.

17. The compound of claim 1, selected from the group consisting of
N-trans-(4-{2-[4-(5,6-Difluoro-benzo[d]isoxazol-3-yl)-piperidin-1-yl]-ethyl}-cyclohexyl)-2-(4-methoxy-cyclohexyl)-acetamide,
N-trans-(4-{2-[4-(5,6-Difluoro-benzo[d]isoxazol-3-yl)-piperidin-1-yl]-ethyl}-cyclohexyl)-3-methoxy-propionamide,
N-trans-(4-{2-[4-(5,6-Difluoro-benzo[d]isoxazol-3-yl)-piperidin-1-yl]-ethyl}-cyclohexyl)-acetamide,
N-trans-(4-{2-[4-(5,6-Difluoro-benzo[d]isoxazol-3-yl)-piperidin-1-yl]-ethyl}-cyclohexyl)-2-hydroxy-acetamide,
N-trans-(4-{2-[4-(5,6-Difluoro-benzo[d]isoxazol-3-yl)-piperidin-1-yl]-ethyl}-cyclohexyl)-3-hydroxy-propionamide,
N-trans-(4-{2-[4-(5,6-Difluoro-benzo[d]isoxazol-3-yl)-piperidin-1-yl]-ethyl}-cyclohexyl)-2-(4-hydroxy-cyclohexyl)-acetamide,
N-trans-(4-{2-[4-(5,6-Difluoro-benzo[d]isoxazol-3-yl)-piperidin-1-yl]-ethyl}-cyclohexyl)-2-((1R,3R)-3-hydroxy-cyclopentyl)-acetamide, and
N-trans-(4-{2-[4-(6-Methyl-benzo[d]isoxazol-3-yl)-piperidin-1-yl]-ethyl}-cyclohexyl)-acetamide.

18. A pharmaceutical composition comprising a therapeutically effective amount of a compound of formula (I):

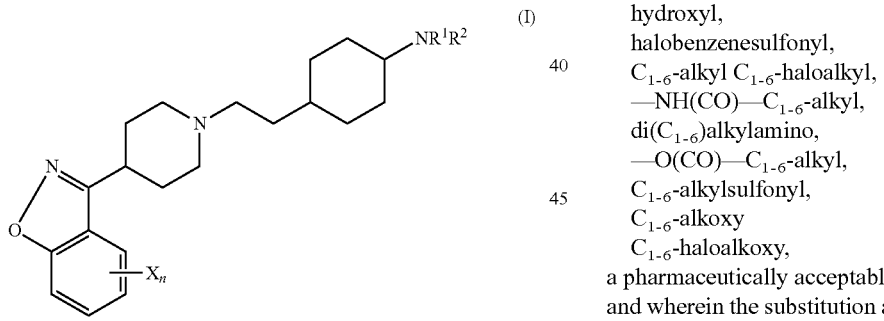

wherein:
each X is independently halogen, cyano; $C_{1-6}$-alkyl, $C_{1-6}$-alkoxy or $C_{1-6}$-haloalkyl;
n is 0, 1, 2 or 3;
$R^1$ is H or $C_{1-6}$-alkyl;
$R^2$ is

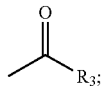

$R^3$ is hydrogen, $C_{1-6}$-alkyl, $C_{2-6}$-alkenyl, $C_{2-6}$-alkynyl, $C_{1-6}$-alkoxy, $C_{3-10}$-cycloalkyl, aryl, each of which is optionally substituted by one to five substituents selected from the group consisting of:
halo,
cyano,
—$SO_2$—$C_{1-6}$-alkyl,
hydroxyl,
$C_{1-6}$-alkyl,
$C_{1-6}$-haloalkyl,
—CO(O)—$C_{1-6}$-alkyl,
$C_{1-6}$-alkoxy optionally substituted by one or more $R^a$,
$C_{3-10}$-cycloalkyl optionally substituted by one or more $R^a$,
aryl optionally substituted by one or more $R^a$,
—NRbRc,
wherein $R^b$ is H or $C_{1-6}$-alkyl and wherein $R^c$ is H, $C_{1-6}$-alkyl or aryl optionally substituted by one or more $R^a$;
wherein $R^a$ is selected from:
halo,
cyano,
oxo,
hydroxyl,
halobenzenesulfonyl,
$C_{1-6}$-alkyl $C_{1-6}$-haloalkyl,
—NH(CO)—$C_{1-6}$-alkyl,
di($C_{1-6}$)alkylamino,
—O(CO)—$C_{1-6}$-alkyl,
$C_{1-6}$-alkylsulfonyl,
$C_{1-6}$-alkoxy
$C_{1-6}$-haloalkoxy,
a pharmaceutically acceptable salt thereof,
and wherein the substitution at the central cyclohexyl ring is in the trans configuration.

* * * * *